United States Patent
Brooks

(10) Patent No.: US 11,397,432 B2
(45) Date of Patent: *Jul. 26, 2022

(54) REMOTE VEHICLE OPERATOR ASSIGNMENT SYSTEM

(71) Applicant: Transportation IP Holdings, LLC, Norwalk, CT (US)

(72) Inventor: James D. Brooks, Schenectady, NY (US)

(73) Assignee: Transportation IP Holdings, LLC, Norwalk, CT (US)

( * ) Notice: Subject to any disclaimer, the term of this patent is extended or adjusted under 35 U.S.C. 154(b) by 761 days.

This patent is subject to a terminal disclaimer.

(21) Appl. No.: 16/046,493

(22) Filed: Jul. 26, 2018

(65) Prior Publication Data

US 2018/0356814 A1 Dec. 13, 2018

Related U.S. Application Data

(63) Continuation of application No. 15/460,431, filed on Mar. 16, 2017, now Pat. No. 10,705,519, which is a
(Continued)

(51) Int. Cl.
*G05D 1/00* (2006.01)
*A61B 5/318* (2021.01)
(Continued)

(52) U.S. Cl.
CPC ......... *G05D 1/0027* (2013.01); *A61B 5/0077* (2013.01); *A61B 5/0205* (2013.01);
(Continued)

(58) Field of Classification Search
CPC .. G05D 1/0027; G05D 1/0077; A61B 5/0077; A61B 5/0205; A61B 5/0402;
(Continued)

(56) References Cited

U.S. PATENT DOCUMENTS

| 4,041,283 A | 8/1977 | Mosier |
| 6,558,164 B2 | 5/2003 | Raha |

(Continued)

FOREIGN PATENT DOCUMENTS

| WO | 2013172840 A1 | 11/2013 |
| WO | 2016028228 A1 | 2/2016 |

(Continued)

OTHER PUBLICATIONS

Baldwin, "Phantom Auto Will Drive Your Autonomous Car if it Gets Confused", Engadget, May 4, 2018 (12 pages).
(Continued)

*Primary Examiner* — Peter D Nolan
*Assistant Examiner* — Luke Huynh
(74) *Attorney, Agent, or Firm* — The Small Patent Law Group LLC; Christopher R. Carroll

(57) ABSTRACT

An assignment system and method determine time-variable risk profiles for separate vehicle systems that are remotely controlled by operators located off-board the vehicle systems. The time-variable risk profiles represent risks to travel of the vehicle systems that change with respect to time. An operator staffing demand for the vehicle systems may be determined based on the time-variable risk profiles. The staffing demand represents how many operators are needed for remotely controlling the vehicle systems at different times and a required qualification of one or more operators. The system and method also assign operators to remotely monitor and/or control the vehicle systems based on the risk profiles and, optionally, the staffing demand. The operator assigned to one or more vehicle systems changes with respect to time while the vehicle systems are moving along routes.

23 Claims, 25 Drawing Sheets

Related U.S. Application Data continuation-in-part of application No. 15/402,797, filed on Jan. 10, 2017, now Pat. No. 10,279,825.

(60) Provisional application No. 62/327,101, filed on Apr. 25, 2016.

(51) Int. Cl.

| | | |
|---|---|---|
| *A61B 5/369* | (2021.01) | |
| *B61L 27/14* | (2022.01) | |
| *B61L 27/40* | (2022.01) | |
| *A61B 5/00* | (2006.01) | |
| *A61B 5/0205* | (2006.01) | |
| *A61B 5/11* | (2006.01) | |
| *A61B 5/18* | (2006.01) | |
| *H04L 67/52* | (2022.01) | |
| *B61L 3/12* | (2006.01) | |
| *A61B 5/021* | (2006.01) | |
| *A61B 5/024* | (2006.01) | |
| *A61B 5/08* | (2006.01) | |
| *G08G 9/00* | (2006.01) | |
| *H04L 67/12* | (2022.01) | |

(52) U.S. Cl.
CPC .................. *A61B 5/11* (2013.01); *A61B 5/18* (2013.01); *A61B 5/318* (2021.01); *A61B 5/369* (2021.01); *B61L 27/14* (2022.01); *B61L 27/40* (2022.01); *G05D 1/0077* (2013.01); *A61B 5/021* (2013.01); *A61B 5/024* (2013.01); *A61B 5/0816* (2013.01); *B61L 3/127* (2013.01); *G05D 1/0016* (2013.01); *G08G 9/00* (2013.01); *H04L 67/12* (2013.01); *H04L 67/18* (2013.01)

(58) Field of Classification Search
CPC ........... A61B 5/0476; A61B 5/11; A61B 5/18; B61L 27/0022; B61L 27/0077
USPC .......................................................... 701/2
See application file for complete search history.

(56) References Cited

U.S. PATENT DOCUMENTS

| | | | |
|---|---|---|---|
| 6,587,738 B1 | 7/2003 | Belcea | |
| 6,587,764 B2 | 7/2003 | Nickles et al. | |
| 6,832,204 B1 | 12/2004 | Doner | |
| 6,925,425 B2 | 8/2005 | Remboski et al. | |
| 7,188,057 B2 | 3/2007 | Birkelbach et al. | |
| 7,590,485 B2 | 9/2009 | Daum et al. | |
| 7,813,846 B2 | 10/2010 | Wills et al. | |
| 7,937,193 B2 | 5/2011 | Philip et al. | |
| 8,332,086 B2 | 12/2012 | Muinonen et al. | |
| 8,538,611 B2 | 9/2013 | Kumar et al. | |
| 8,577,538 B2 | 11/2013 | Lenser et al. | |
| 8,725,761 B2 | 5/2014 | Rout | |
| 8,862,292 B2 | 10/2014 | Cooper | |
| 8,998,617 B2 | 4/2015 | Kumar | |
| 9,156,477 B2 | 10/2015 | Cooper et al. | |
| 9,327,741 B2 | 5/2016 | Golden et al. | |
| 9,453,735 B2 | 9/2016 | Mathews, Jr. et al. | |
| 9,862,397 B2 | 1/2018 | Meyer et al. | |
| 9,896,115 B2 | 2/2018 | Wills et al. | |
| 9,937,936 B2 | 4/2018 | Brooks et al. | |
| 10,279,825 B2 * | 5/2019 | Kim .................... | B61L 27/0061 |
| 2005/0228620 A1 | 10/2005 | Convert et al. | |
| 2005/0279242 A1 | 12/2005 | Maier et al. | |
| 2007/0219681 A1 | 9/2007 | Kumar et al. | |
| 2009/0045927 A1 | 2/2009 | Atella | |
| 2009/0187291 A1 | 7/2009 | Daum et al. | |
| 2010/0023190 A1 | 1/2010 | Kumar et al. | |
| 2012/0245766 A1 | 9/2012 | Cooper et al. | |
| 2012/0277940 A1 | 11/2012 | Kumar et al. | |
| 2012/0296545 A1 | 11/2012 | Cooper et al. | |
| 2013/0018531 A1 | 1/2013 | Kumar | |
| 2013/0116865 A1 | 5/2013 | Cooper et al. | |
| 2013/0144670 A1 | 6/2013 | Kickbusch | |
| 2013/0171590 A1 | 7/2013 | Kumar | |
| 2013/0190952 A1 | 7/2013 | Severson | |
| 2013/0206862 A1 | 8/2013 | Worden et al. | |
| 2014/0018954 A1 | 1/2014 | Friesen et al. | |
| 2014/0094998 A1 | 4/2014 | Cooper et al. | |
| 2014/0249699 A1 | 9/2014 | Cooper et al. | |
| 2014/0330460 A1 | 11/2014 | Schoonmaker et al. | |
| 2015/0066561 A1 | 3/2015 | Wills et al. | |
| 2015/0168158 A1 | 6/2015 | Mathews, Jr. et al. | |
| 2016/0180721 A1 * | 6/2016 | Otulic ...................... | B60Q 9/00 701/2 |
| 2016/0342933 A1 | 11/2016 | Johnson et al. | |
| 2016/0358475 A1 * | 12/2016 | Prokhorov ........... | G05D 1/0022 |
| 2016/0371788 A1 | 12/2016 | Rackley, III et al. | |
| 2017/0210404 A1 * | 7/2017 | Brooks ................ | B61L 23/007 |
| 2017/0267267 A1 | 9/2017 | Bollapragada et al. | |
| 2017/0282942 A1 * | 10/2017 | Mathews, Jr ........... | B61L 3/008 |
| 2017/0323249 A1 | 11/2017 | Khasis | |
| 2019/0018406 A1 * | 1/2019 | Tudosie ............... | G05D 1/0061 |

FOREIGN PATENT DOCUMENTS

| | | |
|---|---|---|
| WO | 2016191711 A1 | 12/2016 |
| WO | 2018007953 A1 | 1/2018 |

OTHER PUBLICATIONS

Bhuiyan, "Driverless Cars Can Operate in California as Early as April", Recode, Feb. 26, 2018 (4 pages).

Bloom, "DMV to Give Driverless Cars the Green Light", ABC 7 News, KGO-TV San Francisco, Feb. 23, 2018 (7 pages).

Bush, "Shared UAV Enterprise Operator Pooling Framework (SUAVE) Chance Constrained Pooled Fan-out Queueing Analysis", IEEE International Multi-Disciplinary Conference on Cognitive Methods in Situation Awareness and Decision, pp. 21-27, Orlando, Mar. 2015 (31 pages).

Crenshaw, "We Want the US to Lead in Driverless Cars. Here's What Washington Can do to Help.", US Chamber of Commerce, 2018 (5 pages).

Ernst, "Efficient Loading orf Intermodal Container Trains", National Rail Corporation, pp. 124-146, 2001 (23 pages).

Hall, "Phantom Auto Pioneers Remote Driving Technology", Road Show, Mar. 2, 2018 (3 pages).

Harris, "CES 2018: Phantom Auto Demonstrates First Remote Controlled Car on Public Roads", IEEE Spectrum, Newsletter, Jan. 10, 2018 (23 pages).

Lai, "A Computer Vision System for Monitoring the Energy Efficiency of Intermodal Trains", Joint Rail Conference, JRC2006-94047, ASME, pp. 295-304, Atlanta, GA, USA, Apr. 4-6, 2006 (10 pages).

Lai, "A Rolling Horizon Framework for Intermodal Loading Assignment to Improve Fuel Efficiency", Proceedings of 9th International Heavy Haul Railway Conference, Kiruna, Sweden, 2007 (10 pages).

Lebeau, "This Service Wants to Operate Cars with Remote Control When Self-Driving Techs Gets Confused", CNBC, Mar. 20, 2018 (5 pages).

Newcomb, "Why Self-Driving Cars Will Require a 'God View' Eye in the Sky", PCMag, Jan. 21, 2018 (4 pages).

Phantom Auto, "Teleoperation Safety Solution for Autonomous Vehicles", Phantom Auto Webpage, 2018 (5 pages).

Phantom Auto, "Bringing a Human Touch to Autonomous Vehicles", Phantom Auto Webpage, 2018 (7 pages).

Quain, "When Self-Driving Cars Can't Help Themselves, Who Takes the Wheel?", New York Times, Mar. 15, 2018 (4 pages).

Ross, "Human Control of Self-Driving Cars on Policymakers' Radar (Corrected)", The Bureau of National Affairs, Inc., Tech & Telecom on Bloomberg Law, Jan. 11, 2018 (7 pages).

Said, "Look, Ma, No. Driver! Cars Without Humans Coming to California Soon", San Francisco Chronicle, Hearst Newspapers, Hearst Corporation, Feb. 23, 2018 (6 pages).

(56) References Cited

OTHER PUBLICATIONS

Intermodal Pro, "Boost Your Bottom Lime with the Intermodal Terminal Operating System that Does it All", Tideworks Technology, 2011 (2 pages).
Wired, "Self-Driving Cars Have a Secret Weapon: Remote Control" Feb. 1, 2018 (12 pages).
First Examination Report for AU Application No. 2017202698 dated Dec. 9, 2019.

\* cited by examiner

REMOTE VEHICLE OPERATOR ASSIGNMENT SYSTEM

CROSS-REFERENCE TO RELATED APPLICATIONS

This application is a continuation-in-part of U.S. patent application Ser. No. 15/460,431, which was filed on 16 Mar. 2017, and which claims priority to U.S. Provisional Application No. 62/327,101, which was filed on 25 Apr. 2016. This application also is a continuation-in-part of U.S. patent application Ser. No. 15/402,797, which was filed on 10 Jan. 2017. The entire disclosures of these three patent applications are incorporated herein by reference.

FIELD

The subject matter described herein relates to remotely controlling vehicles.

BACKGROUND

Many transportation segments are looking toward remote vehicle operations. For example, the automobile industry, the trucking industry, the rail industry, etc., are moving toward at least partial remote-control of vehicles such as automobiles, trucks, trains, or the like. While some industries may be looking toward self-driving vehicles, these same industries may be looking toward a backup solution where a remotely located operator is able to take control of a vehicle from afar (e.g., due to a system failure or other problem with the self-driving features of the vehicle).

Remote operators can be assigned to remotely control vehicles based on a variety of assignment processes. Many of these known assignment processes, however, are rooted in an analysis of static features or risks to remote operation of the vehicles. These static features or risks can include known risks that do not change with respect to time. But, movement of vehicles and remote-control of vehicles can encounter risks that dynamically change with respect to time. These time-varying risks may not be addressed by the currently known operator assignment processes.

BRIEF DESCRIPTION

In one embodiment, a method includes determining time-variable risk profiles for plural separate vehicle systems that are remotely controlled by operators that are located off-board the separate vehicle systems. The time-variable risk profiles represent one or more risks to travel of the separate vehicle systems during trips of the separate vehicle systems that change with respect to time during the trips of the separate vehicle systems. The method also optionally includes determining an operator staffing demand for the vehicle systems based on the time-variable risk profiles of the separate vehicle systems. The operator staffing demand represents how many of the operators are needed for remotely controlling the separate vehicle systems at different times during the trips and a required qualification of one or more of the operators for remotely controlling the separate vehicle systems at different times during the trips. The method also includes assigning the operators to remotely monitor or control the separate vehicle systems during the trips based on the time-variable risk profiles. Optionally, this assignment also may be based on the operator staffing demand. The operator assigned to one or more of the separate vehicle systems changes with respect to time during the trip of the one or more separate vehicle systems while the one or more separate vehicle systems is moving along one or more routes during the trip.

In one embodiment, a system includes one or more processors configured to determine time-variable risk profiles for plural separate vehicle systems that are remotely controlled by operators that are located off-board the separate vehicle systems. The time-variable risk profiles represent one or more risks to travel of the separate vehicle systems during trips of the separate vehicle systems that change with respect to time during the trips of the separate vehicle systems. The one or more processors also are configured to assign the operators to remotely monitor or control the separate vehicle systems during the trips based on the time-variable risk profiles. The operator assigned to one or more of the separate vehicle systems changes with respect to time during the trip of the one or more separate vehicle systems while the one or more separate vehicle systems is moving along one or more routes during the trip.

In one embodiment, a method includes determining a time-variable risk profile for a vehicle system that is to be one or more of remotely controlled or remotely monitored by one or more operators that are located off-board the vehicle system, and determining an operator staffing demand for the vehicle system based on the time-variable risk profile that is determined. The operator staffing demand represents how many of the operators are needed for one or more of remotely controlling or remotely monitoring the vehicle system. The method also includes assigning at least one of the operators to remotely monitor or control the vehicle system based on the operator staffing demand and the time-variable risk profile. The at least one operator assigned to the vehicle system changes with respect to time during travel of the vehicle system.

BRIEF DESCRIPTION OF THE DRAWINGS

The present inventive subject matter will be better understood from reading the following description of non-limiting embodiments, with reference to the attached drawings, wherein below.

DETAILED DESCRIPTION

Figure 1:
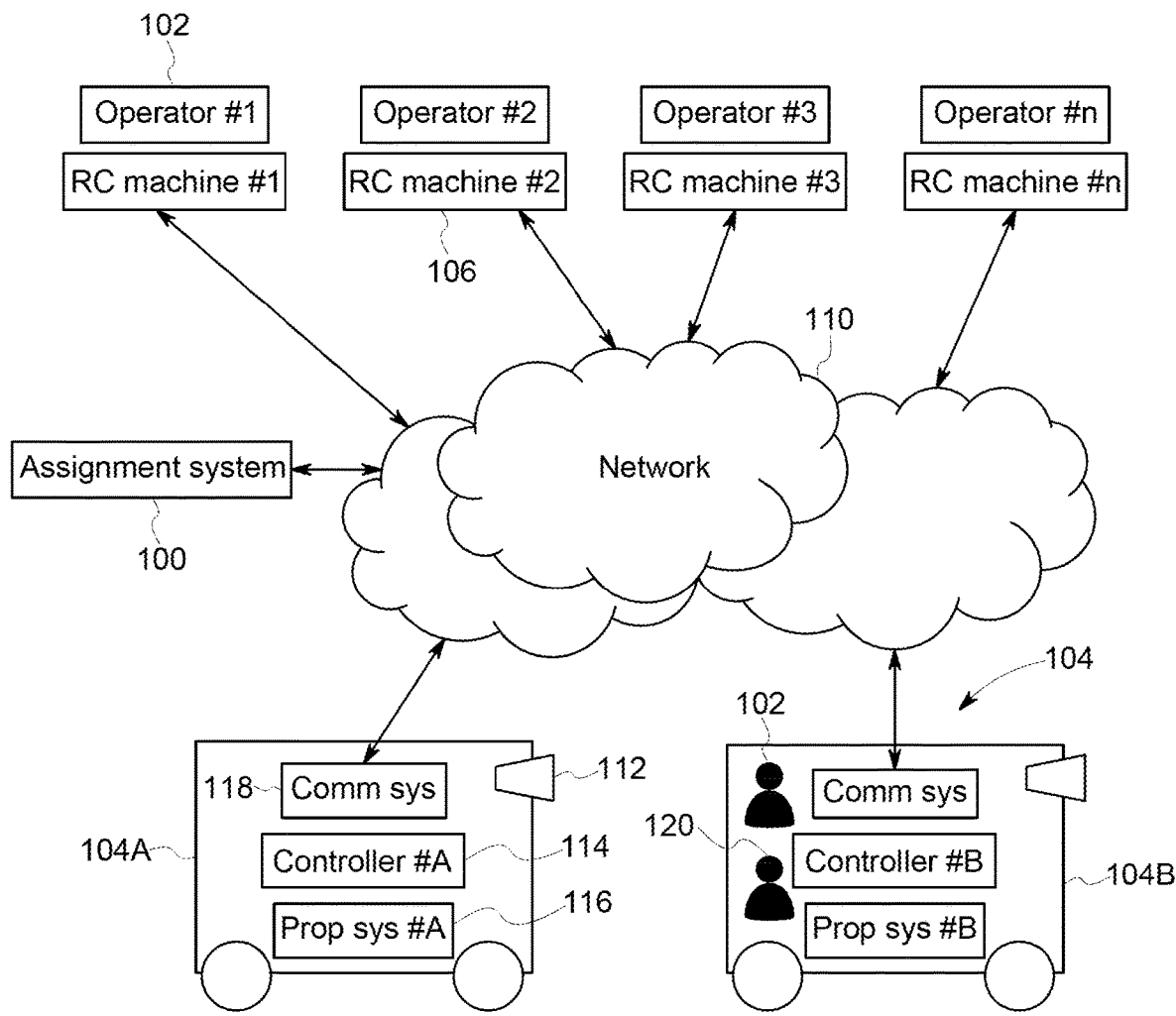
FIG. 1 illustrates one embodiment of a remote vehicle operator assignment system.

The subject matter described herein relates to remote operator assignment systems and methods that examine static and dynamically changing risks to remote-control of vehicles, operator qualifications, operator availability, and the like, and dynamically assign which operators remotely control or monitor the movement of vehicle systems. An operator may remotely control a vehicle when the operator is located off-board the vehicle and controls the movements of the vehicle from afar. In one embodiment, the remote-control of vehicle systems as described herein relates to the remote-control of automobiles, rail vehicles, marine vessels, and the like, and does not extend to the remote-control of toy or model vehicles (e.g., model trains, model cars, model airplanes, remote-control toy boats, etc.). One embodiment of the inventive subject matter described herein relates to assigning operators to remotely control aircraft, such as drones or other aircraft.

At least one embodiment described herein provides an assignment system and method that determine time-varying risk profiles for each vehicle of several vehicle systems traveling within a monitored transportation system. The monitored transportation system can be a portion or the entirety of a network of interconnected routes, such as interconnected roads, tracks, waterways, etc., that is monitored by sensors so that operators can remotely control movement of vehicle systems on the routes. The risk profiles can quantify the amount of risk involved in remotely controlling a vehicle. As described herein, there can be greater risk (and, a larger numerical value assigned for the risk profile) in a vehicle carrying hazardous cargo, a vehicle traveling through a congested area, a vehicle traveling through hazardous weather conditions, or the like, relative to other vehicle systems. The risk may change with respect to time, so the risk profile of a vehicle can change with respect to time. The risk may be estimated based on forecasted or predicted conditions (e.g., weather conditions, traffic conditions, etc.).

The system and method can use the risk profiles of the vehicle systems to determine operator staffing needs for the vehicle systems over time. The operator staffing needs can indicate how many operators are needed at different times to remotely control the vehicle systems (for which the risk profiles were determined), and optionally can indicate specialized operator qualifications that are needed at one or more times for remotely controlling the vehicle systems. The specialized qualifications can be years of operator experience, training classes or sessions completed by the operator, types of licenses obtained by the operators, etc. The qualifications that are needed can change with respect to time. For example, as a remotely controlled vehicle travels through different geographic areas, the risks involved in remotely controlling the vehicle in some areas can significantly increase (thereby potentially necessitating specialized operator training) or decrease (thereby potentially eliminating a need for specialized operator training). As another example, as a remotely controlled vehicle travels through different jurisdictions, different laws and/or regulations can require different operator qualifications for travel in the corresponding areas. The system and method optionally can determine the operator staffing need based on a likelihood of vehicle failure or another emergency situation. This likelihood can be determined or otherwise based on previous travels of vehicle systems in the transportation system, and can increase for larger risk profiles (or decrease for lesser risk profiles).

The system and method can use the operator staffing needs to determine operator staffing levels. The operator staffing levels can be a number of operators needed to be available (e.g., at a facility from which the vehicle systems are remotely controlled) at different upcoming times (e.g., during an upcoming work shift). The operator staffing levels also can indicate a number of operators needed to be available for an upcoming shift that have a specialized qualification, as described above. The system and method can then use the staffed operators to remotely control movements of the vehicle systems during movement in the transportation system. The system and method can select from those operators that are onsite at the facility and assign those operators to different vehicle systems for remotely controlling the vehicle systems. This assignment can be based on a variety of factors, such as the current risk profile for a vehicle (which can indicate that more operators are needed for remotely controlling the vehicle when the risk profile is larger or that fewer operators are needed for remotely controlling the vehicle when the risk profile is smaller), the presence of an operator onboard the vehicle (e.g., fewer remote operators needed when an operator is onboard), the occurrence of an emergency (e.g., accident, such as a collision) or failure of a vehicle or vehicle component (e.g., assign more operators when this occurs), etc. At least one technical effect of the subject matter described herein provides for the efficient assignment and re-assignment of operators to remotely control and/or monitor movement of several different vehicles to ensure the safe and timely concurrent movement of the vehicles.

FIG. 1 illustrates one embodiment of a remote vehicle operator assignment system 100. The assignment system 100 operates to assign different human operators 102 or groups of operators to remotely control movements of vehicle systems 104 (e.g., vehicle systems 104A, 104B in FIG. 1). A vehicle system 104 can be formed of a single vehicle, or can be formed of 2 or more vehicles. With respect to multiple-vehicle systems 104, the vehicle systems 104 can include two or more vehicles that are mechanically or logically coupled together. The vehicles may be mechanically coupled with each other when the vehicles are mechanically coupled by a coupler, for example. With respect to logically coupled vehicle systems, two or more vehicles can be logically connected but not mechanically connected when the vehicles communicate with each other during movement to coordinate the movements of the vehicles with each other and cause the vehicles to move together along one or more routes. While only two vehicle systems 104 are shown in FIG. 1, but the assignment system 100 can assign operators 102 to many more vehicle systems 104 for concurrent remote-control of the vehicle systems 104. The operators 102 are shown in FIG. 1 as Operator #1, Operator #2, and so on. Although only four operators 102 are shown in FIG. 1, the assignment system 100 may assign a much larger number of operators 102 to remotely control the vehicle systems 104 (e.g., up to fifty operators 102, up to one hundred operators 102, etc.). The operators 102 may be onboard and/or off-board the vehicle systems 104, as shown in FIG. 1. In one example, an onboard operator 102 can control movement of the vehicle system 104 in which the operator 102 is located. In another example, the onboard operator 102 can control movement of the vehicle system 104 in which the operator 102 is located and can remotely control movement of a vehicle in the same vehicle system 104 and/or another vehicle system 104 (e.g., if the vehicle system 104 in which the operator 102 is located has multiple propulsion-generating vehicles). In another example, the onboard operator 102 can remotely control movement of another vehicle system 104 in which the operator 102 is not located from the vehicle system 104 in which the operator 102 is located.

The operators 102 use remote-control machines 106 (e.g., "RC Machine #1," and so on, in FIG. 1) to monitor operations of the vehicle systems 104 assigned to the operators 102, and to remotely control the operations of the vehicle systems 104. The machines 106 optionally can be referred to as a control system or remote-control system, or can be included as part of a control system.

The remote-control machines 106 can each represent a stand-alone or shared computing device, such as hardware circuitry that includes and/or is connected with one or more processors (for example, one or more field programmable gate arrays, one or more microprocessors and/or one or more integrated circuits). The processors of the remote-control machines 106 operate to receive input from the operators 102 of the corresponding machines 106, and to generate command messages that are electronically communicated to the vehicle systems 104 via, through, or by way of one or more computerized communication networks 110. The networks 110 can represent networks formed by routers, transceivers, repeaters, modems, satellites, or the like, and allow the remote-control machines 106 to communicate wirelessly with the vehicle systems 104, and can allow for sensors 112 disposed on board and/or offboard the vehicle systems 104 to communicate monitored characteristics of movement of the vehicle systems 104 and/or the routes being traveled on. The sensors 112 can represent cameras, radar systems, temperature sensors, pressure sensors, tachometers, accelerometers, or the like.

The remote-control machines 106 can remotely control movement of the vehicle systems 104 by sending command messages to controllers 114 ("Controller #A" and "Controller #B" in FIG. 1) that are on board the vehicle systems 104. In one embodiment, a single operator 102 may be assigned to remotely control multiple, different (e.g., separate) vehicles 104. For example, a single operator 102 may a machine 106 to remotely control multiple vehicles 104 moving in different directions, at different speeds, in different locations, etc., at the same time. Alternatively, multiple operators 102 may be assigned to control a single vehicle 104 at the same time.

The controllers 114 onboard the vehicle systems 104 can represent hardware circuitry that includes and/or is connected with one or more processors. These processors operate to control movement of the vehicle systems 104. For example, responsive to receiving a command signal from a remote-control machine 106, a controller 114 onboard a vehicle 104 can forward the same command signal or form another command signal that is communicated to a propulsion system 116 ("Prop Sys #A" and "Prop Sys #B" in FIG. 1) onboard the same vehicle 104. The propulsion system represents engines, motors, brakes, or the like of the vehicle systems 104 that operate to start or stop movement of the vehicle systems 104. Communication systems 118 ("Comm Sys" in FIG. 1) onboard the vehicle systems 104 represent communication circuitry that sends and/or receives electronic signals, and is used to communicate with the remote-control machines 106. The communication systems 118 can represent transceivers, modems, routers, or the like.

In one embodiment, the remote-control machines 106 directly control the movement of the vehicles 104 by sending these command signals to the controllers 114. For example, a command signal may be sent to a controller 114 from a machine 106 that automatically changes a throttle setting, of the vehicle, that automatically engages brakes of the vehicle, or that automatically implements some other operational change to the vehicle. Optionally, the remote-control machines 106 can indirectly control the movement of the vehicles 104, such as by sending the command signals to controllers 114 which then then display or otherwise present instructions to any onboard operator (e.g., an operator 102 or another operator) of the vehicle system 104 on how to control the movement of the vehicle 104 from onboard the vehicle system 104 in accordance with the command signal received from a remote-control machine 106.

The assignment system 100 can communicate with the remote-control machines 106 and/or the vehicle systems 104 via the network or networks 110. Alternatively, the assignment system 100 can be formed as part of or shared with one or more of the remote-control machines 106. The assignment system 100 operates to determine time-variable risk profiles for each of several separate vehicle systems 104. The time-variable risk profiles represent one or more risks to travel of the separate vehicle systems 104 during trips of the separate vehicle systems 104 that change with respect to time during the trip to the vehicle systems 104.

Figure 2:
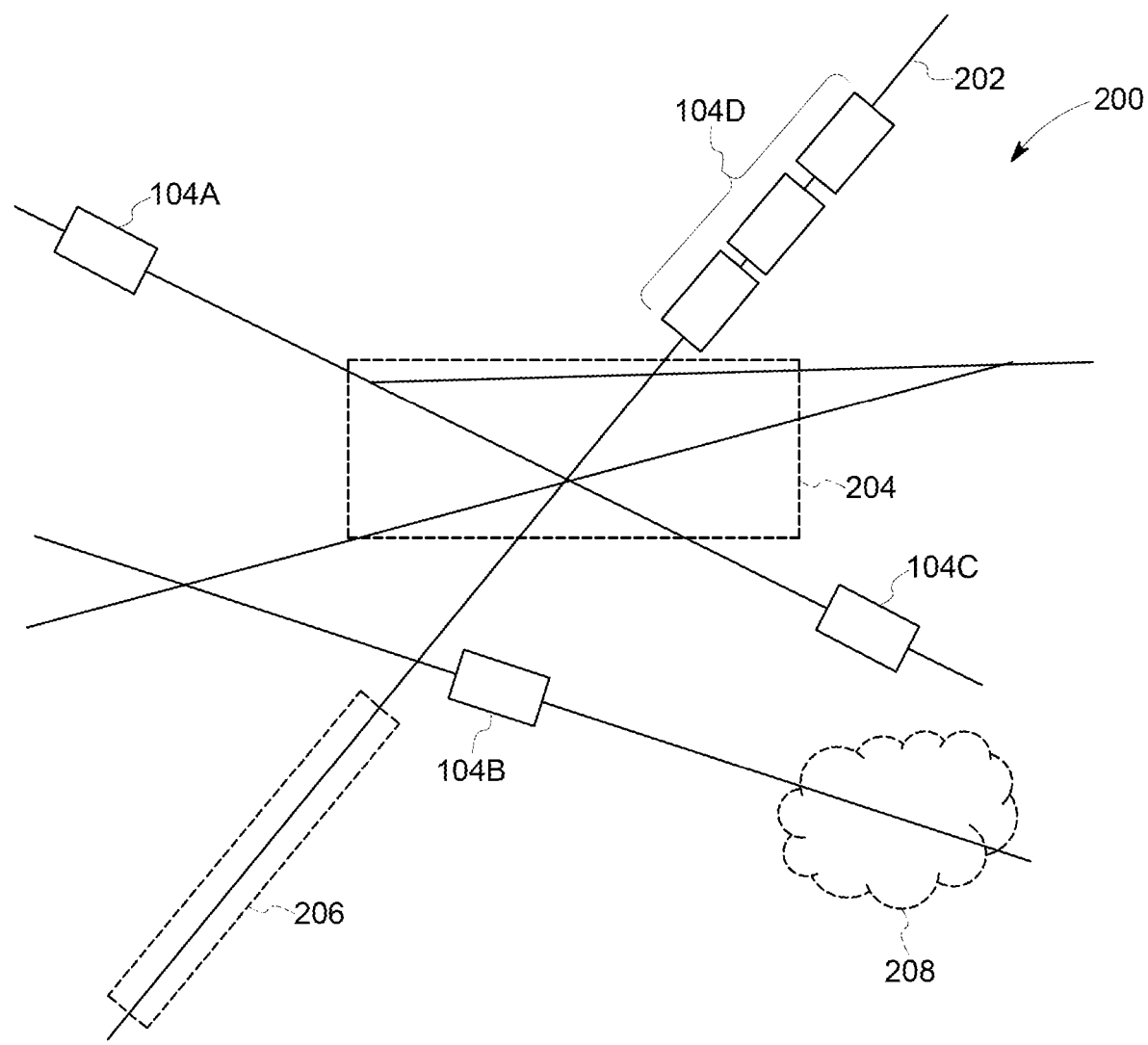
FIG. 2 illustrates one example of a transportation system in which several vehicle systems travel due to the remote-control implemented by remote-control machines shown in FIG. 1.

FIG. 2 illustrates one example of a transportation system 200 in which several of the vehicle systems travel due to the remote-control implemented by the remote-control machines 106 shown in FIG. 1. There are four vehicle systems 104 shown in FIG. 2, and labeled 104A, 104B, 104C, and 104D. The vehicle systems 104 travel on several interconnected routes 202 of the transportation system 200. These routes 202 can represent roads, tracks, waterways, or the like. Several of the remote-control machines 106 can remotely control the movements of the different vehicle systems 104A-D at the same time. The remote-control machines 106 can remotely control the separate movements of these vehicle systems 104, even though the vehicle systems 104 are concurrently traveling on different routes 202, traveling in different directions on the different routes 202, traveling in different directions on the same route 202, traveling in the same direction on different routes 202, and/or traveling toward different locations.

The assignment system 100 can determine the time-variable risk profiles for the separate vehicle systems 104 by identifying one or more time-varying risks and/or one or more static risks to the safe travel of the separate vehicle systems 104. The time-varying risks can represent factors involved in the safe travel of the vehicle systems 104 that change with respect to time. The static risks can represent factors involved in the safe travel of the vehicle systems 104 that do not change with respect to time. The time-varying risks can be different for different locations along the route or routes 202 being traveled by vehicle system 104 during an upcoming trip, and/or can be different at different times or elapsed times during the upcoming trip of the vehicle system 104.

The time-varying risks can include a variety of factors that negatively impact the ability for a vehicle system 104 to otherwise safely travel without incident between the starting location and a destination location for an upcoming trip. As one example, a time-varying risk can include if a vehicle system 104 is to travel through an area having a population density that is greater than a designated threshold. Urban or more heavily populated areas can pose greater risks for the safe travel of the vehicle system 104 through the area due to the increased presence of pedestrians, other vehicle systems, restrictions on how fast the vehicle systems 104 can move, restrictions on the types of cargo that can be carried through the area, or the like. For example, a vehicle system 104 traveling through a heavily populated area may be more likely to be involved in a collision with a pedestrian or other vehicle system than if the same vehicle system travels in a sparsely populated area.

Another example of a time-varying risk includes whether a vehicle system 104 is traveling with a hazardous load. The hazardous load can be cargo that poses a safety threat to those onboard the vehicle system 104 and/or to those offboard the vehicle system 104. Examples of hazardous loads or cargo include radioactive material, corrosive material, flammable material, explosive material, or the like. Vehicle systems 104 caring hazardous loads may be associated with a greater risk profile the vehicle systems 104 that do not carry such a load. Traveling with a hazardous load can be a time-varying risk in that the hazardous cargo may only be carried by the vehicle system 104 for part of an upcoming trip. For example, the vehicle system 104 may stop off at one or more intermediate locations between the starting location at a destination location of the trip to pick up and subsequently drop off hazardous cargo. The risk profile for such a vehicle system 104 may increase while the hazardous cargo is being carried by the vehicle system 104, and may decrease after the hazardous cargo is dropped off.

Another example of a time-varying risk includes a forecasted weather condition. Some weather conditions, such as precipitation, high winds, or the like, can increase the risk of an accident or operational failure of certain vehicle systems 104. For example, vehicles traveling in icy or snowy conditions may have an increased risk profile relative to vehicle systems 104 traveling in dry and warmer conditions. As another example, vehicles systems 104 traveling through areas having strong side winds (winds that are not with or directly against the direction of travel, but closer to perpendicular to a direction of travel) may have a greater risk profile during travel through those winds then during other times.

Another example of a time-varying risk is a hazardous section of a route 202. Some sections of the routes 202 may include steep grades, sharp curves, undulating surfaces, and the like. These route features can increase the inter-car forces between vehicles in multi-vehicle systems 104, and therefore can increase the risk of a vehicle system 104 breaking apart or moving off the route 202.

Another example of a time-varying risk is a geographic area having vehicular traffic congestion. Some sections of the transportation system formed of the routes 202 can have many vehicle systems concurrently traveling on sections of routes 202 that are near each other during certain times of the day. The presence or predicted presence of more than a designated number of vehicle systems 104 per unit area can indicate traffic congestion, and can increase the risk profile of a vehicle system 104 traveling toward or through that area.

Another example of a time-varying risk is a section of a route 202 that is under maintenance. A route 202 that is under maintenance can pose a greater risk to safe travel due to the presence of maintenance personnel, equipment, and the like, on or near the route 202.

With respect to the static risks that make up the risk profiles, one example is a type of cargo carried by a vehicle system 104. As described above, the presence of hazardous cargo being carried by a vehicle system 104 can increase the risk profile for that vehicle system 104. While the hazardous cargo may be a time-varying risk, this cargo also can be a static risk when the cargo is carried by the vehicle system 104 for an entire trip. Another example of a static risk includes a size of a vehicle system 104. The size of vehicle system can represent the length, weight, number of vehicles, or the like, in the vehicle system 104. Longer vehicle systems, vehicle systems that are heavier, and/or vehicle systems 104 formed of many more vehicles, can be associated with greater static risks than vehicle systems that are shorter, lighter, and/or vehicles.

A static risk also can be the presence (or absence) of an operator onboard the vehicle system 104 and/or their experience, qualifications, and performance history. Some vehicles systems 104 may have a human operator travel on the vehicle system 104. The presence of the onboard operator 102 can reduce the risk profile for that vehicle system 104 due to the onboard operator being available to correct any incorrect actions directed by the remote-control machine 106, to quickly respond to emergency or failure situations, or the like. Conversely, vehicle systems 104 having no onboard operator may be associated with greater risk profiles.

With respect to the example of the transportation system 200 shown in FIG. 2, the transportation system 200 is shown as including a densely populated geographic area 204 which one or more of the vehicle systems 104A, 104B, 104D may be traveling toward. This densely populated area 204 can represent the boundaries of a city or town, or can represent another geo-fence around a geographic area where the population exceeds one or more designated thresholds.

Optionally, the geographic area 204 can represent an area of increased vehicular traffic. For example, the area 204 can represent portions of the routes 202 having a number of vehicle systems that exceed sum designated threshold. Stated differently, the area 204 can represent an area having congested vehicular traffic through which travel of one or more additional vehicle systems 104 may be associated with increased risk. The assignment system 100 can determine where the geographic area 204 is located based on a designated boundary (for example, the boundaries of the city), based on an operator-set boundary (for example, the boundaries of an area where increased population is known or believed to be located), or based on monitored traffic patterns. For example, global positioning system receivers disposed onboard vehicles 104, traffic cameras, or other sensors, can monitor how many vehicles systems 104 are in the area 204. If the number of vehicle systems 104 within the area 204 is too large, if the moving speed of the vehicle systems 104 in the areas begins to slow or is slower than a designated speed, etc., the assignment system 100 can determine that the geographic area 204 is associated with traffic congestion.

The increase in the risk profile due to traffic congestion may be a time-varying risk that is predicted based on past traffic patterns. For example, if it has been learned that the area 204 is associated with heavy traffic during certain periods of the day (for example, during morning or evening rush hour), then the time varying risk profile for a vehicle system 104 that is scheduled or expected to travel through the area 204 during one or more these periods of the day may exhibit greater risk than for vehicle systems that do not travel through that area 204 or the vehicle systems that travel through the area 204 at a time that increased traffic is not predicted.

The transportation system 200 also is shown with a designated hazardous terrain area 206. This area 206 can represent the portion of a route 202 having hazardous route conditions. Hazardous route conditions can include steep grades, sharp curves, undulating portions of a route 202, or the like. Optionally, hazardous route conditions can include maintenance or repair of the segment of the route 202 due at least in part to the presence of personnel on or near the repaired section of the route 202. Travel of the vehicle system 104 through the area 206 can be associated with an increased risk profile during travel of the vehicle system 104 through the area 206.

Also shown in FIG. 2 is a forecasted weather area 208. The weather area 208 can represent the geographic area through which one or more routes 202 extend, and that is associated with poor or hazardous weather conditions. A forecasted hazardous weather condition can include a prediction that the weather in the area 208 will be detrimental to travel during one or more times the vehicle system 104 is scheduled or otherwise expected to travel through the area 208. For example, the area 208 can represent locations where the weather is forecasted to include precipitation, elevated temperatures, strong side winds, or other hazardous conditions. Because the weather conditions may change with respect to time, the forecasted weather area 208 may be associated with the time-varying risk. Alternatively, if a predicted weather pattern is not expected to change for extended period of time, then the forecasted weather area 208 can be a static risk to travel of vehicle systems 104.

In one embodiment, the same weather condition may be a hazardous condition that increases the risk profile of a vehicle but may not be a hazardous condition that increases the risk profile of another vehicle. Stated differently, vehicles may have different changes to the risk profiles for the same weather condition depending on parameters or characteristics of the vehicles. Vehicles that are taller (e.g., extend greater heights above the route or surface being traveled upon), vehicles having centers of gravity that are farther above the route or surface, vehicles that are lighter, etc., may have greater risks during travel through areas of increased wind speed. For example, empty coal cars in trains may be more susceptible to tipping over or derailment during travel in windy areas (when compared with full coal cars).

Figure 3:
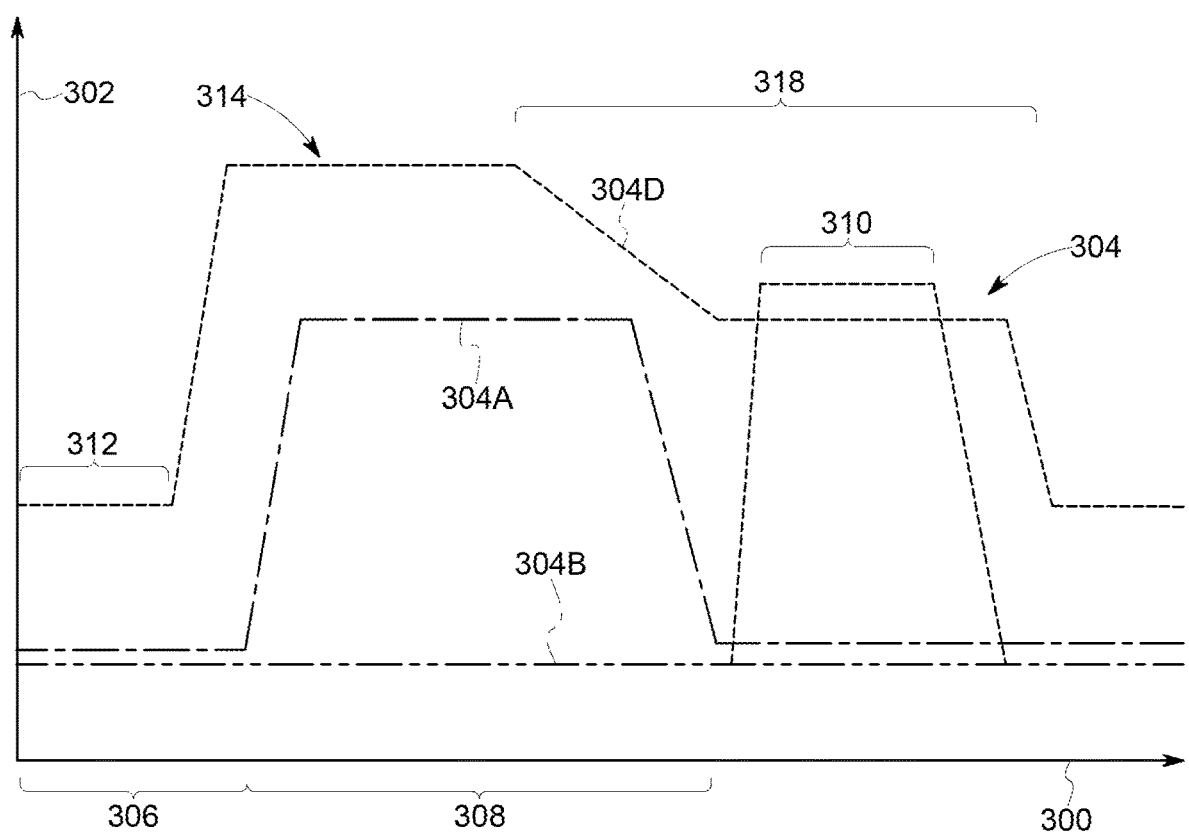
FIG. 3 illustrates examples of time-varying risk profiles for upcoming trips of different vehicle systems shown in FIG. 1.

FIG. 3 illustrates examples of time-varying risk profiles 304 (e.g., risk profiles 304A, 304B, 304D) for upcoming trips of different vehicle systems 104 (e.g., vehicle systems 104A, 104B, 104D). The risk profile 304A represents the quantified risks for the upcoming trip of the vehicle system 104A along the route 202 shown in FIG. 2, the risk profile 304B represents the quantified risks for the upcoming trip of the vehicle system 104B along another route 202 shown in FIG. 2, and the risk profile 304D represents the quantified risks for the upcoming trip of the vehicle system 104D along another route 202 shown in FIG. 2. The risk profiles 304 are shown alongside a horizontal axis 300 that represents time or distance along an upcoming trip. The risk profiles 304 also are shown alongside a vertical axis 302 that represents quantified risks during the trip.

The assignment system 100 can quantify risks by assigning numerical values to different vehicle systems 104 based on the time-varying and/or static risks associated with each vehicle system 104 at different times or locations for the upcoming trip. The values assigned to the different risks can be set by an operator of the assignment system 100 or can have default values. Increased values can be assigned to greater risks, with larger risks associated with increased likelihoods of vehicle accidents, failures, etc. For example, a vehicle system 104 having a total weight above an upper designated threshold can be assigned a risk value of ten. If the vehicle system 104 has a total weight that is less than the upper threshold, but above a lower threshold, then the risk value may be reduced to eight. If the vehicle system 104 also travels over a dangerous section of the routes 202, then the risk value for the vehicle system 104 can increase in the risk profile by fifteen while the vehicle system 104 travels over the dangerous route section. If the vehicle system 104 does not travel through a heavily populated area, then the risk may not be increased (or may be reduced, such as by a value of five). These numbers are provided merely as some examples, and other values may be used.

For example, the risk profile 304A shows a relatively low risk for a first portion 306 of the trip of the vehicle system 104A. This low risk is due to the fact that the vehicle system 104A is formed from a single vehicle (with multiple vehicle systems being assigned greater risk), the vehicle system 104A is not carrying hazardous cargo, the vehicle system 104A is not traveling in a dangerous portion of the route 202, the vehicle system 104A is traveling in a rural (e.g., sparsely populated area), and the vehicle system 104A is light (e.g., is not carrying a large load). During a subsequent portion 308 of the trip, the vehicle system 104A is traveling through the area 204 where there is significantly more population. This change increases the risk to the vehicle system 104A during travel through the heavily populated area 204, as shown in FIG. 3. Upon exiting the heavily populated area 204, the risk represented by the risk profile 304A decreases again due to the exit from the heavily populated area 204.

The risk profile 304B shows a relatively low risk for the entire trip of the vehicle system 104B. This low risk may be due to the vehicle system 104B being formed of a single, light vehicle that is not carrying any hazardous or heavy cargo. Additionally, the vehicle system 104B does not travel through any heavily populated areas 204 or dangerous portions 206 of the routes 202. But, the risk profile 304B of the vehicle system 104B may be modified to show an increased risk 310. This increased risk 310 can represent a change in the weather forecast that shows a high probability (e.g., greater than 70%) that the vehicle system 104B will travel through the area 208 of bad weather shown in FIG. 2. After the vehicle system 104B is expected to exit the area 208 of bad weather, the risk profile 304B decreases to indicate the reduced risk due to the vehicle system 104B no longer traveling through the bad weather.

The risk profile 304D shows a greater risk for the vehicle system 104D during an initial portion 312 of a trip than the risk for the initial portions of the trips of the vehicle systems 104A, 104B. This is due to the vehicle system 104D being longer, having more vehicles in the vehicle system 104D, and potentially due to the vehicle system 104D being heavier than the vehicle systems 104A, 104B. The risk profile 304D increases to an upper level 314 due to passage of the vehicle system 104D through the heavily populated area 204 shown in FIG. 2 before slightly decreasing (due to the exit from the heavily populated area 204). The risk profile 304D then remains slightly elevated in a subsequent portion 318 of the trip (relative to the initial portion 312 of the trip) due to the vehicle system 104D traveling through the area 206 where the route 202 may include many curves, steep grades, maintenance crews, or the like. The risk profile 304D then decreases to the initial risk level upon the vehicle system 104D exiting the area 206.

The assignment system 100 can then determine an operator staffing demand for the upcoming trips of the vehicle systems 104 based on the time-variable risk profiles 304 of the separate vehicle systems 104. The operator staffing demand can be a number that represents how many operators 102 will be needed to remotely control and/or monitor the vehicle systems 104, with the number being based on the risk profiles 304 of the vehicle systems 104. The operator staffing demand can be expressed as a number that changes with respect to time to reflect that the risk profiles 304 of one or more vehicle systems 104 changes with respect to time. The operator staffing demand can be a number that represents a ratio of vehicle systems 104 that are assigned to the operators 102 to remote monitoring and/or controlling of the vehicle systems 104. For example, a ratio of two can indicate that a single operator 102 may be assigned to remotely control and/or monitor two different and separate vehicle systems 104 (that are traveling at the same time, but on different routes, at different speeds, in different directions, to different locations, and/or from different locations).

The assignment system 100 can determine that more operators may be needed to remotely control movement of a vehicle system 104 during time periods that the risk profile 304 of the vehicle system 104 is larger, and that fewer operators may be needed during other time periods when the risk profile 304 is smaller. For example, the greater risk profile 304D of the vehicle system 104D may result in the assignment system 100 determining that an operator 102 should be assigned to remotely control (and monitor) fewer vehicle systems (including the vehicle system 104D) during the entire trip of the vehicle system 104D, while another operator 102 that is assigned to remotely control each of the vehicle systems 104A, 104B can be assigned additional or more vehicle systems during the entire trips of the vehicle systems 104A, 104B due to the lower risk profiles 304A, 304B of the vehicle systems 104A, 104B.

The determination of how many vehicle systems 104 can be assigned to an operator 102 (or how many vehicle systems 104 that an operator 102 can be assigned to) may not be a static number. The assignment system 100 can vary the number of vehicle systems 104 that can be assigned to an operator 102 based on increases (or decreases) in the risk profiles 304. For example, while the assignment system 100 may determine that more vehicle systems 104 (including the vehicle system 104B) can be assigned to the same operator 102 due to the relatively low risk profile 304B of the vehicle system 104B for the duration of the planned upcoming trip. The increased risk during the portion 306 in the risk profile 304B due to the weather area 208 may cause the assignment system 100 to reduce the number of vehicle systems 104 assigned to the operator 102 that also is remotely controlling the vehicle system 104B during travel of the vehicle system 104B in the area 208. As another example, the assignment system 100 may determine that the number of vehicle systems 104 assigned to the operator 102 that is controlling the vehicle system 104D may be increased during travel outside of the heavily populated area 204 and the area 206 due to the decreased risk at these locations or times, but that fewer vehicle systems 104 may be assigned to the operator 102 that is remotely controlling the vehicle system 104D while the vehicle system 104D travels through the areas 206, 208 associated with the increased risks.

In one embodiment, the assignment system 100 can determine how many vehicle systems 104 can be assigned to the same operator 102 by examining the risk profiles 304 of the vehicle systems 104. For example, the assignment system 100 may determine a risk threshold for an operator 102 that is based on the expertise of the operator 102, the training of the operator 102, the continuous hours that the operator 102 has been working, and the like. Greater expertise, more training, and fewer continuous working hours can be associated with greater thresholds for the operator 102, indicating that better trained, experienced, and rested operators 102 may be able to remotely control more vehicle systems 104 at the same time than an operator 102 with less experience, less training, and/or who may be fatigued. The risk values represented by the vehicle systems 104 at different times can be added together, and only those vehicle systems 104 having a sum total of risk values that do not exceed the threshold of the operator 102 may be assigned to that operator 102. Different combinations of the vehicle systems 104 for the operator 102 may be examined.

The assignment system 100 also can determine how many operators 102 are needed for remote-control of vehicle systems 104 based on the operational duties to be performed by the operators 102. Some operators 102 may be assigned to a vehicle system 104 to monitor movement and/or other operations of the vehicle systems 104, but not to control a throttle and/or brake of the vehicle systems 104. These operators 102 may remotely monitor the vehicle system 104 to determine if an emergency, accident, or failure is occurring or about to occur (or that other unsafe or unexpected conditions arise), and then takeover or assist with controlling movement of the vehicle system 104 responsive to determining that the emergency, accident, or failure is occurring or about to occur. Other operators 102 may be assigned to a vehicle system 104 to remotely control (and monitor) movement and/or other operations of the vehicle systems 104. The machines 106 may modify the features, data, and inputs available to operators 102 based on the assignment goal (monitor or control). Because the mental attentiveness needed from an operator 102 to remotely control movement of a vehicle system 104 is greater than the mental attentiveness needed to remotely monitor movement of a vehicle system 104 (but not control), the assignment system 100 can determine that fewer operators 102 are needed for vehicle systems 104 that are being monitored, but not remotely controlled (and that more operators 102 are needed for vehicle systems 104 that are remotely controlled). As a result, the assignment system 100 can assign more vehicle systems 104 to operators 102 that are remotely monitoring more vehicle systems 104 (than other operators 102), while fewer vehicle systems 104 are assigned to operators 102 that are remotely controlling more vehicle systems 104 (than other operators 102).

The operator staffing demand that is determined by the assignment system 100 also can be based on whether any trips of the vehicle systems 104 require operators 102 to have specialized qualifications. For example, the assignment system 100 may determine that vehicle systems 104 having large risk profiles 304 may require operators 102 having at least a designated number of years' experience in remotely controlling vehicle systems 104. The assignment system 100 can determine that trips of vehicle system 104 that extend through certain geographic areas (e.g., with difficult terrain such as the area 206, with dense populations such as the area 204, etc.) may require operators 102 having experience in remotely controlling vehicle systems 104 through those types of areas. The assignment system 100 can determine that vehicle systems 104 carrying heavy and/or hazardous cargo may require operators 102 having specialized training in remotely controlling such vehicle systems 104. The assignment system 100 can determine that trips of vehicle system 104 that extend through certain geographic areas having different or restrictive laws or regulations may require operators 102 having experience in remotely controlling vehicle systems 104 through those types of areas, having specialized training, and/or having specialized licenses. For example, some areas may have laws requiring that a remote operator 102 have a certain license issued by a governmental body or agency. The assignment system 100 can determine that the vehicle system 104 have at least one operator 102 having the required experience, expertise, licensing, etc., for a trip of the vehicle system 104 that passes through any such areas.

The operator staffing demand that is determined by the assignment system 100 can represent a number of operators 102 that are needed to be available (e.g., onsite at a facility where the machines 106 are located) for remotely controlling and/or monitoring the vehicle systems 104 at different times. Because the risk profiles 304 of the vehicle systems 104 change with respect to time, the number of operators 102 needed for remote-control and/or monitoring of the vehicle systems 104 also can change with respect to time.

The assignment system 100 can then assign operators 102 to remotely monitor and/or control the vehicle systems 104 based on the operator staffing demand and the time-variable risk profiles 304 of the vehicle systems 104. While the determination of the operator staffing need involves the assignment system 100 determining how many operators 102 are needed (and, optionally, whether any operators 102 having specialized qualifications are needed), the assignment of operators 102 to vehicle systems 104 can involve the assignment system 100 selecting individual operators 102 to remotely monitor and/or control certain vehicle systems 104.

The assignment of operators 102 can involve the assignment system 100 sending control signals to the machines 106 of the operators 102 assigned to different vehicle systems 104. This control signal can direct the machines 106 to establish communication with the communication systems 118 of the vehicle systems 104 being monitored and/or controlled. The assignment system 100 optionally can send a control signal to the controllers 114 of the vehicle systems 104 to inform the controllers 114 of which machines 106 will be used to remotely monitor and/or control the corresponding vehicle systems 104. The operators 102 can then monitor movement of the vehicle systems 104 to which the operators 102 are assigned by viewing data obtained by or output from the sensors 112 and/or can then remotely control the movement of the vehicle systems 104 to which the operators 102 are assigned by sending control signals from the machines 106 to the controllers 114, which then control the propulsion systems 116 in accordance with the control signals to implement the remote-control actions by the operators 102.

While the assignment system 100 may assign some operators 102 to some vehicle systems 104 based only on how many operators 102 are needed for each vehicle system 104 (based on the risk profiles 304 of the vehicle systems 104), optionally, the assignment system 100 can assign one or more operators 102 to a vehicle system 104 based on other factors. As one example, the assignment system 100 can assign operators 102 to vehicle systems 104 based on operator qualification levels. Operators 102 that have more experience, that have received more training, that have certain licenses, etc., may be assigned to the vehicle systems 104 having the largest risk profiles 304 (e.g., during times when the risk profiles 304 are larger or largest). Conversely, operators 102 that have less experience, that have received less training, that do not have certain licenses, etc., may be assigned to the vehicle systems 104 having smaller risk profiles 304.

In one example, the assignment system 100 can determine a required qualification level for remotely controlling a vehicle system 104 based on the risk profile 304 of the vehicle system 104. This qualification level can be an operator- or user-defined amount of experience, training, and/or licensure that an operator 102 is required to have before that operator 102 can be assigned to a vehicle system 104 associated with the required qualification level. Vehicle systems 104 having risk profiles 304 that exceed one or more thresholds may have required qualification levels that require an assigned operator 102 to have at least five years' experience (or another length of time) in remotely controlling and/or monitoring the vehicle systems 104 having the elevated risk profiles 304. Other vehicle systems 104 that are planning to travel through a heavily populated area, areas of forecasted bad weather conditions, areas with hazardous routes 202, etc., may have similar qualification level requirements. As another example, a vehicle system 104 transporting hazardous cargo may require that an operator 102 have a certain license. In another example, the required qualification level may change based on the duties to be performed by an operator 102 for a vehicle system 104. For example, a vehicle system 104 needing an operator 102 assigned to remotely monitor data from the sensor 112 onboard the vehicle system 104 (but not control movement of the vehicle system 104) may have a lower required qualification level than another vehicle system 104 needing an operator 102 assigned to remotely control movement of the vehicle system 104.

The assignment system 100 can examine the required qualification level(s) of a vehicle system 104, and can examine the qualification levels of operators 102 that may potentially be assigned to the vehicle system 104. The assignment system 100 may not assign any operators 102 not having qualifications that meet or exceed the required qualification levels for the vehicle system 104. The assignment system 100 can assign an operator 102 that has qualifications that meet or exceed the required qualification levels for the vehicle system 104.

The assignment system 100 can assign multiple operators 102 to the same vehicle system 104 based on a training or experience disparity between the operators 102. For example, the assignment system 100 can examine the qualification levels of multiple operators 102 and assign a more experienced or trained operator 102 and a less experienced or trained operator 102 to the same vehicle system 104. This can permit the less experienced operator 102 to learn from the more experienced operator 102 during remote-control and/or monitoring of the vehicle system 104.

The assignment system 100 can assign operators 102 to vehicle systems 104 based on geographic regions or areas in which the vehicle systems 104 are traveling or will be traveling. Certain operators 102 may have more experience or training in remotely controlling movement of vehicle systems 104 in certain geographic regions. For example, one operator 102 may have more experiencing in remotely controlling vehicle systems 104 traveling through mountainous regions, while another operator 102 may have more experiencing in remotely controlling vehicle systems 104 traveling through heavily populated areas. The assignment system 100 can examine where the vehicle systems 104 will be traveling and can examine whether any operators 102 have experience in controlling vehicle systems 104 in the same geographic area. The assignment system 100 can then assign the operator or operators 102 having experience in the area(s) where a vehicle system 104 will travel to that vehicle system 104.

In one embodiment, the assignment system 100 can determine whether to assign an operator 102 to remotely control movement of a vehicle system 104 based on whether another operator is onboard the vehicle system 104 (during the movement that would be remotely controlled). The assignment system 100 can change the risk profile 304 and/or the qualification level required for the remote operator 102 based on the presence or absence of an onboard operator. For example, the risk profile 304 may decrease and/or the required qualification level may decrease when there is an operator onboard the vehicle system 104 to assist the operator 102 that is remotely controlling movement of the vehicle system 104.

The assignment system 100 can determine which operator(s) 102 to assign to one or more of the vehicle systems 104 based on how long the operator(s) 102 have been working to remotely monitor and/or control the same and/or other vehicle systems 104. For example, some operators 102 may be assigned to more vehicle systems 104 and/or may be assigned for longer periods of time to remotely control and/or monitor the vehicle systems 104. This may due to the expertise and/or training of the operator 102, the low supply of operators 102 to assign, or other factors. The assignment system 100 can track how long an operator 102 has continuously worked in remotely monitoring and/or controlling a vehicle system 104 and, if the operator 102 has continuously worked for longer than a designated threshold (e.g., six hours, a single work shift, or another limit), then the assignment system 100 may not assign that operator 102 to another vehicle system 104. This can help prevent some operators 102 from working too long in remotely controlling and/or monitoring vehicle systems 104, which could run the risk of operator error due to fatigue.

The assignment system 100 can monitor the fatigue or alertness of the operators 102 and/or the onboard operators 102 associated with vehicle systems 104 assigned to the operator 102. For example, the assignment system 100 can include one or more sensors that monitor characteristics of the operators 102 to determine if these characteristics indicate that one or more of the operators 102 is not alert or is becoming fatigued. These sensors can include a camera (and optionally one or more processors) that monitors the gaze of an operator 102 to ensure that the operator's 102 eyes are open, attentive, and focused on the input/output device used by the operator 102 to remotely control and/or monitor the vehicle system(s) 104. The sensors can include an input/output device, such as a touchscreen, electronic display with electronic mouse or keyboard, etc., that provides the operator 102 with interactive questions. The responses to the questions (and/or how quickly the operator 102 responds) can be used by the assignment system 100 to determine if the operator 102 is fatigued or alert. If an operator 102 becomes fatigued or is not alert, then the assignment system 100 can avoid assigning vehicle systems 104 to the operator 102 and/or can re-assign one or more (or all) vehicle systems 104 assigned to that operator 102 to another operator 102.

The assignment system 100 can determine which operators 102 to assign to various vehicle systems 104 based on how many vehicle systems 104 will be remotely controlled and/or monitored by the operator 102. For example, the assignment system 100 can avoid having an operator 102 be assigned to too many vehicle systems 104 by using one or more limits on how many vehicle systems 104 can be remotely monitored and/or controlled by the operator 102. The limit on how many vehicle systems 104 can be assigned to or with the same operator 102 can vary based on the qualifications of the operator 102, the duty of the operator 102, and/or the risk profiles 304 of the vehicle systems 104. For example, operators 102 having more training and/or expertise may be assigned more vehicle systems 104 than operators 102 with less training and/or experience. Operators 102 that will be assigned to monitor the vehicle systems 104 may be assigned to more vehicle systems 104 than operators 102 that are assigned to remotely monitor the vehicle systems 104. Operators 102 that are assigned vehicle systems 104 with lower risk profiles 304 may be assigned more vehicle systems 104 than operators 102 assigned to vehicle systems 104 with larger risk profiles 304.

The assignment system 100 can change which operators 102 are assigned to remotely monitor and/or control a vehicle system 104 during a trip (e.g., while the vehicle system 104 is moving). The assignment system 100 can direct one or more operators 102 to stop remotely monitoring and/or controlling a vehicle system 104 and can direct one or more other operators 102 to begin remotely monitoring and/or controlling the same vehicle system 104. The assignment system 100 can change the operator assignment for a vehicle system 104 responsive to the risk profile 304 for the vehicle system 104 changing. For example, the risk profile 304 of a vehicle system 104 may change after the vehicle system 104 has departed from a starting location for a trip, and before the vehicle system 104 has reached an ending location for the trip. This change may be due to a variety of changing factors, such as a change in weather conditions, a change in traffic congestion, a change in a state of a route 202 (e.g., from no maintenance being performed to maintenance being performed, from a bridge being lowered to allow vehicle systems 104 to pass over the bridge to a bridge being raised to prevent vehicle systems 104 to pass, etc.), detection of an emergency situation, etc. If the risk profile 304 increases (e.g., to or above another, larger threshold), then the assignment system 100 can assign one or more additional operators 102 to remotely monitor and/or control the vehicle system 104 associated with the risk profile 304. If the risk profile 304 decreases (e.g., below the threshold), then the assignment system 100 can remove one or more of the operators 102 already assigned to remotely monitor and/or control the vehicle system 104 associated with the risk profile 304 to either remotely monitor and/or control the vehicle system 104 or to stop remotely monitoring and/or controlling the vehicle system 104.

As one example, if a vehicle system 104 is involved in an accident or the risk profile 304 for that vehicle system 104 becomes too large (e.g., exceeds an upper threshold), then a dedicated expert operator can be assigned to remotely control and/or monitor the vehicle system 104. This operator 102 may have much more experience and/or training than other operators 102, and may be better suited for controlling a vehicle system 104 having very high risk to continued safe travel.

The assignment system 100 can change which operators 102 are assigned to different vehicle systems 104 at different times based on the need for an operator 102 having specialized qualifications. For example, if the vehicle system 104 obtains and carries a hazardous load for a portion of the trip, and there is a need for an operator 102 having training on remotely controlling a vehicle system 104 carrying the hazardous load, then the assignment system 100 can assign such an operator 102 and connect the machine 106 of the operator 102 with the vehicle system 104 while the vehicle system 104 carries the hazardous load.

The assignment system 100 can assign or change an assignment of one or more operators 102 to remotely control and/or monitor a vehicle system 104 responsive to detecting that an emergency situation has occurred. The emergency situation can be a collision or other accident, failure of one or more components of the vehicle system 104, or the like. The controller 114 of the vehicle system 104 can notify the assignment system 100 of the emergency situation. Responsive to detecting the emergency situation, the assignment system 100 can modify the risk profile 304 of the vehicle system 104 and optionally one or more other vehicle systems 104 that are traveling toward the location of the emergency situation. The assignment system 100 can automatically assign one or more additional operators 102 to monitor and/or control the vehicle system 104 involved in the emergency situation, and/or to one or more other vehicle systems 104 traveling near or toward the emergency situation. For example, in the event that a collision or derailment has occurred involving a first vehicle system 104, the assignment system 100 can assign an additional operator 102 to remotely monitor and/or control the first vehicle system 104 and/or a second vehicle system 104 that is traveling toward the location of the collision or derailment.

Optionally, the assignment system 100 may have a restriction on how often a change in operator assignment occurs. The restriction can avoid or prevent an operator 102 from frequently being re-assigned to another vehicle system 104. The assignment system 100 may not change which vehicle system(s) 104 that an operator 102 is assigned to more than a designated number of times per unit time. For example, the assignment system 100 may not change which vehicle system 104 is assigned to an operator 102 if that operator has been assigned or re-assigned to another vehicle system 104 more than three times in the previous hour. Alternatively, the assignment system 100 may permit more or less frequent re-assignments of the operators 102.

The assignment system 100 may have a restriction on when a change in operator assignment occurs. The restriction can prevent a vehicle system 104 from changing which operator 102 is remotely controlling and/or monitoring the vehicle system 104 during times that the vehicle system 104 is moving and/or located in an area having an increased risk profile (e.g., the risk profile exceeds a designated threshold).

As another example, the assignment system 100 may have a restriction that does not allow an operator 102 to be assigned to a vehicle system 104 if the current trip of the vehicle system 104 is not scheduled to end (or is not expected to end based on a current location and speed of the vehicle system 104) before a working shift of the operator 102 ends. For example, the assignment system 100 may not permit operators 102 from remotely monitoring and/or controlling vehicle systems 104 for longer than a continuous period of time (e.g., four hours or another length of time) to reduce the possibility of operator error due to fatigue.

Another example of a restriction of the change of operator assignment includes a limit on how many vehicle systems 104 are re-assigned at the same time. Stated differently, the assignment system 100 can change an assignment of an operator 102 to remotely control and/or monitor vehicle systems 104 only when the operator 102 is being re-assigned to at least a designated number of plural vehicle systems 104. The assignment system 100 may seek to avoid repeatedly (and often) changing the operator assignment for the same vehicle system 104. The assignment system 100 may change the operator assignment for a group of multiple vehicle systems 104, and not change the assignment for smaller groups of vehicle systems 104. For example, the assignment system 100 may only re-assign at least three or more (or another lower limit) vehicle systems 104 to the same operator 102. If less than the lower limit of vehicle systems 104 needs to be re-assigned to that operator 102, the assignment system 100 will either try to assign the vehicle systems 104 to another operator 102, will wait to change the assignment to the operator 102 until there is at least the lower limit of vehicle systems 104 needing to be re-assigned to the operator 102, or will not re-assign the vehicle systems 104 to that operator 102.

The operator 102 can be re-assigned to a group of vehicle systems 104 based on common characteristics between the vehicle systems 104 and/or planned travels of the vehicle systems 104. For example, an operator 102 may be re-assigned to a group of vehicle systems 104 that all travel or are scheduled to travel in a common geographic region. The operator 102 may be assigned to those vehicle systems 104 traveling in the same town, city, county, state, multi-state region (e.g., the southwestern most six states of the continuous states in the United States of America), country, time zone, or the like. If two or more vehicle systems 104 in a first group travel or are scheduled to travel in different regions, then the operator 102 may not be assigned to all of the vehicle systems 104 in the first group. Instead, the operator 102 may be assigned to a different, second group of vehicle systems 104 (which may include one or more, but not all, of the vehicle systems 104 in the first group).

As another example, an operator 102 may be re-assigned to a group of vehicle systems 104 that all carry the same type of cargo. The operator 102 may be assigned to those vehicle systems 104 carrying the same type of hazardous cargo (e.g., all cargo is corrosive, all cargo is radioactive, or the like). Optionally, the operator 102 may be assigned to those vehicle systems 104 carrying the same amount of cargo. For example, in one embodiment, for an operator 102 to be assigned to several vehicle systems 104, the vehicle systems 104 must be carrying the same cargo weight or cargo weight in each vehicle system 104 must be within a designated range (e.g., 10%) of each other.

As another example, an operator 102 may be re-assigned to a group of vehicle systems 104 that all carry or are scheduled to carry the same type of cargo. The operator 102 may be assigned to those vehicle systems 104 carrying the same type of hazardous cargo (e.g., all cargo is corrosive, all cargo is radioactive, or the like). Optionally, the operator 102 may be assigned to those vehicle systems 104 carrying the same amount of cargo. For example, in one embodiment, for an operator 102 to be assigned to several vehicle systems 104, the vehicle systems 104 must be carrying the same cargo weight or cargo weight in each vehicle system 104 must be within a designated range (e.g., 10%) of each other.

As another example, an operator 102 may be re-assigned to a group of vehicle systems 104 that all travel in the same direction. The operator 102 may be assigned to those vehicle systems 104 traveling westward (e.g., more west than north, south, or east), even if on different routes 202. For example, the assignment system 100 can assign the same operator 102 to remotely monitor and/or control several vehicle systems 104 traveling in a westward direction (e.g., a direction that is closer to being directly west than any other direction) in the same state, while another operator 102 several other vehicle systems 104 traveling in a northern direction (e.g., a direction that is closer to being directly north than any other direction) in the same state, and so on.

Optionally, the assignment system 100 can change which operator 102 is assigned to a vehicle system 104 based on a request received from the operator 102. The operators 102 may request a change in vehicle system assignment due to the operator 102 wishing to be assigned to certain vehicle systems 104, due to an emergency involving the operator 102, the operator 102 needing a break, or for a variety of other reasons.

Optionally, a passenger 120 (shown in FIG. 1) can be located onboard a vehicle system 104 with or without an operator 102 onboard the same vehicle system 104. The passenger 120 can provide a request to the assignment system 100 to change which operator 102 is remotely controlling the vehicle system 104. For example, the passenger 120 may become concerned that the onboard or off-board operator 102 that is controlling movement of the vehicle system 104 is placing the passenger 120 in risk. The passenger 120 can request that the assignment system 100 assign more operators 102 to remotely control and/or monitor the vehicle system 104 or that another, different operator 102 be assigned to remotely control and/or monitor the vehicle system 104.

If the assignment system 100 determines that a change in assignment is needed, but that changing the assignment for one or more operators 102 would violate a restriction, then the assignment system 100 can assign one or more other operators 102 to the vehicle system 104, or may not change the assignment of the operator(s) 102 to the vehicle system 104.

Figure 4:
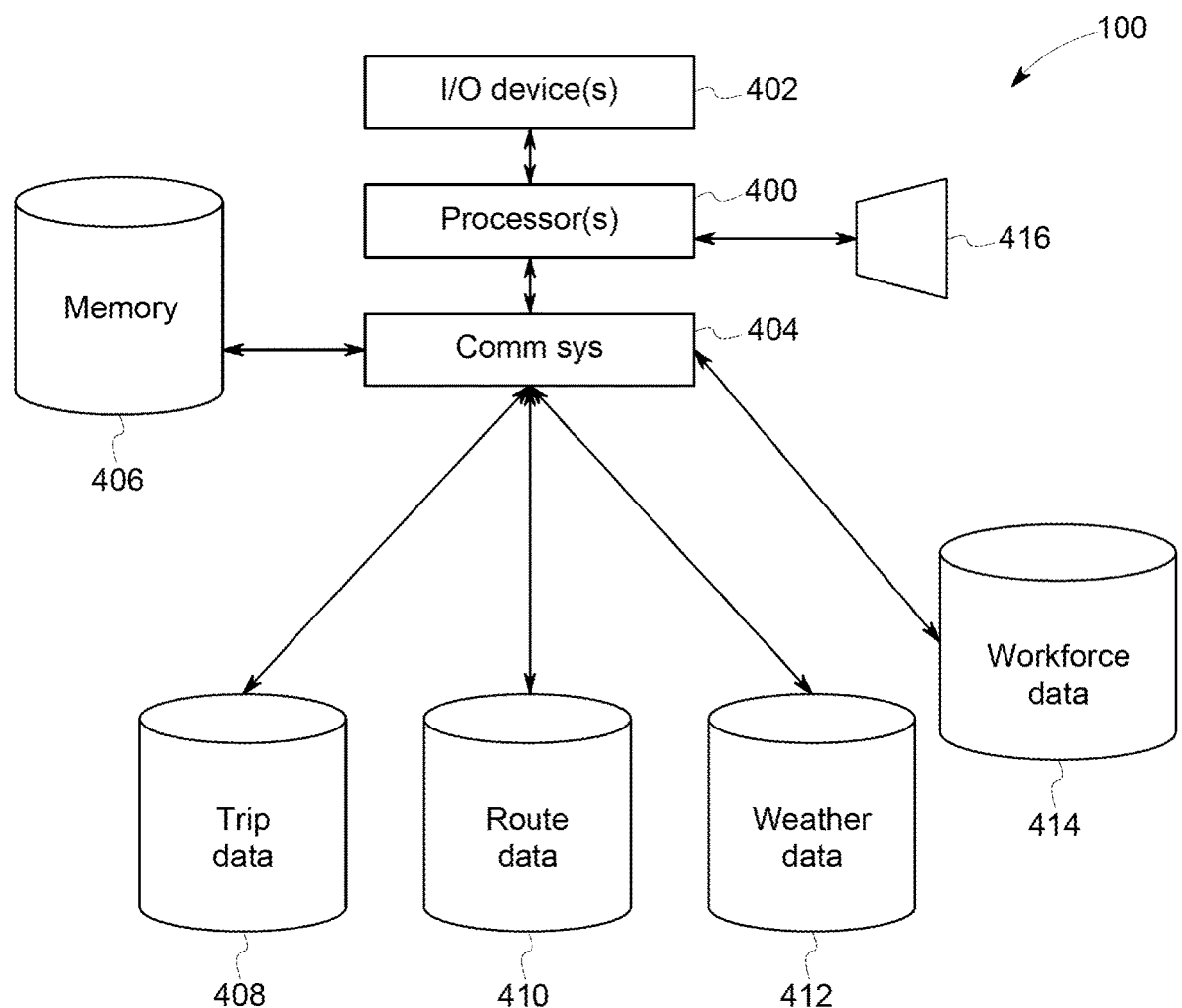
FIG. 4 illustrates one embodiment of the assignment system shown in FIG. 1.

FIG. 4 illustrates one embodiment of the assignment system 100. The assignment system 100 includes one or more processors 400 (e.g., one or more microprocessors, one or more field programmable gate arrays, and/or one or more integrated circuits) that perform the functions that are described herein as being performed by the assignment system 100. The processors 400 can receive input and/or provide output to one or more users of the assignment system 100 via one or more input and/or output devices 402 ("I/O Devices" in FIG. 4). The input/output devices 402 can represent one or more electronic displays, touchscreens, keyboards, electronic mice, styluses, microphones, speakers, etc.

The assignment system 100 includes a communication system 404 that allows the processors 400 to communicate with one or more other systems or devices. The communication system 404 can include one or more transceivers, transmitters, receivers, modems, routers, antennas, or the like, that allow the processors 400 to communicate with the vehicle systems 104 and with one or more memory sources. The memory sources shown in FIG. 4 are provided as one example, and a different combination of memory sources could be used. The memory sources shown in FIG. 4 can represent tangible and non-transitory computer readable media, such as computer hard drives, servers, flash drives, optical discs, etc.

The memory sources can include a local memory 406 that stores information at the assignment system 100, such as which operators 102 are assigned to which vehicle systems 104, which operators 102 are available, operator staffing needs, schedules of the vehicle systems 104, operator qualifications, limits or restrictions on which operators 102 can be assigned to different vehicle systems 104, and the like.

The memory sources can include a trip database 408 that stores trip data. The trip data include information about the cargo carried by different vehicle systems 104, the schedules of the vehicle systems 104, the locations of the vehicle systems 104, and/or identifications of the vehicles in the vehicle systems 104. The processors 400 can obtain at least some of this information to assist with assigning operators 102 to vehicle systems 104, as described above.

The memory sources can include a route database 410 that stores route data. The route data include information about the routes 202 over which the vehicle systems 104 travel or will travel. This information can include identifications of curves in the routes 202, undulations in the routes 202, speed limits of the routes 202, grades in the routes 202, traffic congestion (historical and/or predicted for upcoming times) in different areas, locations of the routes 202, areas of the routes 202 that are under maintenance or other repair, and the like. The memory sources can include a weather database 412 that stores weather data. The weather data include predicted weather forecasts, historical weather conditions, and the like, for one or more areas through which the routes 202 extend.

The memory sources can include a workforce database 414 that stores workforce data. The workforce data include information about the operators 102, such as trainings completed by various operators 102, experiences of the operators 102, restrictions on which vehicle systems 104 can be assigned to some operators 102, special qualifications of operators 102, work hours of the operators 102, indications of how long operators 102 have continuously worked in remotely controlling and/or monitoring vehicle systems 104, and the like.

The assignment system 100 optionally includes one or more sensors 416 that can generate data indicative of how alert or fatigued operators 102 are. The sensors 416 can represent cameras that generate images or videos of the operators 102 (which can be manually and/or automatically inspected to check on operator 102 alertness or fatigue), an input/output device that provides questions, games, or other interactive exercises to test and/or increase the alertness of operators 102, or the like.

Figure 5A:
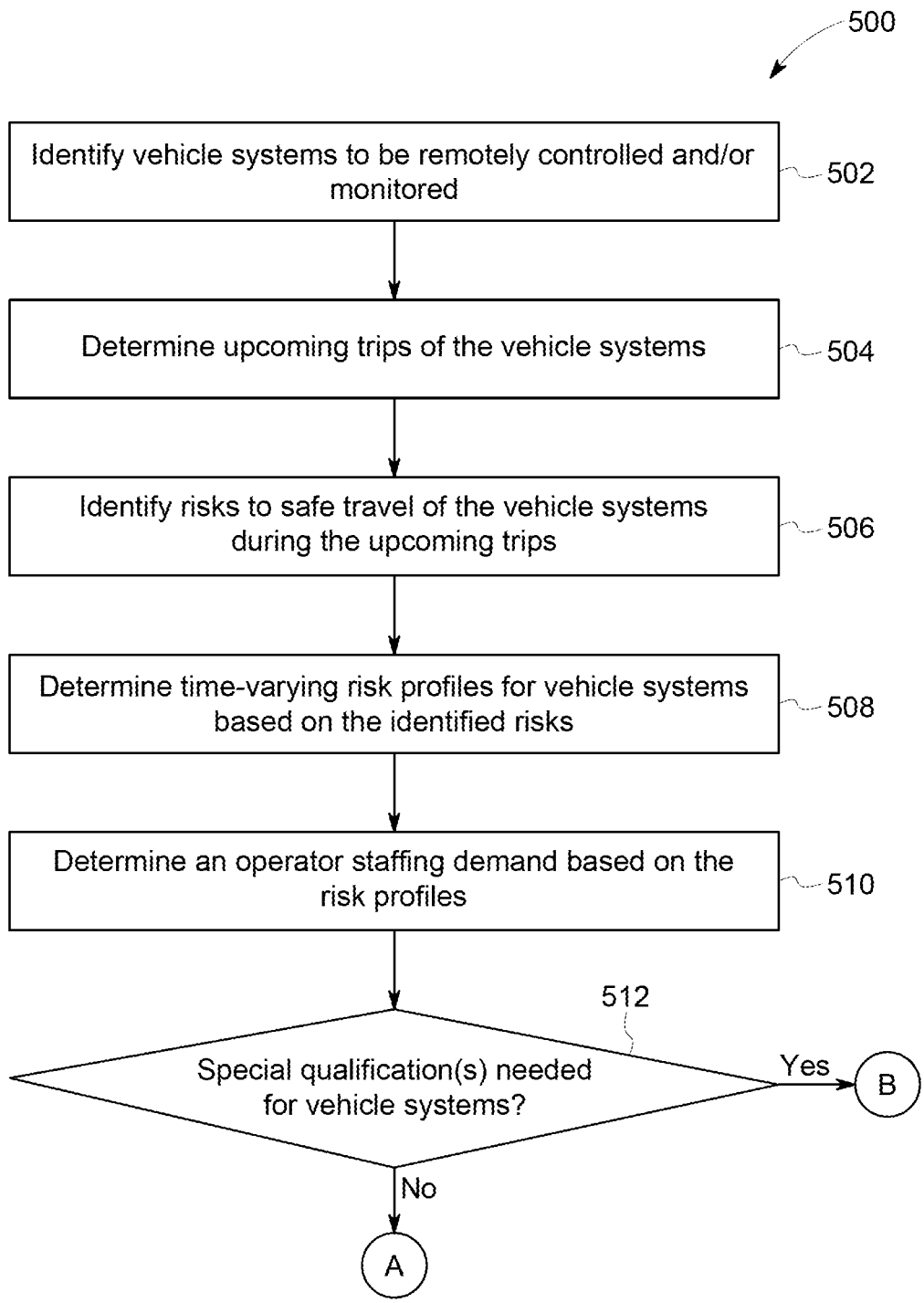
FIGS. 5A through 5C illustrate a flowchart of one embodiment of a method for dynamically assigning operators to remotely control and/or monitor movements of one or more vehicle systems.
Figure 5B:
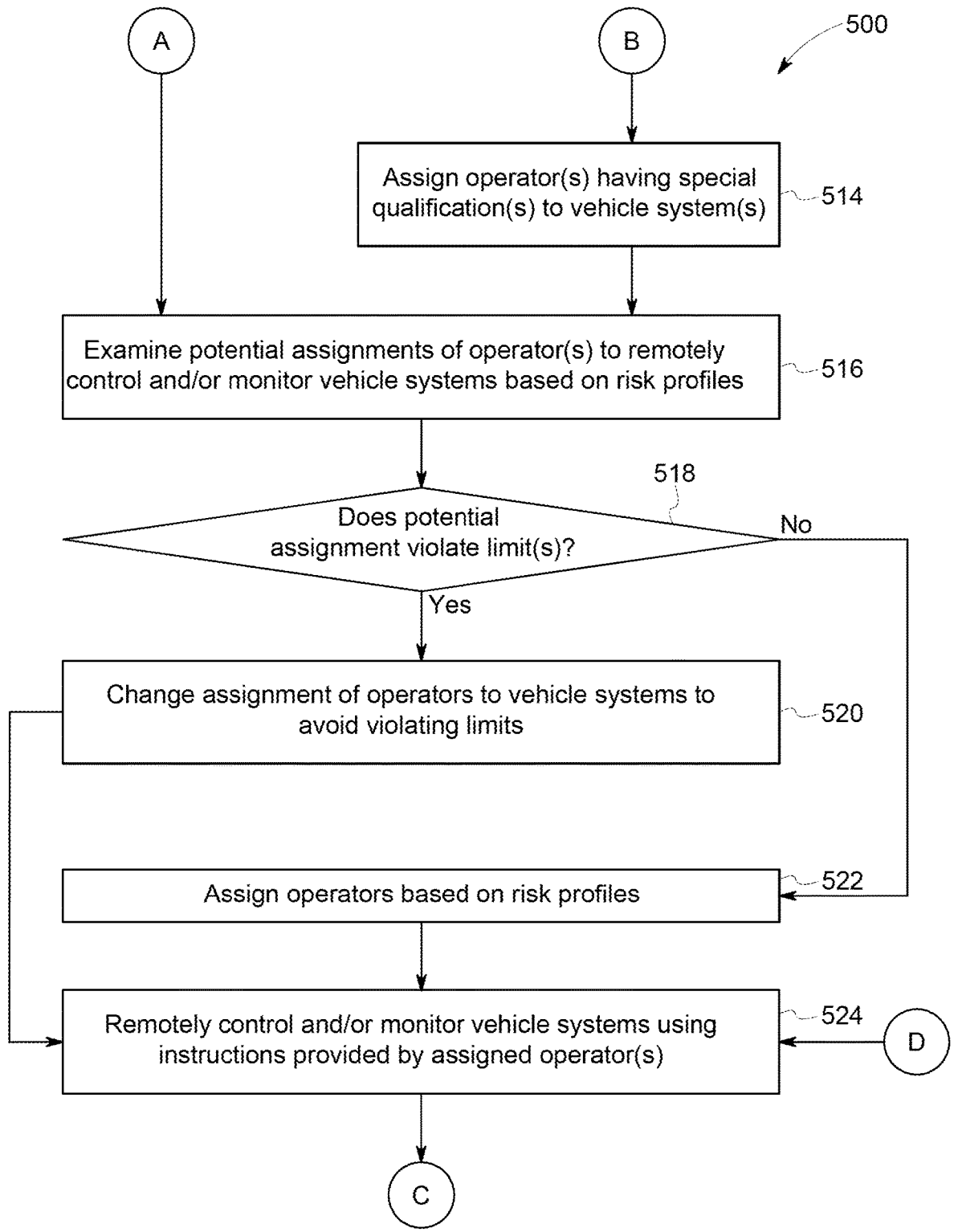
Figure 5C:
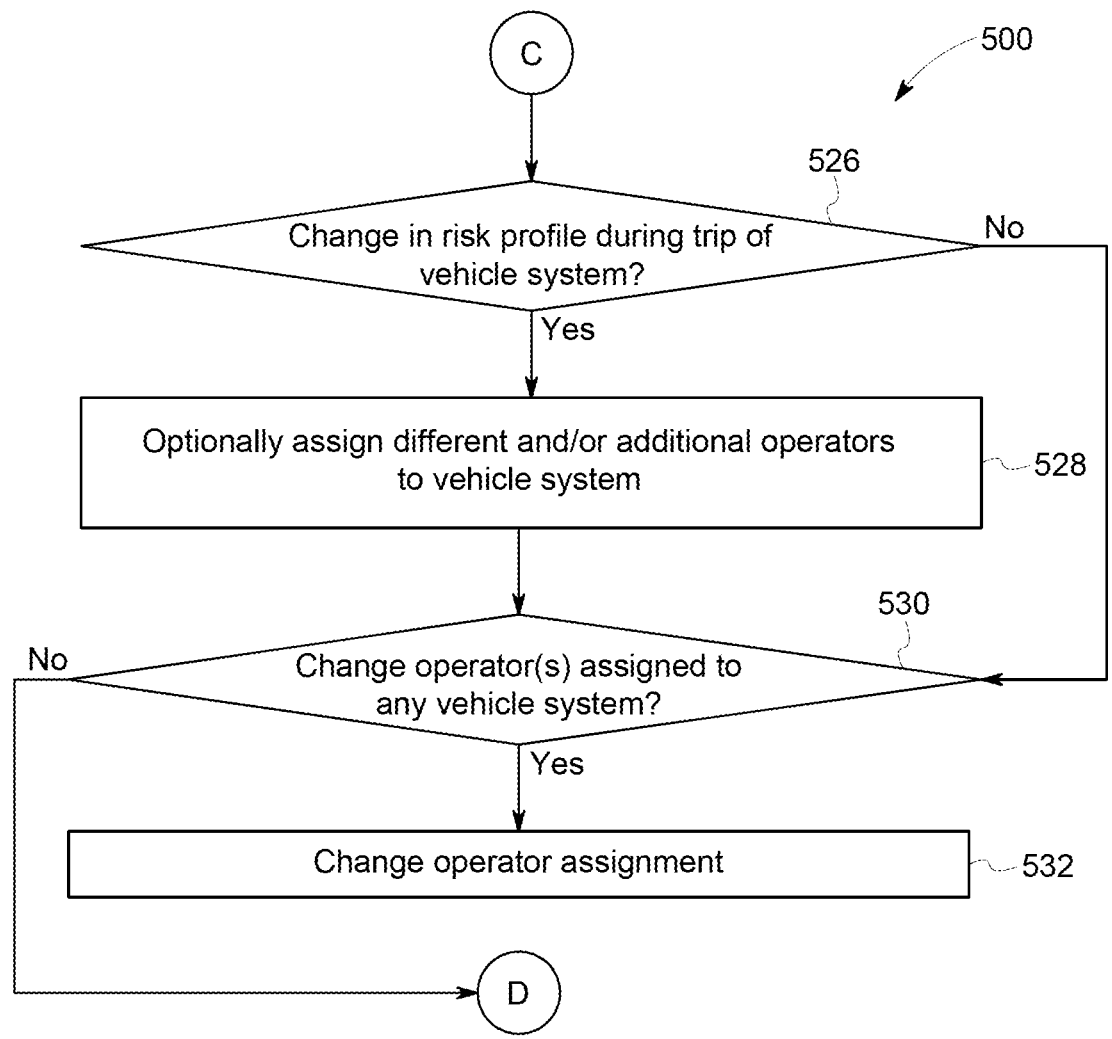

FIGS. 5A through 5C illustrate a flowchart of one embodiment of a method 500 for dynamically assigning operators to remotely control and/or monitor movements of one or more vehicle systems. The method 500 can represent the operations performed by the processors 400 of the assignment system 100 in one embodiment. At 502, vehicle systems 104 that are to be remotely controlled and/or monitored during upcoming trips are identified. These vehicle systems 104 can be identified by determining which vehicle systems 104 are scheduled to depart on the trips within a designated period of time (e.g., one working day), by determining which vehicle systems 104 are associated with a subscription or purchase of a service to remotely control and/or monitor movements of the vehicle systems 104, by examining trip data of the vehicle systems 104, or the like.

At 504, upcoming trips of the vehicle systems 104 are determined. These trips can be determined by examining trip data of the vehicle systems 104. This data can indicate where the vehicle systems 104 are leaving from, where the vehicle systems 104 are traveling, and/or where the vehicle systems 104 are headed toward. Optionally, this information can be provided by an operator onboard a vehicle system 104, or can be obtained from global positioning system data (or other location data) received from a vehicle system 104. For example, the processors 400 can track where a vehicle system 104 is moving based on data received from the vehicle system 104. The upcoming trip for that vehicle system 104 can be routes 202 that the vehicle system 104 is headed toward, even if the trip of the vehicle system 104 has not yet been planned.

At 506, risks to the safe travel of the vehicle systems 104 on the upcoming trips are identified. As described above, these risks can include the transportation of hazardous cargo, travel through hazardous or difficult sections of a route 202, travel through hazardous weather conditions, travel through congested traffic areas, and the like. The risks that are identified can include static risks and/or time-varying risks, also as described above.

At 508, time-varying risk profiles for the vehicle systems are determined based on the identified risks. As described above, these profiles 304 can represent how the risks to safe travel of the vehicle systems 104 increase or decrease over time. At 510, an operator staffing demand is determined based on the risk profiles. The operator staffing demand can be determined by calculating how many operators 102 are needed for remotely controlling and/or monitoring the vehicle systems 104 based on the risk profiles 304 to achieve an overall acceptable risk (e.g., below some total risk threshold). This acceptable risk threshold can vary based on a risk tolerance. For example, larger thresholds can be associated with systems 100 having increased risk tolerances, while smaller thresholds can be associated with systems 100 having reduced risk tolerances. A risk tolerance can depend on a variety of factors, such as an insurance provider's restrictions or limitations on insurable operation of the system 100, on a subscriber's requested risk tolerance, or the like. As described above, increased risk profiles 304 can require more operators 102, while reduced risk profiles 304 may require fewer operators 102.

At 512, a determination is made as to whether one or more vehicle systems require special operator qualifications. This determination can involve determining whether one or more vehicle systems 104 are traveling or will be traveling along hazardous route conditions, are traveling or will be traveling in hazardous weather conditions, are carrying hazardous cargo, and the like, as described above. These conditions may indicate that an operator 102 having specialized qualifications to control and/or monitor the vehicle system 104 may be needed to assign to the vehicle system 104 associated with the risks requiring specialized qualification.

If a vehicle system 104 is associated with a risk requiring a specialized operator qualification, then flow of the method 500 can proceed toward 514. Otherwise, flow of the method 500 can proceed toward 516.

At 514, an operator having a specialized qualification that is required by a vehicle system is assigned to that vehicle system. For example, an operator 102 having specialized training and/or experience in remotely controlling movement of a vehicle system 104 that carries hazardous cargo or that includes a vehicle having specialized handling rules, may be assigned to a vehicle system 104 that is carrying that hazardous cargo or that includes that vehicle, as described above.

At 516, potential assignments of operators to the vehicle systems are examined. These potential assignments can be determined by assigning the operators 102 having specialized qualifications to the vehicle systems 104 requiring such qualifications, and then assigning the remaining operators 102 to the vehicle systems 104 based on the risk profiles 304 of the vehicle systems 104. As described above, more operators 102 may be assigned to the vehicle systems 104 having larger risk profiles 304, while fewer operators 102 may be assigned to the vehicle systems 104 having smaller risk profiles 304. The potential assignments can be examined to determine if the assignments violate any limits.

At 518, a determination is made as to whether the examination of the potential operator assignments indicates that an assignment violates one or more limits. As described above, the processors 400 may limit how many vehicle systems 104 that an operator 102 can be assigned to, may limit which operators 102 can be assigned to a vehicle system 104 based on the qualifications of the operators 102, may limit how long operators 102 can be working to remotely control and/or monitor the vehicle systems 104, etc. The processors 400 can examine the potential assignments and determine if any assignments violate a limit. If an assignment violates a limit, then flow of the method 500 can proceed toward 520. Otherwise, flow of the method 500 can proceed toward 522.

At 520, an assignment of one or more operators to one or more vehicle systems is changed. The operator 102 that was assigned or potentially assigned to a vehicle system 104 in violation of a limit can be re-assigned to another vehicle system 104. The re-assignment of operators 102 may be subject to one or more additional limits, as described herein, such as not re-assigning an operator 102 to often or to too many vehicle systems 104.

At 522, the operators are assigned to the vehicle systems according to the potential assignments. For example, those operator assignments that do not violate the limit(s) can be assigned to the vehicle systems. As described above, this assignment can involve the machine 106 used by the operator 102 establishing a communication link with the vehicle system(s) 104 to which the operator 102 is assigned. Optionally, the operations described in connection with 510 through 522 can be performed in a single integrated operational step by solving a single optimization problem that takes the various factors and constraints described above into account.

At 524, the vehicle systems are remotely controlled and/or monitored using instructions that are sent from the assigned operators. The vehicle systems 104 can change throttle settings, speeds, brake settings, and the like, based on instructions received from the operators 102 who are remotely located. The operators 102 may be remotely located in that the operators 102 are not able to see the vehicle systems 104 being controlled by the operators 102 without the aid of a camera and display showing the images or video generated by the camera.

At 526, a determination is made as to whether the risk profile for one or more of the vehicle systems changes during trips of the vehicle systems. The risk profile 304 for a vehicle system 104 may change for a variety of reasons, such as unknown or unplanned route maintenance, a change in weather conditions, a change in route conditions, a change in traffic congestion, an accident or failure involving the vehicle system 104, and the like. If the risk profile 304 for a vehicle system 104 changes (e.g., increases), then one or more additional operators 102 may need to be assigned to the vehicle system 104 and/or one or more operators 102 having specialized qualifications may need to be assigned to the vehicle system 104. As a result, flow of the method 500 can proceed toward 528. Otherwise, flow of the method 500 can proceed toward 530.

At 528, one or more different and/or additional operators are assigned to the vehicle system. The increased and/or different risk associated with the vehicle system 104 can require that more operators 102 be involved in controlling and/or monitoring the vehicle system 104, and/or that an operator 102 having a specialized qualification control and/or monitor the vehicle system 104. One or more of these additional and/or specially qualified operators 102 can be assigned or re-assigned to the vehicle system 104.

At 530, a determination is made as to whether an operator assignment needs to be changed for any of the vehicle systems. An operator assignment may need to be changed if the operator 102 is working or will end up working longer than a designated limit, if an operator 102 requests a change in assignment, if an operator 102 becomes fatigued, or the like. If an operator assignment requires changing, then flow of the method 500 can proceed toward 532. Otherwise, flow of the method 500 can return toward 524. Alternatively, flow of the method 500 may return to another operation or may terminate.

At 532, one or more different operators are assigned to the vehicle system. For example, if an operator 102 has been working too long in remotely controlling a vehicle system 104, if the operator 102 requests a different assignment to another vehicle system 104, if operator 102 requires a break for some other reason, if the onboard operator 102 or passengers 120 request dedicated assistance which requires a reassignment, and/or the operator 102 has become fatigued, then an additional and/or replacement operator 102 may be assigned to that vehicle system 104. Flow of the method 500 can then return toward 524. Alternatively, flow of the method 500 may return to another operation or may terminate.

In one embodiment, a method includes determining time-variable risk profiles for plural separate vehicle systems that are remotely controlled by operators that are located off-board the separate vehicle systems. The time-variable risk profiles represent one or more risks to travel of the separate vehicle systems during trips of the separate vehicle systems that change with respect to time during the trips of the separate vehicle systems. The method also optionally includes determining an operator staffing demand for the vehicle systems based on the time-variable risk profiles of the separate vehicle systems. The operator staffing demand represents how many of the operators are needed for remotely controlling the separate vehicle systems at different times during the trips and a required qualification of one or more of the operators for remotely controlling the separate vehicle systems at different times during the trips. The method also includes assigning the operators to remotely monitor or control the separate vehicle systems during the trips based on the time-variable risk profiles and, optionally, based on the operator staffing demand. The operator assigned to one or more of the separate vehicle systems changes with respect to time during the trip of the one or more separate vehicle systems while the one or more separate vehicle systems is moving along one or more routes during the trip.

Optionally, the method includes remotely controlling movement of at least one of the separate vehicle systems based on instructions received from at least one of the operators assigned to the at least one of the separate vehicle systems, and/or remotely monitoring operation of at least one of the separate vehicle systems based on instructions received from at least one of the operators assigned to the at least one of the separate vehicle systems.

Optionally, the separate vehicle systems include separate rail vehicle systems.

Optionally, the separate vehicle systems include separate automobiles.

Optionally, the separate vehicle systems include separate trucks.

Optionally, the separate vehicle systems include separate marine vessels.

Optionally, the separate vehicle systems include separate aerial vehicles.

Optionally, the separate vehicle systems include separate unmanned aerial vehicles.

Optionally, the separate vehicle systems include vehicles traveling or scheduled to one or more of travel on different routes, travel in different directions, or travel in different locations.

Optionally, determining the time-variable risk profiles for the separate vehicle systems includes identifying one or more time-varying risks to travel of the separate vehicle systems during movements of the trips that change with respect to location along the trips and/or with respect to elapsed time during the trips.

Optionally, the one or more time-varying risks include one or more of travel of one or more of the separate vehicle systems through an urban area, travel of one or more of the separate vehicle systems through an urban area, travel of one or more of the separate vehicle systems with a hazardous load, or a weather condition that changes with respect to time and through which one or more of the separate vehicle systems is to travel.

Optionally, determining the time-variable risk profiles for the separate vehicle systems includes identifying one or more static risks to travel of the separate vehicle systems during movements of the trips that do not change with respect to location along the trips and/or with respect to elapsed time during the trips.

Optionally, the one or more static risks include one or more of a type of load carried by one or more of the separate vehicle systems, a size of one or more of the separate vehicle systems, a weight of one or more of the vehicle systems, or a presence of an onboard operator on one or more of the separate vehicle systems during the trip of the one or more separate vehicle systems.

Optionally, determining the time-variable risk profiles for the separate vehicle systems includes forecasting a change in one or more characteristics of the trip of one or more of the separate vehicle systems.

Optionally, the change in the one or more characteristics of the trip that is forecasted includes a change in a weather condition through which one or more of the separate vehicle systems is traveling toward, a change in traffic congestion through which one or more of the separate vehicle systems is traveling toward, or a change in service or maintenance performed on one or more routes on which one or more of the separate vehicle systems will travel.

Optionally, the operator staffing demand is determined by decreasing how many of the operators are needed for remotely controlling the separate vehicle systems having reduced risk profiles and increasing how many of the operators are needed for remotely controlling the separate vehicle systems having increased risk profiles.

Optionally, the operator staffing demand is determined by increasing how many of the operators are needed for remotely controlling one or more of the separate vehicle systems responsive to detection of an emergency situation involving the one or more separate vehicle systems.

Optionally, the emergency situation involves an accident involving the one or more separate vehicle systems or a failure of the one or more separate vehicle systems.

Optionally, the method also includes increasing the risk profile associated with the one or more separate vehicle systems responsive to detection of the emergency situation.

Optionally, the operator staffing demand is a number of the operators required to be onsite at a facility from which the separate vehicle systems are remotely controlled.

Optionally, the operator staffing demand is determined as a time-varying number of the operators that are needed for assignment to the separate vehicle systems.

Optionally, the method also includes changing the operator staffing demand as the time-varying risk profile for one or more of the separate vehicle systems changes with respect to time.

Optionally, changing the operator staffing demand includes changing a ratio of the separate vehicle systems to the operators assigned to remotely control the separate vehicle systems.

Optionally, assigning the operators to remotely monitor or control the separate vehicle systems includes communicatively coupling one or more of the separate vehicle systems to one or more of the operators and wirelessly communicating command signals from the one or more operators to the one or more separate vehicle systems for remotely controlling movements of the one or more separate vehicle systems or for remotely monitoring operations of the one or more separate vehicle systems.

Optionally, assigning the operators to remotely control the separate vehicle systems includes changing which of the operators are assigned to remotely control one or more of the separate vehicle systems during movement of the one or more separate vehicle systems during the trip of the one or more separate vehicle systems.

Optionally, assignment of which of the operators is assigned to remotely control one or more of the separate vehicle systems changes based on a change in the risk profile associated with the one or more separate vehicle systems.

Optionally, the method also includes restricting how often an assignment of one or more of the operators to remotely control the separate vehicle systems is changed.

Optionally, changing which of the operators are assigned to remotely control the one or more separate vehicle systems includes reallocating a group of two or more of the vehicle systems to the same operator.

Optionally, assigning the operators to remotely control the separate vehicle systems includes determining a required qualification level for remotely controlling one or more of the separate vehicle systems based on the risk profile of the one or more separate vehicle systems, and examining qualification levels of the operators. The operators can be assigned to the separate vehicle systems based on the qualification levels of the operators and the required qualification level of the one or more separate vehicle systems.

Optionally, one or more of the required qualification level or the qualification levels of the operators includes an amount of operator experience in remotely controlling one or more of the separate vehicles or an amount of training previously completed by the operators.

Optionally, two or more of the operators are assigned to remotely control movement of the same vehicle system based on one or more of a training disparity or an experience disparity between the two or more operators.

Optionally, the operators are assigned to remotely control movement of the separate vehicle systems based on geographic regions in which the separate vehicle systems are traveling or will travel during the trips.

Optionally, the operators are assigned to remotely control movement of the separate vehicle systems based on whether the operators monitor operations of the separate vehicle systems or control movement of the separate vehicle systems.

Optionally, the operators are assigned to remotely control movement of the separate vehicle systems based on whether an onboard operator is present on the separate vehicle systems during the trips.

Optionally, the operators are assigned to remotely control movement of the separate vehicle systems based on whether two or more of the separate vehicle systems assigned to the same operator one or more of travel or are scheduled to travel in a common geographic region, carry a common type of cargo, and/or travel or are scheduled to travel in a common direction.

Optionally, the operators are assigned to remotely control movement of the separate vehicle systems based on how long one or more of the operators has been continuously remotely controlling movement of one or more of the separate vehicle systems.

Optionally, the operators are assigned to remotely control movement of the separate vehicle systems based on a monitored fatigue level of the operators.

Optionally, one or more of the operators are assigned to remotely control movement of one or more of the separate vehicle systems based on how many of the separate vehicle systems are assigned to the same operator.

Optionally, assignment of one or more of the operators to remotely control movement of one or more of the separate vehicle systems changes based on a request to change an assignment received from the one or more operators.

Optionally, assignment of one or more of the operators to remotely control movement of one or more of the separate vehicle systems includes assigning a dedicated expert operator to remotely control the one or more separate vehicle systems responsive to the risk profile of the one or more separate vehicle systems exceeding a designated threshold.

In one embodiment, a system includes one or more processors configured to determine time-variable risk profiles for plural separate vehicle systems that are remotely controlled by operators that are located off-board the separate vehicle systems. The time-variable risk profiles represent one or more risks to travel of the separate vehicle systems during trips of the separate vehicle systems that change with respect to time during the trips of the separate vehicle systems. The one or more processors also are configured to assign the operators to remotely monitor or control the separate vehicle systems during the trips based on the time-variable risk profiles. The operator assigned to one or more of the separate vehicle systems changes with respect to time during the trip of the one or more separate vehicle systems while the one or more separate vehicle systems is moving along one or more routes during the trip.

Optionally, the one or more processors are configured to determine the time-variable risk profiles for the separate vehicle systems by identifying one or more time-varying risks to travel of the separate vehicle systems during movements of the trips that change with respect to location along the trips and/or with respect to elapsed time during the trips.

Optionally, the one or more processors are configured to determine the operator staffing demand by increasing how many of the operators are needed for remotely controlling one or more of the separate vehicle systems responsive to detection of an emergency situation involving the one or more separate vehicle systems.

Optionally, the one or more processors also are configured to change which of the operators are assigned to remotely control one or more of the separate vehicle systems during movement of the one or more separate vehicle systems during the trip of the one or more separate vehicle systems.

In one embodiment, a method includes determining a time-variable risk profile for a vehicle system that is to be one or more of remotely controlled or remotely monitored by one or more operators that are located off-board the vehicle system, and determining an operator staffing demand for the vehicle system based on the time-variable risk profile that is determined. The operator staffing demand represents how many of the operators are needed for one or more of remotely controlling or remotely monitoring the vehicle system. The method also includes assigning at least one of the operators to remotely monitor or control the vehicle system based on the operator staffing demand and the time-variable risk profile. The at least one operator assigned to the vehicle system changes with respect to time during travel of the vehicle system.

Optionally, determining the time-variable risk profile for the vehicle system includes identifying one or more time-varying risks to travel of the vehicle system that change with respect to time.

Optionally, the one or more time-varying risks include one or more of travel of the vehicle system through an urban area, travel of the vehicle system with a hazardous load, or a weather condition that changes with respect to time and through which the vehicle system is to travel.

Figure 6:
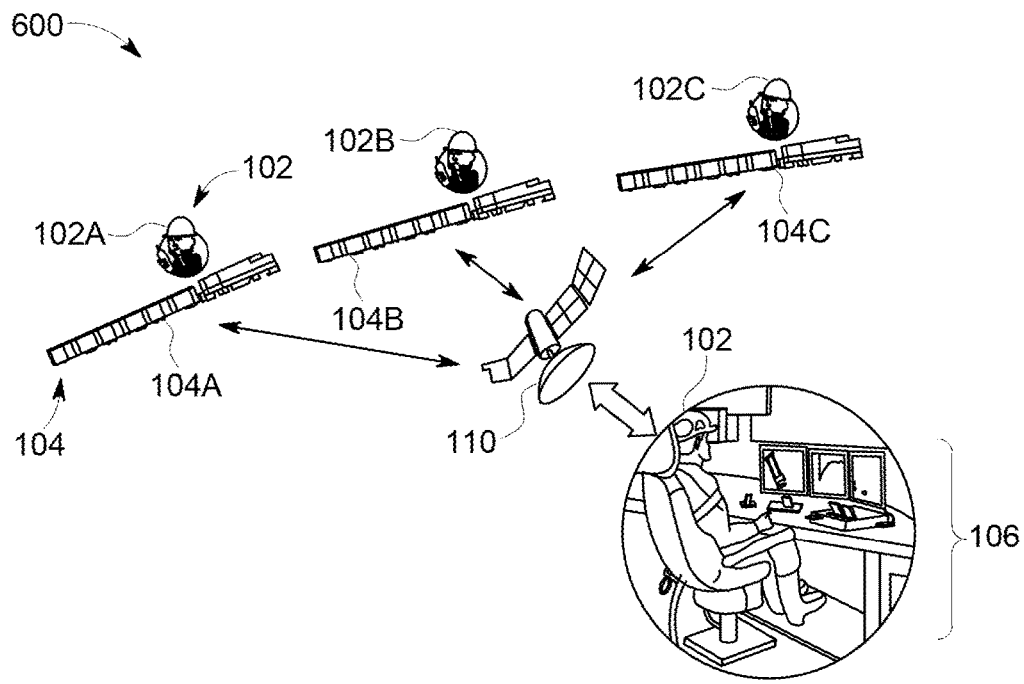
FIG. 6 illustrates one embodiment of a distributed control system.

FIG. 6 illustrates one embodiment of a distributed control system 600. The distributed control system is distributed such that multiple operators 102 (e.g., 102A-C) located in multiple, different, and remote locations are able to work on, control operations, and/or monitor operations of multiple, separate vehicle systems 104 (e.g., 104A-C). The operators may be in remote locations when at least one of the operators is off-board the vehicle system being controlled, with these operators concurrently controlling operations of the same vehicle system. For example, the operator 102A may be located onboard the vehicle system 102A to locally control operations of the vehicle system 102A and another operator may be located off-board the vehicle system 102A to control one or more of the same or different operations of the same vehicle system 102A. The vehicle systems may be separate when the vehicle systems are not mechanically coupled with each other and are not traveling with each other. The vehicle systems described herein may include a variety of different types of vehicles. For example, the vehicle systems may include rail vehicle systems (e.g., trains), automobiles, marine vessels, aircraft (e.g., drones), etc. and may be manned by one or more operators or be unmanned (i.e., more autonomous). While the vehicle systems are illustrated as trains, not all embodiments may be limited to trains. The vehicle systems are not model or toy vehicles in at least one embodiment of the subject matter described herein.

In one embodiment, the distributed control system includes a highly automated vehicle control system (not shown in FIG. 1) which is optionally manned by at least one operator disposed onboard the vehicle system (also referred to as a local or onboard crew member) and a remote-control system or station 106 that supports another operator (also referred to as a remote or off-board crew member. Alternatively, the vehicle system may be controlled by the remote and local control systems without any human operator disposed onboard the vehicle system. The remote crew member may use the remote station to control the operations of multiple vehicle systems. For example, the remote crew member may use the remote station to switch between controlling operations of different vehicle systems at different times and/or controlling operations of two or more vehicle systems at the same time.

The vehicle and remote-control systems are communicatively coupled by one or more networks. These networks can be wireless networks, such as networks that communicate signals between wireless communication devices or networks 110, such as antennas, satellites, routers, etc. The remote crew member or operator may monitor and/or control operations of the vehicle systems via signals communicated between the vehicle control system and the remote-control system via the communication devices.

In one embodiment, the communication devices may provide for much longer ranges of control of the vehicle systems than terrestrial wireless communication devices. For example, the communication devices can allow for a remote-control system to communicate with and remotely control vehicle systems over a range of hundreds or thousands of kilometers from the devices and the remote-control system. The communication devices may include satellites or devices that communicate with satellites (e.g., antennas and associated transceiving circuitry) that allow for wireless signals to be communicated between the vehicle systems and the remote-control system over very large distances of hundreds or thousands of miles or kilometers. This allows for the remote operator to remotely control the movement of a vehicle system without the vehicle system being within eyesight (e.g., the range of vision) of the remote operator (without use of a camera or magnifying device).

The remote operator may control different vehicle systems at different times. For example, during a first period of time, the remote operator may cause the remote-control system to generate and communicate signals to the vehicle control system of the vehicle system 104A to control operations (e.g., to change or control a throttle position) of the vehicle system 104A. During a subsequent, second period of time, the remote operator may cause the remote-control system to generate and communicate signals to the vehicle control system of the vehicle system 104B to control operations (e.g., to change or control a throttle position) of the vehicle system 104B. The remote operator and remote-control system may continue to switch between which vehicle system is controlled during different time periods to allow the remote operator to concurrently control the operations of several different vehicle systems. Optionally, the remote operator and the remote-control system can communicate signals to multiple vehicle systems at the same time or during overlapping time periods in order to simultaneously control operations of multiple vehicle systems. The remote-control system may control movements of these vehicle systems in an over-the-road environment. For example, instead of the remote-control system merely controlling movement of the vehicle systems within a vehicle yard (e.g., a rail yard), the remote-control system may control the movements of the vehicle systems along routes that extend between vehicle yards or that are much larger (e.g., longer) than the vehicle yards.

The remote-control system may remotely control movements of different vehicle systems based on conditions of the routes on which the vehicle systems are moving. For example, the remote-control system may remotely control movement of a vehicle system while that vehicle system is traveling on a first segment of the route that has fewer curves and/or has curves with larger radii of curvature than a different, second segment of the route. Responsive to the vehicle system traveling on the second segment of the route, the remote-control system may pass or hand off control of the vehicle system to an onboard operator.

The vehicle control systems onboard the vehicle systems may control the same or other operations of the vehicle systems as the remote-control systems. For example, in one embodiment, the remote-control system may control the throttle or speed command of a vehicle system during nominal conditions and the onboard operator of the same vehicle system can monitor the vehicle system and change the throttle setting, apply the brakes, or otherwise control operation of the vehicle system in response to identifying an unsafe situation (e.g., the vehicle system moving too fast, an obstruction on the route being traveled by the vehicle system, etc.). Optionally, the remote-control system can control or change operation of the vehicle system in response to identifying an unsafe situation (e.g., the vehicle system moving too fast, an obstruction on the route being traveled by the vehicle system, etc.).

Figure 7:
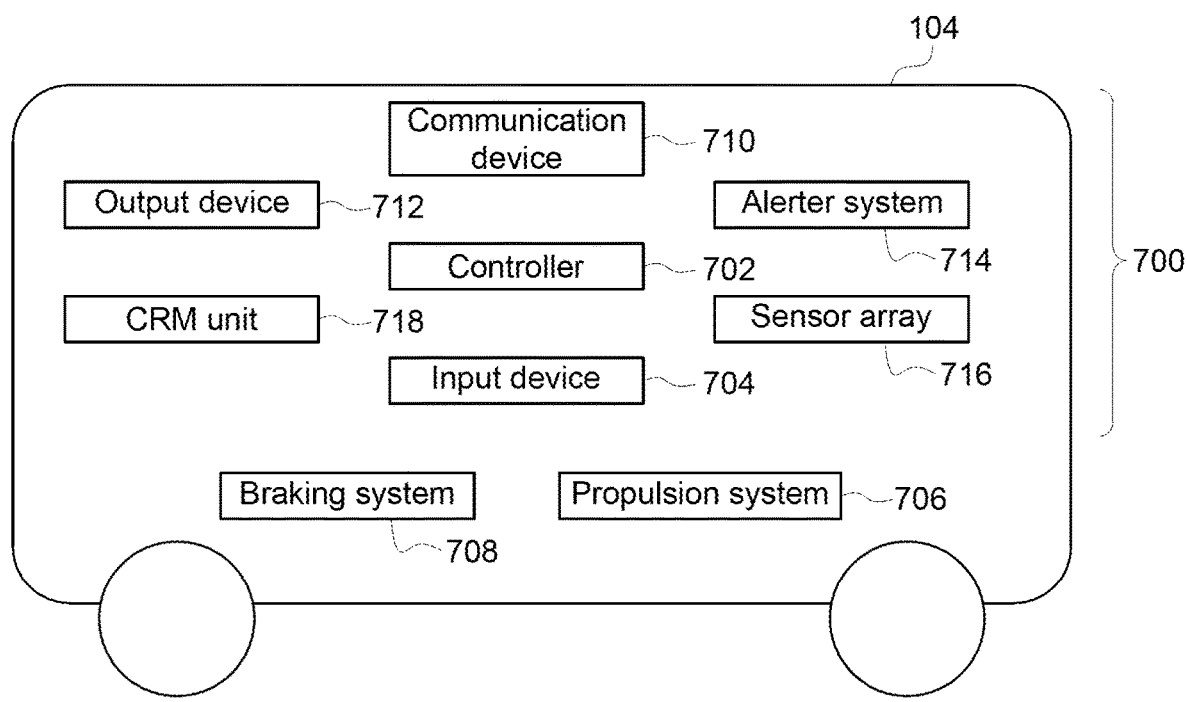
FIG. 7 illustrates one embodiment of a vehicle control system.

FIG. 7 illustrates one embodiment of a vehicle control system 700. The vehicle control system is disposed onboard the vehicle system. While the vehicle system is shown as a single vehicle in FIG. 7, optionally, the vehicle system may include multiple vehicles traveling together along a route. The vehicles in a vehicle system may be mechanically coupled with each other or may be mechanically decoupled or separate from each other but communicating with each other to coordinate movements of the vehicles such that the vehicles travel together as a larger vehicle system.

The vehicle control system includes a controller 702, which represents hardware circuitry that includes and/or is connected with one or more processors (e.g., microprocessors, controllers, field programmable gate arrays, and/or integrated circuits) that perform various operations described herein. The controller receives signals from an input device 704 that receives control input from the onboard operator of the vehicle system. The input device can represent one or more throttles (e.g., levers, pedals, etc.), buttons, touchscreens, switches, etc., that control operation of the vehicle system. For example, the input device can be actuated by the onboard operator of the vehicle system to change a throttle setting of a propulsion system 706 to change how quickly the vehicle system is moving, to change a brake setting of a brake system 708, to communicate one or more signals to the remote-control system (e.g., via a communication device 710 of the vehicle control system), or to otherwise control operation of the vehicle system.

The propulsion system represents one or more engines, generators, alternators, motors, or the like, that operate to propel the vehicle system. The brake system represents one or more brakes of the vehicle system, such as dynamic brakes, friction brakes, etc. The communication device represents hardware circuitry used for communicating signals with the remote-control system, such as one or more antennas, transceivers, routers, or the like. An output device 712 may present information to the onboard operator, such as information representative of operations of the vehicle system (e.g., moving speeds, speed limits, accelerations, temperatures, fuel levels, etc.), information communicated from the remote-control system (e.g., speeds at which the vehicle system is to move, locations where the vehicle system is to brake, etc.), or other information. The output device can represent one or more touchscreens (which also may be the input device) or other display devices, speakers, haptic devices, etc.

In one mode of operation, the vehicle control system receives control inputs from the remote-control system and uses the control inputs to automatically control operation of the vehicle system. The control inputs can designate operations or operational settings or parameters of the vehicle system, such as designated speeds at which the vehicle system is to travel, designated times and/or locations at which the vehicle system is to brake, designated accelerations and/or decelerations at which the vehicle system is to change speeds, locations that the vehicle system is to move toward, designated throttle settings, etc. The controller of the vehicle control system can receive these control inputs from the remote-control system via the communication device of the vehicle system and automatically control (e.g., without intervention of the onboard operator) the propulsion system and/or braking system of the vehicle system to implement the control inputs.

The remote-control of the vehicle system can provide the onboard or local crew member with more time to focus on other tasks (relative to the onboard or local crew member not having the remote-control system available for assisting in controlling movement of the vehicle system). For example, the onboard operator can have additional time to look for obstructions in the path of travel of the vehicle system, to monitor operation of the vehicle system, to perform maintenance, inspection, and/or repair of the vehicle system, or the like. The system can reduce the skill needed to manually control movement of the vehicle system, such as by having the remote-control system provide speed inputs and the vehicle control system being used by the operator to control the vehicle system to travel according to the speed inputs.

For example, the remote-control system may communicate speed set points, or designated speeds (and/or locations along a route, distances along a route, or times at which the vehicle system is to be traveling as the designated speeds) to the vehicle control system. These speeds may be provided to the vehicle control system as the vehicle control system is moving, in contrast to a previously determined or generated schedule or speed trajectory that is generated prior to movement of the vehicle system. The vehicle control system can receive and report these speeds to the onboard operator, and the onboard operator can actuate the input device onboard the vehicle system to cause the vehicle system to travel according to the designated speeds. Additionally, the onboard operator can safely and efficiently return to controlling movement of the vehicle system should the need arise by providing a speed input to the local control system, such as when the operator at the remote-control system is not able to remotely direct movement of the vehicle system, communication delays or interruptions prevent the remote-control system from communicating control inputs to the vehicle control system, etc.

The controller of the vehicle control system includes skilled driving knowledge that incorporates vehicle handling and other information used to determine how to change operational settings (e.g., throttle and/or brake settings) of the vehicle system to safely and efficiently control operation of the vehicle system according to the higher-order control inputs provided by the remote-control system. For example, the controller may receive operational set points as control inputs from the remote-control system and/or from the onboard operator. An operational set point can represent an operational goal that the vehicle system is to achieve, such as a moving speed, a location or distance in which the vehicle system is to stop or slow movement, a location to which the vehicle system is to travel, a time by which the vehicle system is to reach a location, an amount of fuel that the vehicle system is to consume or consume less than during movement, an amount of emissions that the vehicle system is to generate or generate less than during movement, throttle settings or positions, brake settings or positions, etc. The vehicle control system receives the operational set points and changes the settings of the propulsion system and/or braking system of the vehicle system so that the vehicle system achieves the set points.

As one example, the vehicle control system may receive a designated speed at which the vehicle system is to travel from the onboard operator and/or from the remote-control system. The controller of the vehicle control system may determine a current speed of the vehicle system (e.g., from a sensor such as a tachometer, global positioning system receiver, etc.) and compare the current and designated speeds to determine how to change the throttle and/or brake settings of the vehicle system to achieve the designated speed. In one example, the controller can determine changes in the throttle and/or brake settings that cause the vehicle system to achieve the designated speed while consuming less fuel and/or generating fewer emissions than using other, different changes in the throttle and/or brake settings (e.g., by switching to the highest throttle setting). In another example, the controller can determine the changes that reduce the number and/or size of throttle and/or brake setting changes relative to other changes, changes in the throttle and/or brake settings that reduce forces exerted on couplers relative to other changes, etc.

The controller can control the propulsion and/or braking systems to try and maintain, on average, the designated set point and/or to use the set point as an upper limit on the operational settings of the vehicle system. The controller can project speeds at which the vehicle system will move (e.g., determine a speed trajectory) based on the current speed and the changes to the throttle and/or brake settings in order to determine how to cause the vehicle system to travel at the set point designated by the remote-control system or the onboard operator.

The remote-control system may dictate control inputs that control operation of the vehicle system at various levels. For example, the remote operator can use the remote-control system to provide varying speed set points during a trip of the vehicle system as a function of locations of the vehicle system such that the set points change at two or more different locations. For example, set points may be communicated to the vehicle control system from the remote-control system as: proceed at time 0530, stop at location 123 by time 1400; set out car at siding (with protections and inputs provided by the onboard crew member; stop at location 53 until given authorization to move by foreman. A simple language/syntax can be developed for to provide these set points. The controller of the vehicle control system then transforms these set points into a speed command trajectory, which is used to determine the settings of the propulsion and braking systems of the vehicle system.

The vehicle control system may receive the operational set points and determine an operational setting trajectory for a vehicle system based on the operational set points. For example, the controller may receive the speed set points provided by the remote-control system and determine the throttle settings and/or brake settings that are to be used by the respective propulsion and braking systems in order for the vehicle system to reach the speed set points. The controller may examine the grades of the route, curvatures of the route, weights of the vehicles and/or cargo, etc., in order to determine the throttle and/or brake settings. For example, for inclined grades and/or heavier vehicles and cargo, larger throttle settings may be needed to accelerate to a faster speed set point than for flatter or declined grades and/or lighter vehicles and cargo. The throttle and/or brake settings may be designated for different locations along the route, distances along the route, and/or times. The controller may then control the propulsion and/or braking systems to implement the throttle and/or brake settings in order to achieve the speed set points.

Optionally, the vehicle control system and/or the onboard operator of the vehicle system can determine the set points of the vehicle system and communicate these set points to the remote-control system via the communication device. The remote-control system may examine the set points and determine the operational settings and/or changes to the operational settings of the vehicle system that can be used to reach or achieve the set points. The operational settings and/or changes in the operational settings may be communicated from the remote-control system to the vehicle control system so the controller of the vehicle control system can implement the operational settings and/or changes to the operational settings with the propulsion and/or braking systems.

An alerter system 714 of the vehicle control system monitors physiological features of the onboard operator of the vehicle system to determine whether the onboard operator is alert and able to provide sufficient safeguards against unsafe operation of the vehicle system by the onboard controller and/or the remote-control system. The alerter system receives monitoring signals from one or more sensors in a sensor array 716. These sensors can include heart rate monitors, blood pressure monitors, cameras, the input device 704, etc. The alerter system includes or represents hardware circuitry that includes and/or is connected with one or more processors (e.g., microprocessors, field programmable gate arrays, or integrated circuits) that receive and examine the monitoring signals from the sensor array. Based on the monitoring signals, the alerter system can determine whether the onboard operator of the vehicle system is alert and monitoring operations of the vehicle system.

For example, the alerter system can examine the blood pressure and/or pulse or heart rate and rate variation of the operator to determine if the operator is alive and alert. Optionally, the alerter system can examine other sensor data, such as electroencephalogram (EEG) data, electrocardiogram (ECG) data, or other contact/wearable measurements of the operator. The alerter system can receive images or video of the operator to determine whether the operator is moving at least as often as a designated frequency (e.g., once every minute, once every hour, etc.). The alerter system can receive images or video of the operator and use computer or machine vision techniques to determine postures and/or gestures of the operator, such as slouching versus upright, raised eyebrows or closed eyes, yawns or closed mouths, etc., to determine whether the operator is alert.

As another example, the alerter system provides cognitive tasks to the operator (e.g., via the output device) and examines the operator's performance of the tasks to determine whether the operator is alert. The cognitive tasks can include directions to play a game (e.g., tic-tac-toe), directions to perform a series of examinations of the vehicle system, directions to actuate a sequence of input devices (e.g., buttons, levers, areas of a touchscreen, etc.), or other tasks that require the operator to be alert to perform the tasks. If the operator does not complete the tasks to at least a specified level of achievement or is unable to complete the tasks, then the alerter system may determine that the operator is not alert. Optionally, the cognitive tasks may be contextual cognitive tasks. These tasks may be similar to the cognitive tasks previously described, but may require the operator to perform tasks related to operation of the vehicle system. For example, the alerter system may direct the operator to manually input (via the input device) the current location of the vehicle system, the current ambient temperature, the current weather conditions, the grade of the segment of the route currently being traveled upon, or the like. If the operator is unable to complete the task and/or to perform the task up to at least a designated level (e.g., the operator is unable to finish a game or is unable to beat the game), then the alerter system may determine that the operator is not currently alert.

In one embodiment, the alerter system contextually examines the observed operator behavior (e.g., inputs to local control system) to expected operator behavior generated through an awareness of vehicle context. For example, the alerter system may determine when the vehicle system is approaching a grade crossing and that the expected behavior is for the operator to be attentive to the crossing and place a hand on or near a horn actuator of the vehicle system. If the operator does not behave in this manner, then the alerter system determines that the operator is not alert.

Responsive to determining that the operator is not alert, the alerter system may perform one or more actions. The alerter system may actuate one or more alarms (e.g., lights, speakers, etc.) via the output device, the alerter system may direct the controller to automatically reduce the throttle and/or activate the braking system of the vehicle system, the alerter system may communicate a warning signal to the remote-control system, the alerter system may switch control of one or more operations of the vehicle system from the onboard operator or vehicle control system to the remote operator or remote-control system (e.g., control over the braking system), etc.

Optionally, the alerter system may monitor physiological features of an off-board operator at the remote-control system to determine whether the off-board operator is present and alert during remote-control of one or more vehicle systems. Responsive to determining that the off-board operator is not present or is not alert, the alerter system may pass or hand off remote-control of a vehicle system to another remote operator or to an operator onboard the vehicle system.

In one embodiment, the communication devices and/or the controllers can monitor the communication or data link(s) between the communication devices to determine whether to change how the vehicle system is controlled based on the communication or data link(s). A communication or data link can represent a connection between the communication devices to permit communication of data between the communication devices. The link can be disrupted or interrupted due to a variety of causes, such as failure of a communication device, travel of the vehicle system through a tunnel or valley, electromagnetic interference from sources external to the vehicle system, etc. The communication or data link between the remote-control system and the vehicle system can be monitored by the communication devices and, if the link become interrupted, destroyed, or too limited (e.g., the bandwidth or speed of the link decreases below a designated threshold, such as by decreasing by 50% or more), then the communication devices and/or controllers can assign another remote-control system to control and be communicatively coupled with the vehicle system.

The vehicle control system also includes a crew resource management (CRM) unit or console 718. With the vehicle system being controlled using a distributed crew of operators, the CRM unit 718 provides for non-verbal communication between the remote and local operators of the vehicle system. The CRM unit represents hardware circuitry that includes and/or is connected with one or more processors (e.g., microprocessors, integrated circuits, field programmable gate arrays, etc.) that receive signals from the remote operator via the remote-control system and the communication device, from the onboard operator via the input device, from the alerter system, from an alerter system of the remote-control system, and/or from one or more other locations, and display or otherwise present this information to the onboard operator of the vehicle system. For example, if the onboard or remote operator updates the speed or state of the vehicle system, an indicator light can be activated on the CRM unit, which notifies the other operators of the updated speed or state. The CRM unit may require that the operator in the same location of the CRM unit confirm or acknowledge the changed speed or state, such as by actuating the input device. This acknowledgement may be communicated to the operators (local and remote) to ensure that all operators are aware of changes in the operations of the vehicle system and are aware that other operators are aware of the changes.

Figure 8:
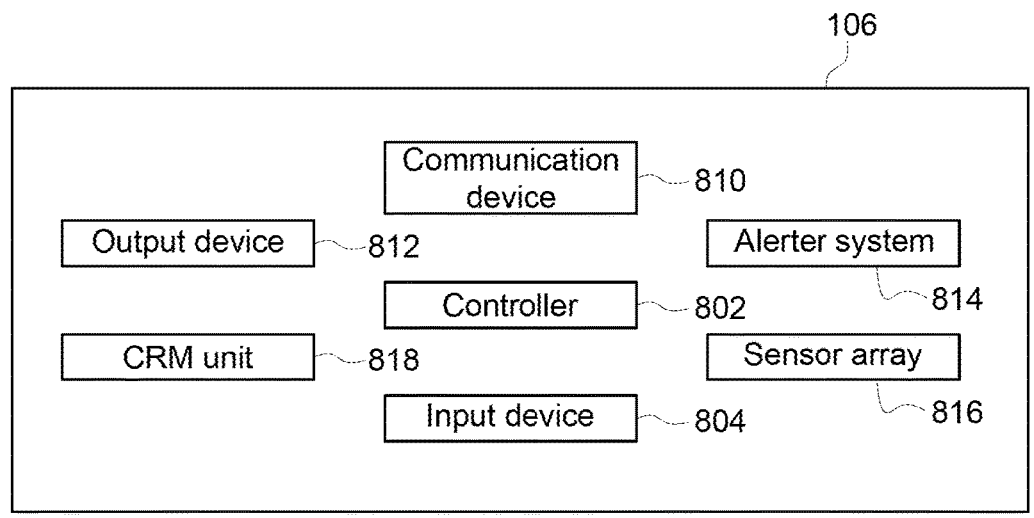
FIG. 8 illustrates one embodiment of a remote-control system shown in FIG. 6.

FIG. 8 illustrates another embodiment of the remote-control system 106. The remote-control system includes a communication device 810, which may be similar or identical to the communication device of the vehicle control system, to permit the remote and vehicle control systems to communicate with each other. The remote-control system also includes a controller 802, which may be similar or identical to the controller 202 of the vehicle control system.

The controller 802 may perform the operations of the remote-control system described herein. The remote-control system also may include an input device 804, an alerter system 814 and sensor array 816 that operate and perform the same or similar functions as described above in connection with the same components of the vehicle control system. This allows the remote-control system to determine whether the remote operator at the remote-control system is alert. The remote-control system also includes an output device 812 similar or identical to the output device 812 of the vehicle control system, and a CRM unit 818 that is identical or similar to the CRM unit 818 of the vehicle control system.

The remote-control system can allow a single remote operator to remotely control operations of several vehicle systems and maintain awareness of other relevant vehicle systems. The controller of the remote-control system may generate signals for display on the output device to represent current states of various vehicle systems. The remote operator or controller may select a vehicle system to be controlled, and the remote operator may change one or more of the operational settings of the selected vehicle system via the input device of the remote-control system, such as by setting a set point for the vehicle system. The controller of the remote-control system may then generate a signal representative of the set point for communication to the controller of the vehicle control system to allow for the vehicle system to be controlled. The remote-control system and/or remote operator may switch between controlling several different vehicle systems at different times or allow the operator to control multiple vehicle systems at the same time.

The remote operator can have access to significantly more information about the context of the vehicle systems being controlled by the remote-control system than any single local operator of a vehicle system in one embodiment. Because the remote-control system may be communicating with several vehicle systems at a time, data representing the states of these vehicle systems can be aggregated and presented to the remote operator by the CRM unit 818 via the output device 812. These data include current locations, speeds, and statuses of the vehicle systems and the crew members on the vehicle systems (e.g., from the controller, alerter system, CRM unit, or other data source), the location of each vehicle system relative to each other and other waypoints, and physical aspects of the region of operation (e.g., network switch states, signals from dispatcher, maintenance areas, slippery areas, etc.).

Figure 9:
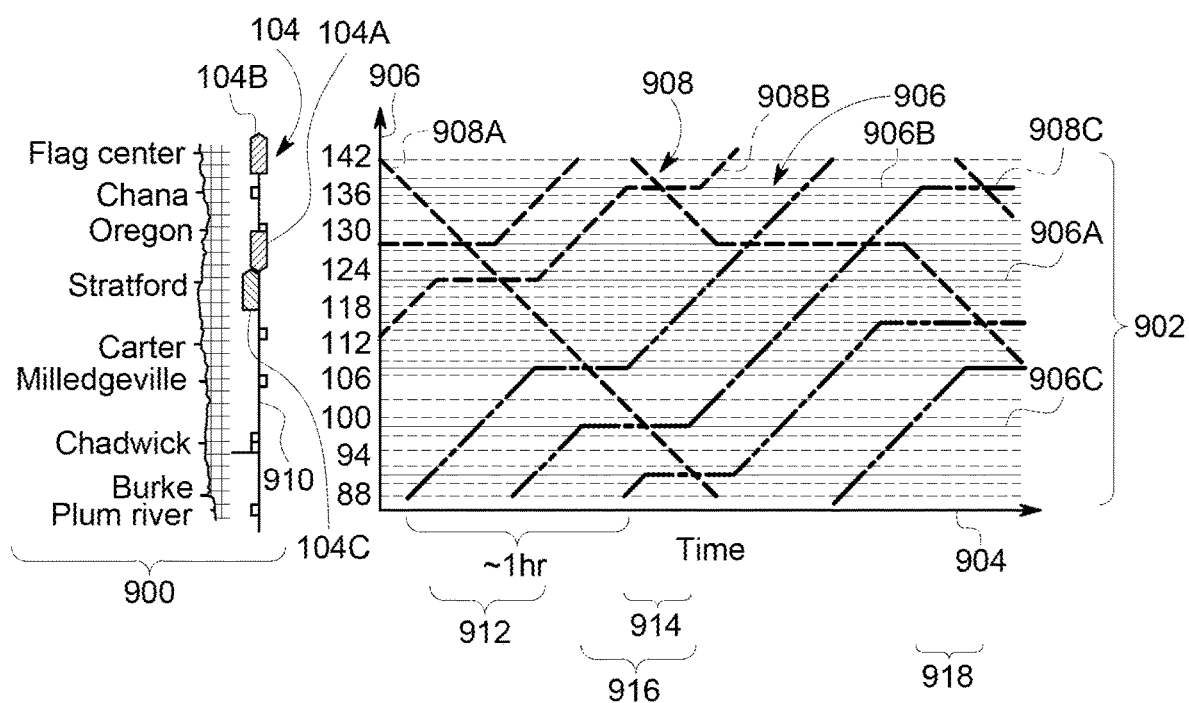
FIG. 9 illustrates one example of a graphical user interface (GUI) presented to an operator of the remote and/or vehicle control system by a crew resource management unit of the corresponding remote and/or vehicle control system.

FIG. 9 illustrates one example of information presented to an operator of the remote and/or vehicle control system of the corresponding remote and/or vehicle control system. The information shown in FIG. 9 can be presented on the output device, such as a display, to the operator. This information shows an elevation map 900 of the route being traveled by one or more vehicle systems, along with locations of stops and other relevant waypoints along the elevation map 900, locations of vehicle systems, and directions of travel of the vehicle systems indicated on or near the elevation map 900 (e.g., by the arrow end of the symbols representing the vehicle systems).

A network status representation 902 can be presented to the operator to indicate the current and future states of the vehicle systems, as estimated or predicted by the controller of the remote-control system based on current states of the vehicle systems. The status representation 902 is shown alongside a horizontal axis 904 representative of time and a vertical axis 906 representative of different locations along a selected route being traveled by different vehicle systems.

In the illustrated embodiment, several solid lines 906 indicate locations of alternate or siding routes that a vehicle system may move onto to get off of the route shown in the map 900 and allow another vehicle system to pass on the route. Several scheduled movement lines 908 (e.g., movement lines 908A-C) represent estimated, scheduled, or predicted movements of several vehicle systems.

For example, a movement line 908A can represent the movement of a first vehicle system 106A along a route 910, a movement line 908B can represent the movement of a second vehicle system along the route 910, and a movement line 908C can represent the movement of a third vehicle system along the route 910. This information presented to the operator by the output device can indicate that the vehicle system is scheduled to travel in a first direction of travel along the route 910 without stopping or pulling off onto any siding routes, while the second vehicle system is to travel in an opposite direction of travel along the same route 910 to a siding represented by the route line 906A, pull off of the route 910 onto the siding 906A and wait for a designated period of time 912, pull back onto the route 910 and travel to another siding represented by the route line 906B, pull off of the route 910 onto the siding 906B and wait for a designated period of time 914, and pull back onto the route 910 and travel along the route 910. This information also indicates that the vehicle system is scheduled to travel in the same direction of travel along the route 910 as the second vehicle system, but at a later time, and to pull off of the route 910 onto a siding 906C and wait for a designated period of time 916, pull back onto the route 910 and travel to the siding 906B, pull off of the route 910 onto the siding 906B and wait for a designated period of time 918, and pull back onto the route 910 and travel along the route 910.

The remote operator may be assigned with controlling movement of the vehicle systems traveling along a designated section of the route 910, such as the portion of the route 910 shown in FIG. 9. Responsive to a vehicle system entering into the section of the route being controlled by a remote operator, the vehicle system may begin being controlled by that remote operator. Prior to the vehicle system entering into this section of the route and after the vehicle system leaves this section of the route, the vehicle system may be controlled by other remote operators. The remote operator in charge of controlling the vehicle systems along the section of the route may concurrently or simultaneously control movements of the vehicle systems while those vehicle systems are on the section of the route.

Figure 10:
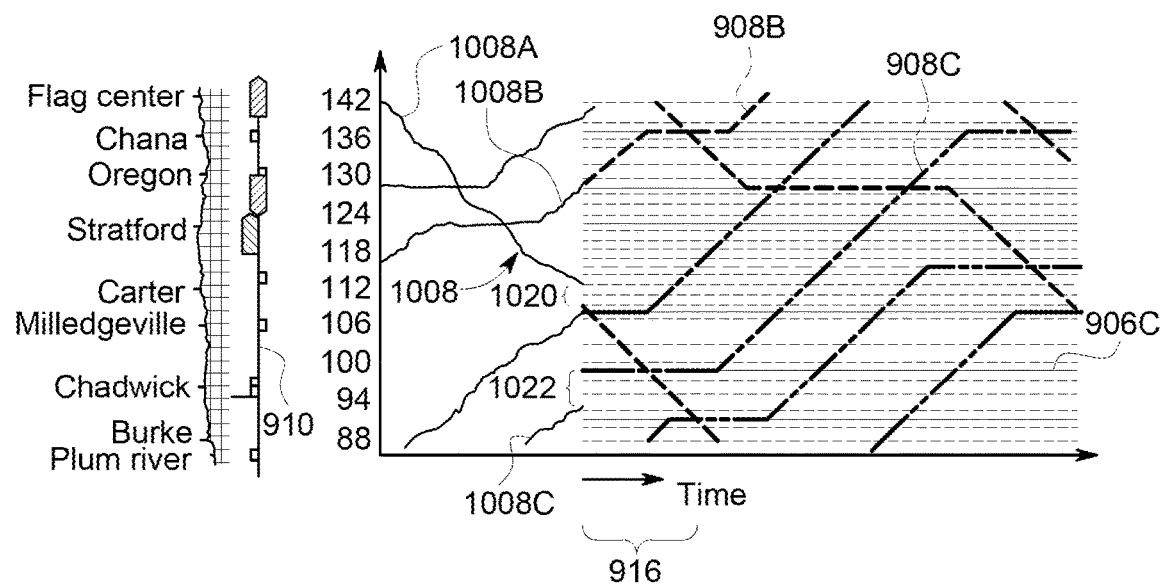
FIG. 10 illustrates another example of a GUI presented to an operator of the remote and/or vehicle control system.

FIG. 10 illustrates another example of information presented to an operator of the remote and/or vehicle control system described herein by the corresponding output device. The information shown in FIG. 10 is an updated version of the information shown in FIG. 9. For example, as the vehicle systems move along the route 910, the CRM unit can update and display actual locations of the vehicle systems along the route as completed movement lines 1008 (e.g., movement lines 1008A-C).

Differences 1020, 1022 between the planned or scheduled movement lines 908 and the actual movement lines 1008 can indicate vehicle systems moving ahead of or behind schedule. For example, the difference 1020 can indicate that the first vehicle system is moving behind schedule along the route 910 and the difference 1022 can indicate that the third vehicle system is moving along the route 910 even farther behind schedule. This changing information can provide rapidly discernable updates on locations of the vehicle systems to the remote operator who is controlling movements of the vehicle systems. The operator may change how the vehicle systems are controlled based on the information shown by the output device, such as by increasing the speed set points of the first and third vehicle systems and/or extending the period of time 916 that the third vehicle system remains on the siding 906C.

Figure 11:
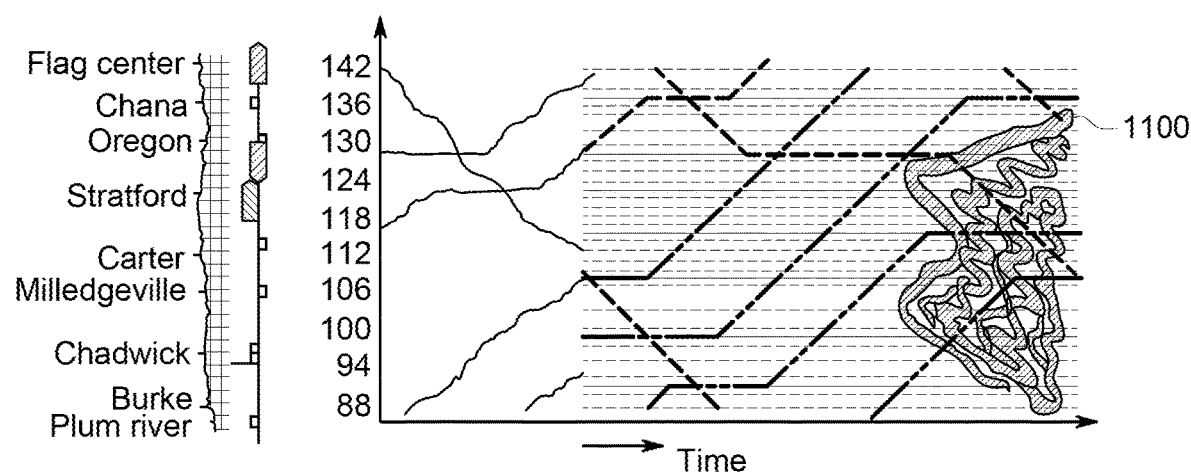
FIG. 11 illustrates another example of a GUI presented to an operator of the remote and/or vehicle control system.

FIG. 11 illustrates another example of information presented to an operator of the remote and/or vehicle control system described herein by the corresponding output device. The information shown in FIG. 11 is an updated version of the information shown in FIG. 10. For example, as weather conditions change, graphical weather indicators 1100 may be overlaid or otherwise shown on the output device. In the illustrated embodiment, the weather indicators can represent when and where precipitation (e.g., rain, ice, and/or snow) is predicted by occur, such as by information provided from meteorologists or from other sources. The location of the weather indicators can visually inform the remote operator of when and where weather conditions may impact movement of the vehicle systems. In response to seeing the weather indicators, the operator can change how one or more of the vehicle systems are controlled, such as by slowing movement of the vehicle systems, increasing braking distances of the vehicle systems, etc.

Figure 12:
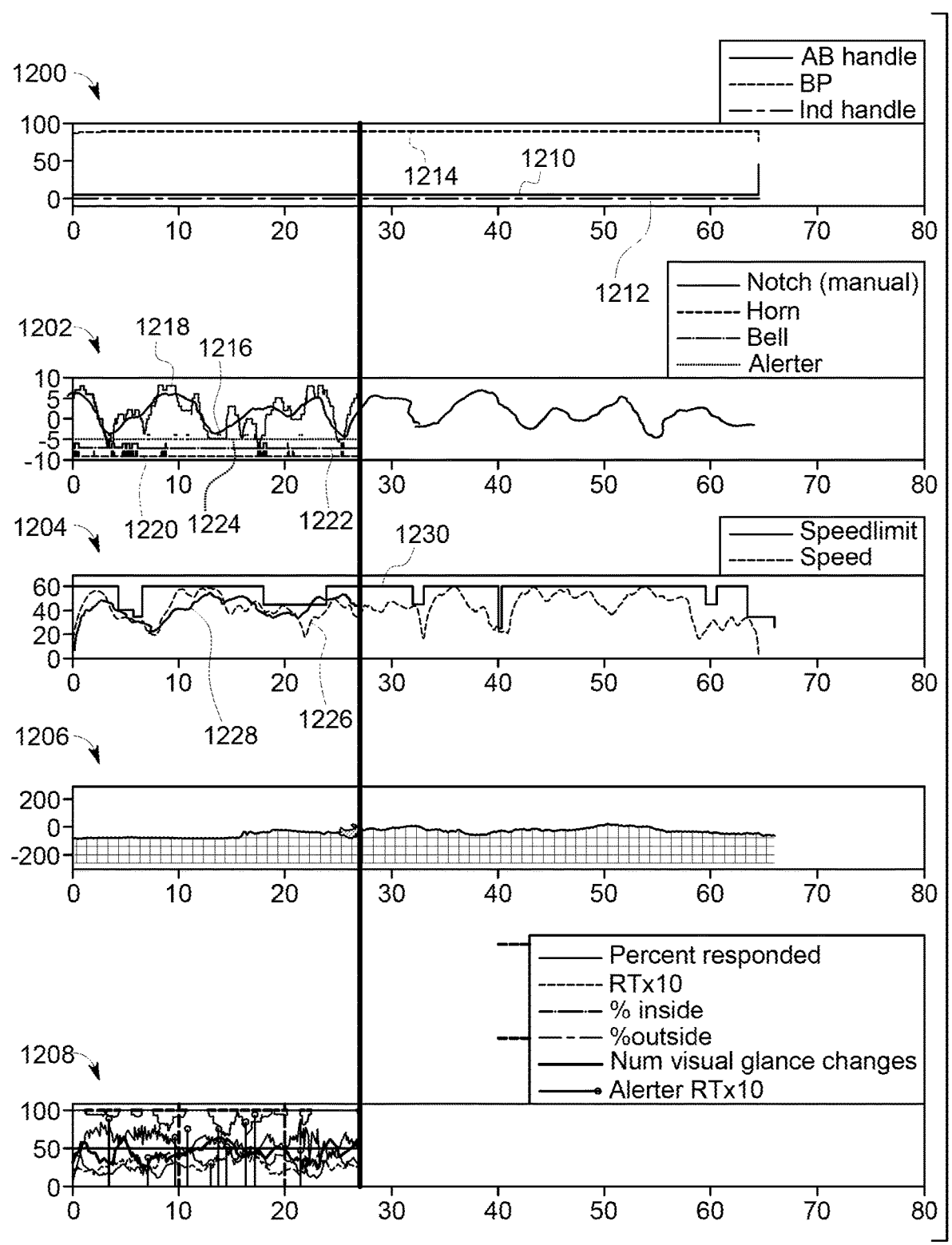
FIG. 12 illustrates another example of information presented to an operator of the remote and/or vehicle control system by the corresponding output device.
Figure 13:
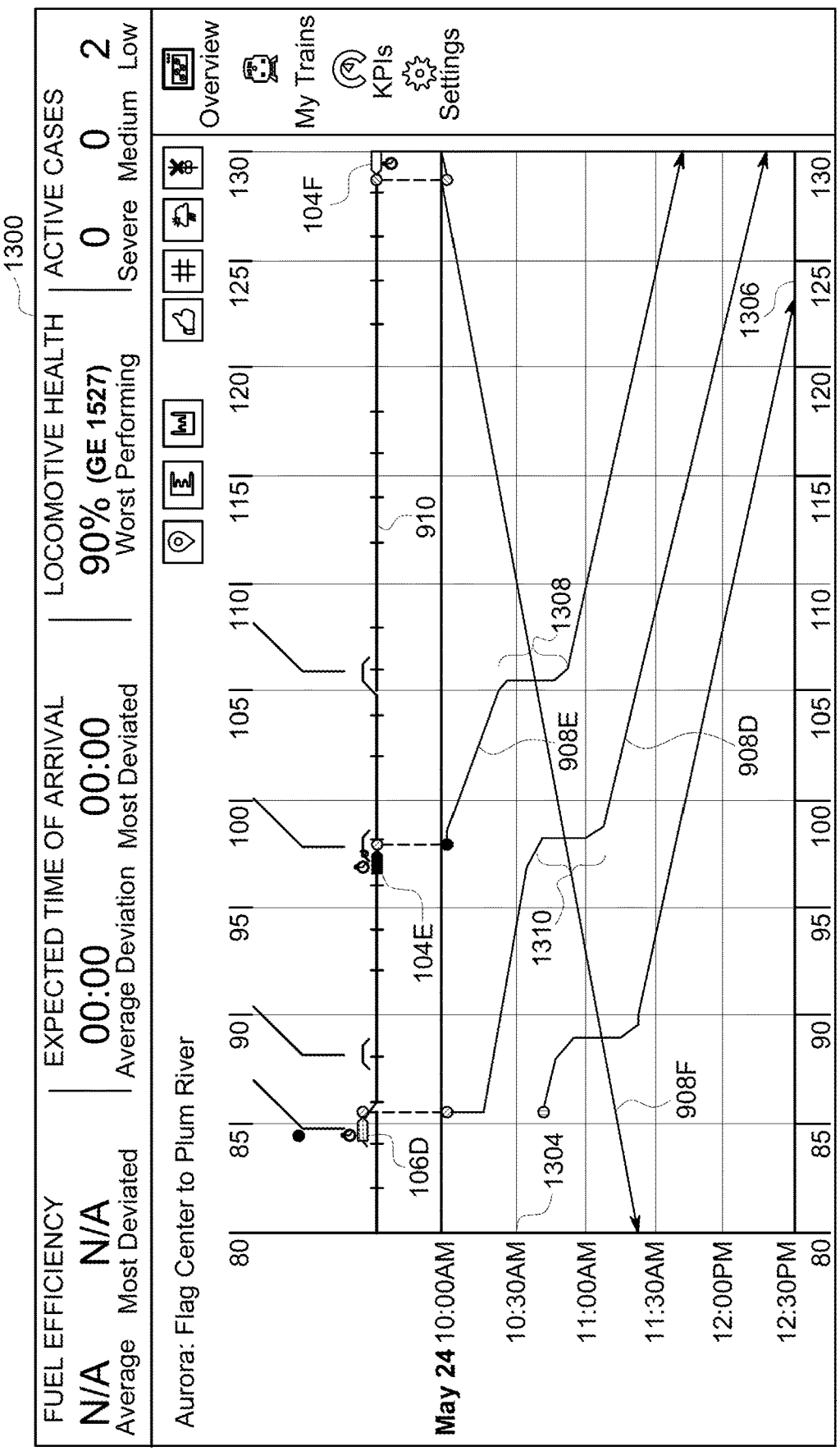
FIG. 13 illustrates an additional example of a GUI presented to an operator of the remote and/or vehicle control system of the corresponding remote and/or vehicle control system.

FIG. 12 illustrates another example of information presented to an operator of the remote and/or vehicle control system described herein by the corresponding output device. The information shown in FIG. 12 represents at least some of the monitoring information obtained by the alerter system of one or more of the remote and/or vehicle control systems and presented to one or more operators via the output device to allow the operators off-board (and, optionally, onboard) the vehicle systems to monitor operations of the vehicle systems and alertness of the onboard operators of the vehicle systems.

An operational setting chart 1200 presents settings of the vehicle system at different times. This chart 1200 can illustrate, for example, a setting 1210 of the braking system of the vehicle system (e.g., the position of an air brake handle), a pressure 1212 of air in the braking system of the vehicle system, a position 1214 of an individual brake of a vehicle in the vehicle system, and/or other information. The information shown in the chart 1200 can be obtained by and/or provided from the controller and/or the CRM unit of the vehicle control system and communicated to the CRM unit of the remote-control system via the communication devices.

An operational input chart 1202 presents the onboard operator-controlled settings of the vehicle system at different times. This chart 1202 can illustrate, for example, a designated throttle setting or position 1216 (e.g., as determined or dictated by the remote-control system and communicated to the vehicle control system), an actual throttle setting or position 1218 (e.g., the throttle position actually used by the onboard operator), a horn indicator 1220 (e.g., representing if and/or when the horn or other alarm system of the vehicle system is activated), a bell indicator 1222 (e.g., representing if and/or when another bell or other alarm system of the vehicle system is activated), and/or an alerter indicator 1224 (e.g., represent if and/or when the alerter system onboard the vehicle system detects that the onboard operator is not alert). Alternatively or additionally, other information may be presented. This chart 1202 can be examined to determine whether the onboard operator is controlling or attempting to control the vehicle system according to the designated operational settings provided by the remote-control system.

A speed chart 1204 presents designated moving speeds 1226 of the vehicle system (e.g., as determined by the remote-control system), speed limits 1228 of the route, and actual moving speeds 1230 of the vehicle system at different times and/or locations along the route. This chart 1204 can be examined by the remote operator to determine if and/or when the vehicle system is violating any speed limits and/or if the vehicle system can move at a faster speed.

An elevation chart 1206 presents elevations or grades of the route being traveled by the vehicle systems at different or locations along the route. An operator fatigue chart 1208 presents information related to the alertness of the onboard operator. The data used to generate the chart 1208 may be obtained by the alerter system and/or vehicle control system. If the chart 1208 indicates the alertness of the onboard operator of a vehicle system, then the alerter system onboard the vehicle system can obtain the data used to generate the chart from the sensor array also onboard the vehicle system, and communicate this information to the CRM unit in the remote-control system. If the chart 1208 indicates the alertness of the off-board operator of the remote-control system, then the alerter system of the remote-control system can obtain the data used to generate the chart from the sensor array of the remote-control system, and communicate this information to the CRM unit onboard one or more vehicle systems and/or in another remote-control system. The operators can monitor the information shown in the chart 1208 to determine if the remotely located operator (e.g., onboard a vehicle system or at a remote-control system) is alert. Examples of the information that can be presented in the chart 1208 include percentages of responses obtained from the operator when queried to provide a response by the alerter system, a number of times the glances of the operator changes (e.g., as determined by examining images or video of the operator), or other information.

The data from multiple different charts can be examined and compared to determine if the operator is alert. For example, the charts may have a common (e.g., the same) horizontal axis so that simultaneous events appear at the same locations along the horizontal axes of the charts. As one example, if an operator at a remote-control system is monitoring the alertness of an operator onboard a vehicle system, the off-board operator can determine if the fatigue chart indicates that the operator is not alert at the same times as or prior to times when the throttle settings change in the chart 1202, and/or if the throttle is being changed later than the designated changes in throttle. If the onboard operator is slow to change the throttle and/or brake settings, is violating speed limits, and/or the alerter system is providing data indicating that the operator is not alert, then the remote-control system can generate one or more alarms (e.g., onboard the vehicle system via the output device) to awaken the operator or to cause the operator to become more alert, can automatically slow or stop movement of the vehicle system, can send signals to another vehicle system to approach and/or check on the operator that appears to not be alert, etc.

Distributing at least part of the control system of vehicle systems to an off-board location can allow for a remotely located operator to assist in controlling the movements of several separate vehicle systems. This operator may be able to more easily switch between controlling and/or assisting in the control of multiple vehicle systems than onboard operators, which can allow for the off-board operator to concurrently or simultaneously assist in controlling and/or control multiple vehicle systems. The off-board operator may be replaced by another off-board operator when a contractual or other work shift of the off-board operator ends, which can allow for the vehicle systems to continue moving while not losing the assistance of the off-board operator. Otherwise, the vehicle systems may have to stop for a crew change to allow for the operators having work shifts that are ending to be removed from the vehicle systems and replaced by other operators. Additionally, the off-board operator may be more highly trained, have more specialized training, and/or be more experienced than operators onboard the vehicle system, and this greater experience, higher training, and/or specialized training can allow for the operator to work at the remote-control system such that the experience and/or training of the operator is used to control and/or assist in controlling the movement of several different vehicle systems.

In one embodiment, multiple operators at the same and/or different remote-control systems can assist in controlling and/or control operations of the same vehicle system. For example, a first off-board operator may control the operational settings of a first propulsion-generating vehicle in the vehicle system while a second off-board operator (at the same or different remote-control system) may control the operational settings of a second propulsion-generating vehicle in the same vehicle system. Alternatively, the off-board operators may control different settings of the same vehicle, such as one off-board operator controlling speed, another off-board operator monitoring the alertness of an onboard operator, another off-board operator monitoring brake pressures, etc., of the same vehicle.

The number and/or responsibilities of the off-board operators monitoring and/or controlling a vehicle system can change based on an operational state of the vehicle system, such as when one or more circumstances or scenarios occur. For example, responsive to determining that the vehicle system is entering a more densely populated area (e.g., an urban area) than a previous area, the number of remote operators controlling and/or assisting in controlling the vehicle system may increase. Conversely, responsive to determining that the vehicle system is entering a less densely populated area than a previous area, the number of remote operators controlling and/or assisting in controlling the vehicle system may decrease. As another example, responsive to determining that cargo carried by the vehicle system hazardous and/or has a higher priority than other vehicle systems (e.g., a shipping arrangement for the cargo has a higher value than other shipping arrangements), the number of remote operators controlling and/or assisting in controlling the vehicle system may increase. As another example, responsive to determining that the vehicle system is traveling in an area having increased traffic of other vehicle systems, that one or more components of the vehicle system have failed or are likely to fail, and/or that one or more onboard operators are no longer alert, the number of off-board operators controlling and/or assisting in controlling the vehicle system may increase.

The controller of the remote-control system may determine when one or more of these scenarios occur based on data obtained from the vehicle system. For example, the vehicle system may include one or more location determining devices, such as a global positioning system receiver, a radio frequency identification tag reader, a dead reckoning system, or the like, that can report back locations of the vehicle system to the remote-control system. The remote-control system may have access to the trip manifest of the vehicle system to determine the cargo being carried by the vehicle system. The sensor array can provide data representative of the onboard operator alertness and/or the operational health of components of the vehicle system. Based on this and/or other data, the remote-control system can determine when to increase and/or decrease the number of off-board operators to assign to controlling operations of the same vehicle system. In one aspect, the off-board operators may be located at different remote-control systems or terminals, and the controller of a remote-control system may connect or disconnect the communication device of additional remote-control systems with each other and/or the vehicle system to change the number of off-board operators assisting with control of the same vehicle system.

FIGS. 13 through 17 illustrate additional examples of GUIs 1300, 1400, 1500, 1600, 1700 presented to an operator of the remote and/or vehicle control system shown in FIG. 1 of the corresponding remote and/or vehicle control system. The GUI shown in FIGS. 13 through 17 can be presented on the output device, such as a display, to the operator. This GUI shows a horizontal, linear map of a route 910 being traveled by several vehicle systems, along with locations of stops and other relevant waypoints along the route 910, locations of the vehicle systems, and directions of travel of the vehicle systems.

A network status representation or map 1302 is presented to the operator to indicate the current and future states of the vehicle systems, as estimated or predicted by the controller of the remote-control system based on current states of the vehicle systems. The status representation is shown alongside a horizontal axis 1304 representative of different locations along a selected route being traveled by different vehicle systems and alongside a vertical axis 1306 representative of time. Several movement lines 908 (e.g., movement lines 908D-F) represent estimated, scheduled, or predicted movements of several vehicle systems (e.g., the vehicle systems 104D-F), similar to as described above. In the illustrated example, the arrow heads on the ends of the movement lines and/or the slope of the movement lines indicate that the vehicle systems 104D, 104E are moving along the route in a left-to-right direction in the perspective of FIGS. 13 through 17 (e.g., a negative slope) and that the vehicle system 104F is moving along the route in an opposite direction (e.g., as indicated by the positive slope). The intersection of the movement lines with different time (e.g., vertical axis) and distance (e.g., horizontal axis) coordinates indicate where the vehicle systems will be located at different times.

For example, the movement line 908D can represent the movement of a fourth vehicle system 104D along the route, the movement line 908E can represent the movement of a fifth vehicle system 104E along the route, and the movement line 908F can represent the movement of a sixth vehicle system 104F along the route (in a direction that is opposite that of the direction of movement of the vehicle systems 104D, 104E). The movement line 908D includes a vertical or predominately vertical (e.g., more vertical than horizontal) portion 1310. This portion 1310 indicates that movement of the fourth vehicle system is paused or at least slowed for a time period over which the portion 1310 extends (e.g., along the vertical axis). The fourth vehicle system may, for example, pull off of the route onto a siding route or other route for this time period at the location of the portion 1310 along the route to allow the vehicle system 104F to pass the vehicle system 104D along the route.

The movement line 908E also includes a vertical or predominately vertical portion 1308. This portion 1308 indicates that movement of the vehicle system 104E is paused or at least slowed for a time period over which the portion 1308 extends. The vehicle system 104E may, for example, pull off of the route 910 onto a siding route or other route for this time period at the location of the portion 1308 along the route to allow the vehicle system 104F to pass the vehicle system 104E along the route.

Passage of the vehicle system 104F by the vehicle systems 104D, 104E as the vehicle systems 104D, 104E are stopped or slowed is shown in the GUI by the movement line 908F of the vehicle system 104F intersecting or crossing over the movement lines 908D, 908E of the vehicle systems 104D, 104E.

The remote operator may be assigned with controlling movement of the vehicle systems traveling along a designated section of the route, such as the portion of the route shown in FIGS. 13 through 17. Responsive to a vehicle system entering into the section of the route being controlled by a remote operator, the vehicle system may begin being controlled by that remote operator. Prior to the vehicle system entering into this section of the route and after the vehicle system leaves this section of the route, the vehicle system may be controlled by other remote operators. The remote operator in charge of controlling the vehicle systems along the section of the route may concurrently or simultaneously control movements of the vehicle systems while those vehicle systems are on the section of the route.

Figure 14:
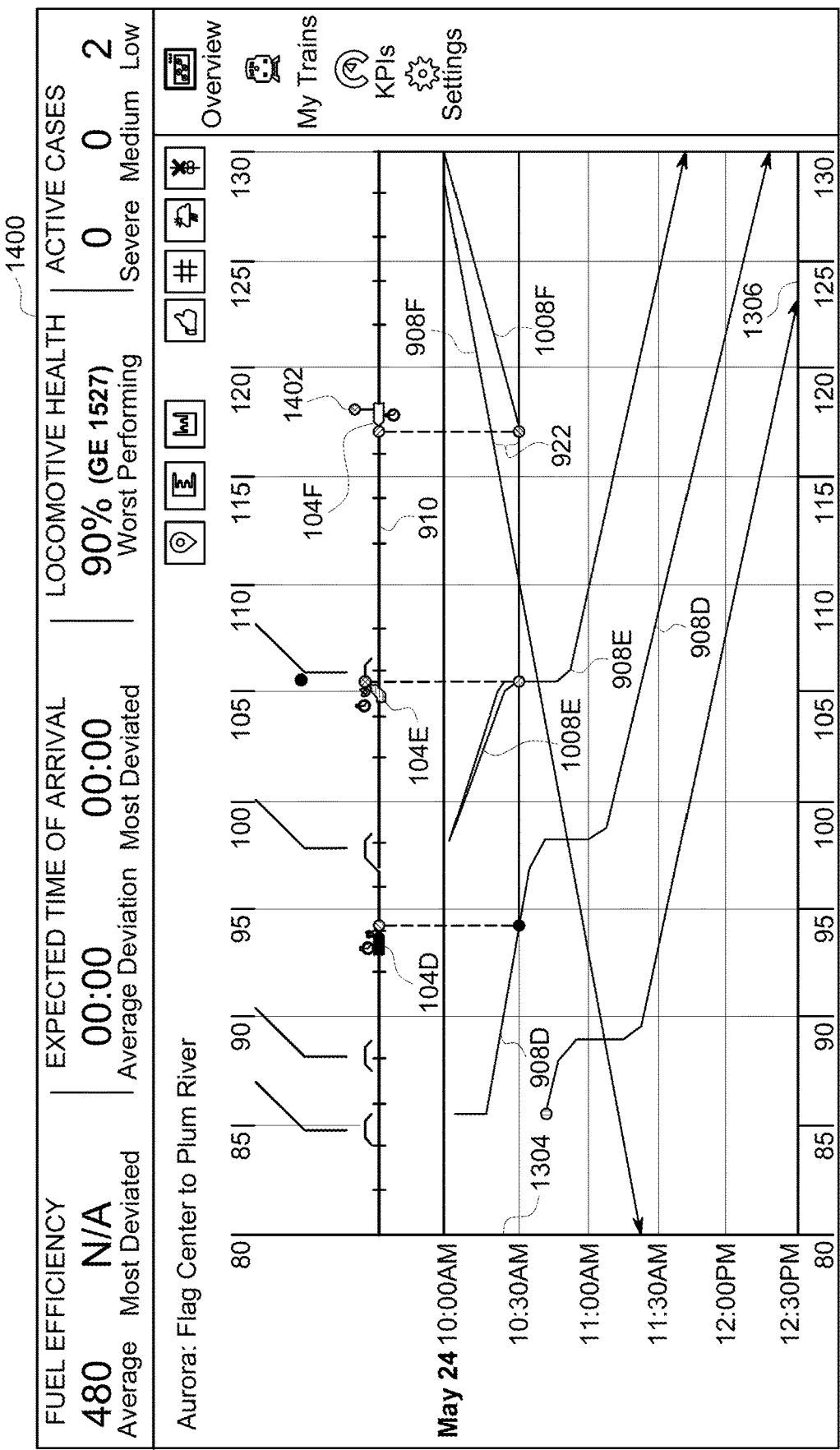
FIG. 14 illustrates an additional example of a GUI presented to an operator of the remote and/or vehicle control system of the corresponding remote and/or vehicle control system.

FIG. 14 illustrates another example of a GUI 1400 shown to an operator of the remote and/or vehicle control system by the corresponding output device. The GUI 1400 represents the current statuses (e.g., relative locations, speeds, etc.) of the vehicle systems at a time subsequent to the time represented by the GUI shown in FIG. 13. For example, as the vehicle systems move along the route, the CRM unit can update and display actual locations of the vehicle systems along the route as completed movement lines (e.g., movement lines 1008D-F). The completed movement lines represent portions of the scheduled movement lines 908D-F that the vehicle systems have completed travel over. The completed movement lines 1008 may be shown in a different manner than the scheduled movement lines 908, as shown in FIG. 14.

In the illustrated example, the vehicle system 104F has discovered and/or reported a faulty signal along the route at a fault location 1402. This (and/or other faults or factors) may result in the vehicle system 104F traveling behind schedule. The movement of the vehicle system 104F behind schedule is represented by a difference 1422 between the scheduled movement line 908F and the completed movement line 1008F of the vehicle system 104F, as shown in the GUI. The operator of the control system or remote-control system may view the GUI to determine the location 1402 of the faulty signal (e.g., for re-routing or changing the schedules of one or more other vehicle systems based thereon) and/or that the vehicle system 104F is moving behind schedule.

Figure 15:
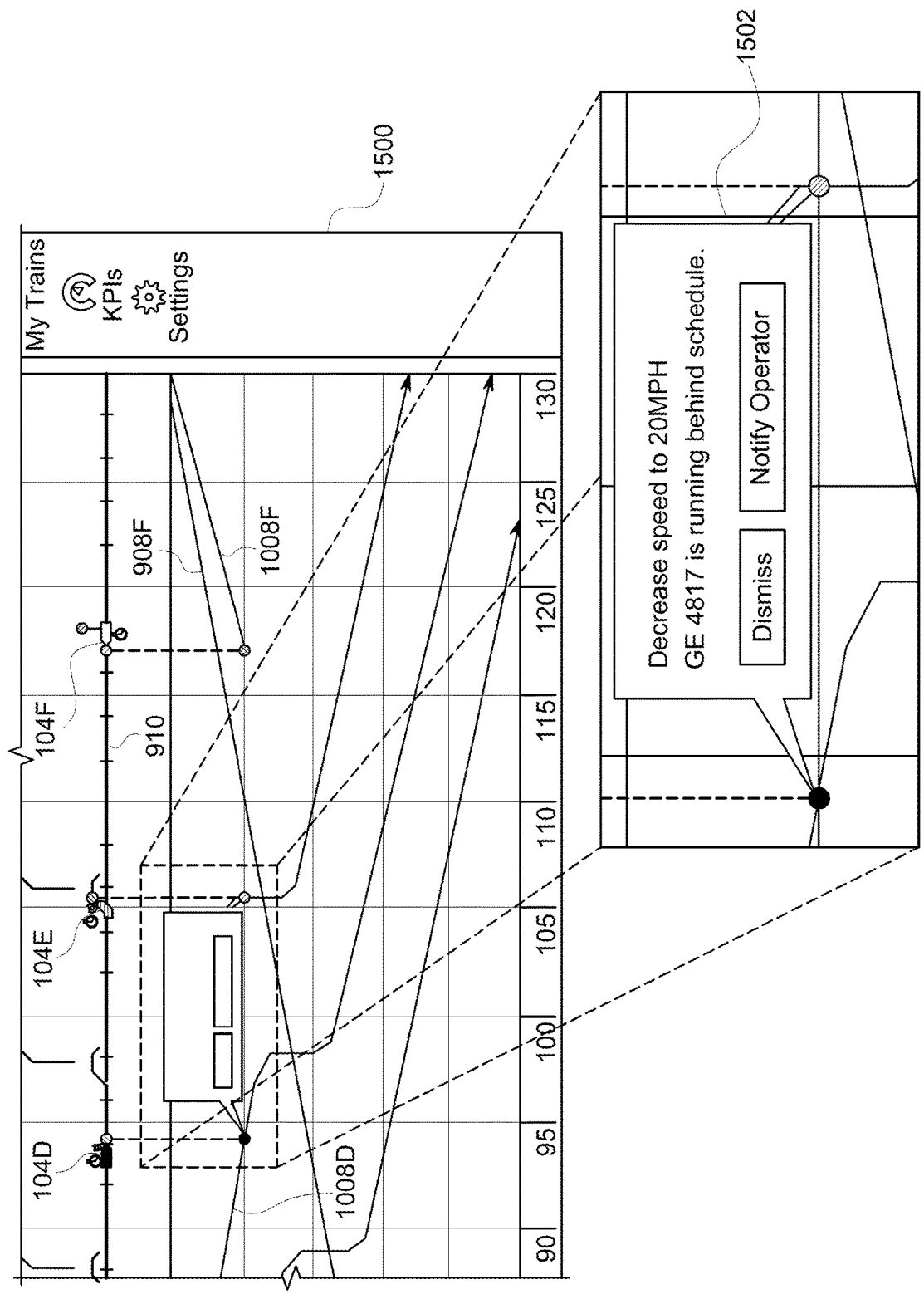
FIG. 15 illustrates an additional example of a GUI presented to an operator of the remote and/or vehicle control system of the corresponding remote and/or vehicle control system.

FIG. 15 illustrates another example of a GUI 1500 shown to an operator of the remote and/or vehicle control system by the corresponding output device. The operator of the remote-control system may generate a notification 1502 that informs one or more of the vehicle systems of a change or deviation from scheduled movements of the vehicle systems. In the illustrated example, the remote-control system generates a signal that is wirelessly communicated (and/or communicated via one or more wired connections) to the vehicle system 104D to provide the notification 1502 to the vehicle system 104D. This notification 1502 can direct the vehicle system 104D to change speeds, such as by slowing down (in this example), speeding up, or otherwise deviating from the scheduled movement line 908D for the vehicle system 104D. In response to receiving the notification 1502, the controller of the vehicle system 104D may direct the propulsion system to reduce tractive effort or propulsive force generated by the propulsion system and/or may direct the braking system to increase braking effort generated by the braking system.

Figure 16:
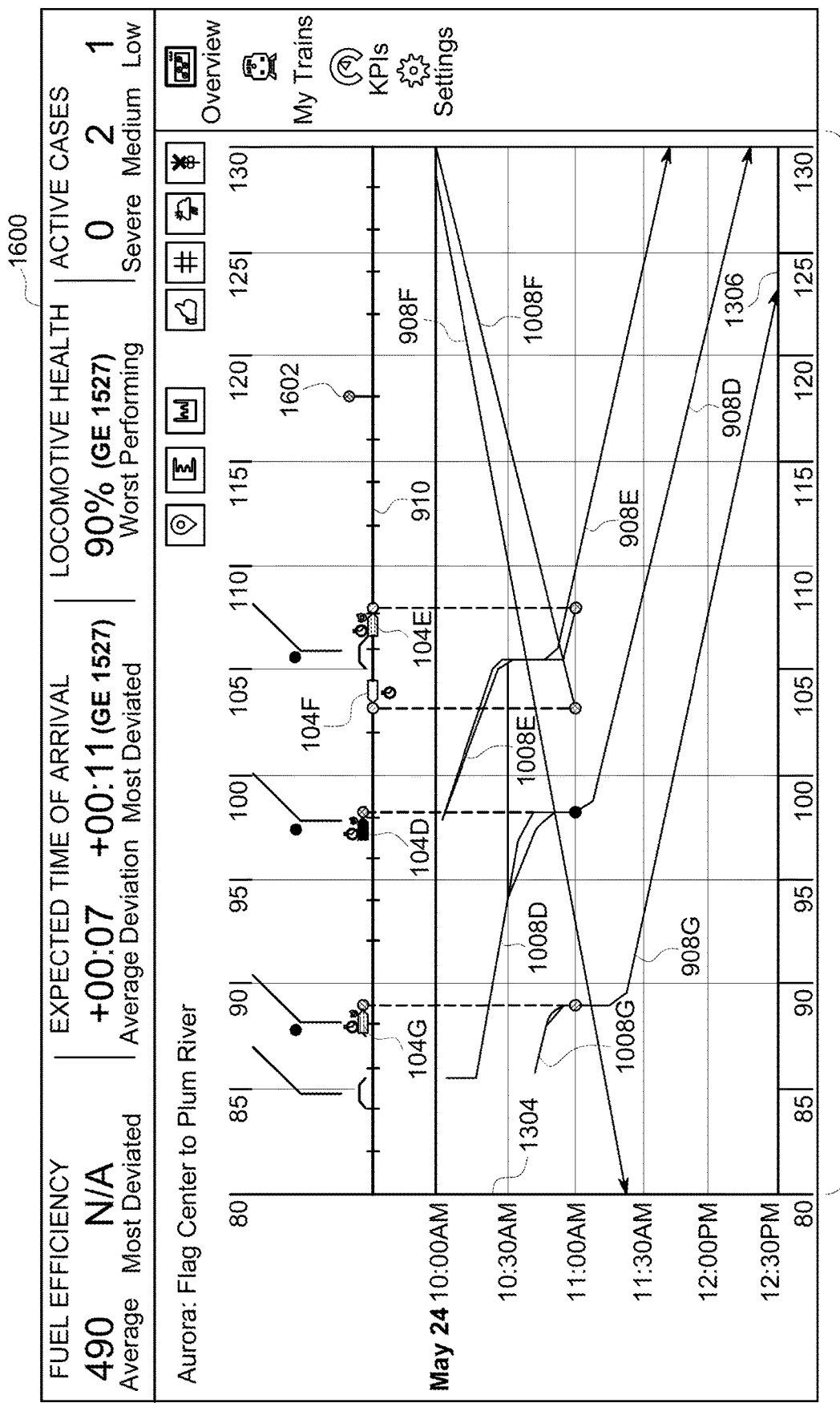
FIG. 16 illustrates an additional example of a GUI presented to an operator of the remote and/or vehicle control system of the corresponding remote and/or vehicle control system.

FIG. 16 illustrates another example of a GUI 1600 shown to an operator of the remote and/or vehicle control system by the corresponding output device. The GUI 1600 includes an icon 1602 that represents the location of the faulty signal described above. The GUI 1600 also includes an additional scheduled movement line 908G and a completed movement line 1008G for an additional vehicle system 104G. As shown, the completed movement lines 1008D, 1008E for the vehicle systems 104D, 104E deviate from the scheduled movement lines 908D, 908E. This can inform the operator that the vehicle systems 104D, 104E are traveling behind schedule. With respect to the vehicle system 104D, the operator may remotely control the vehicle system 104D to speed up to catch up to the scheduled movement line 908D. For example, while the vehicle system 104D slowed down relative to the speeds dictated by the scheduled movement line 908D, the vehicle system 104D may have been sped up by the remotely located operator so that the vehicle system 104D returns to traveling according to the movement line 908D, as shown in FIG. 16.

Figure 17:
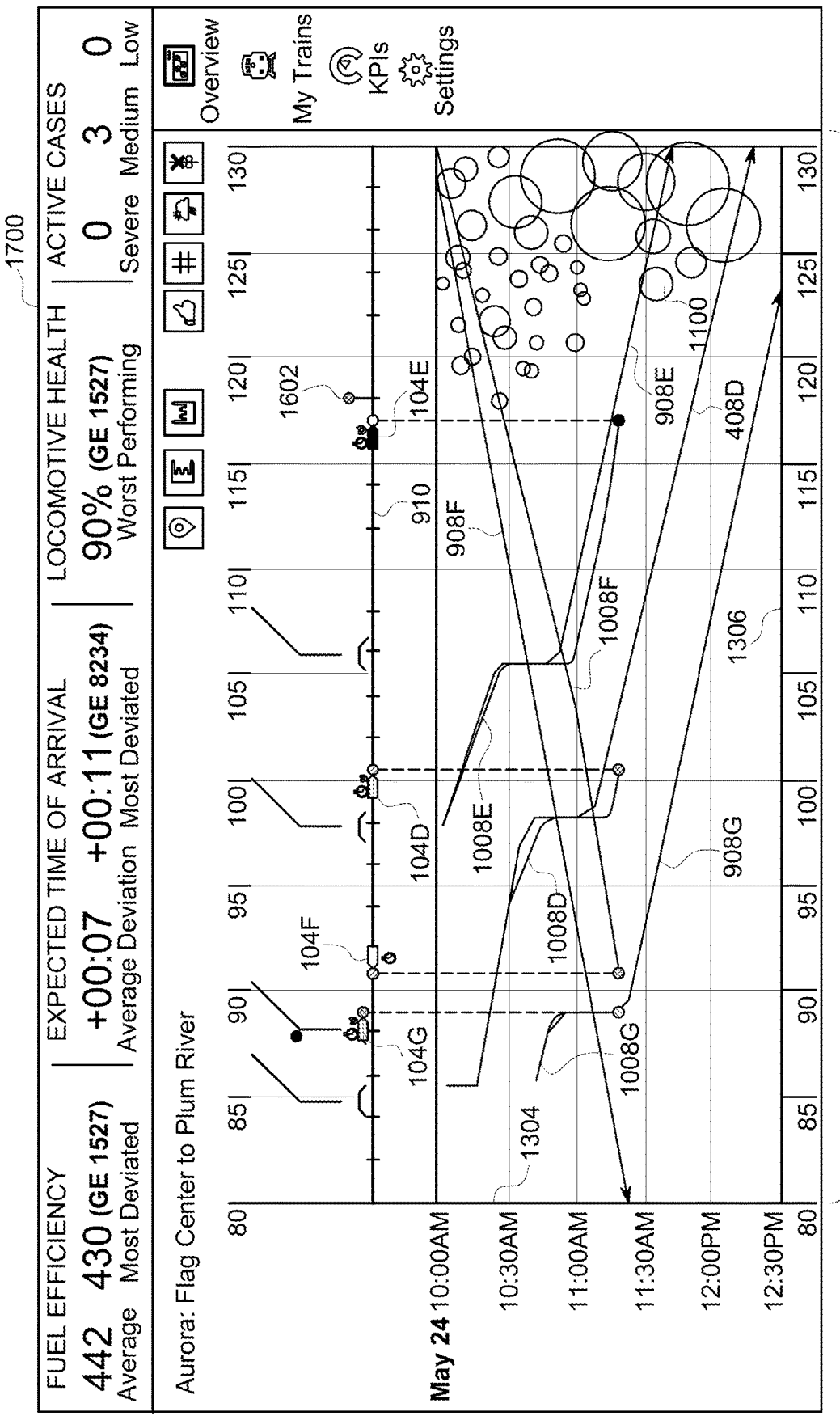
FIG. 17 illustrates an additional example of a GUI presented to an operator of the remote and/or vehicle control system of the corresponding remote and/or vehicle control system.

FIG. 17 illustrates another example of a GUI 1700 shown to an operator of the remote and/or vehicle control system by the corresponding output device. The GUI 1700 includes the graphical weather indicators 1100 that are overlaid or otherwise shown on the output device, as described above. The weather indicators can represent when and where precipitation (e.g., rain, ice, and/or snow) is predicted by occur, such as by information provided from meteorologists or from other sources. The location of the weather indicators can visually inform the remote operator of when and where weather conditions may impact movement of the vehicle systems. In response to seeing the weather indicators, the operator can change how one or more of the vehicle systems are controlled, such as by slowing movement of the vehicle systems, increasing braking distances of the vehicle systems, etc.

Figure 18A:
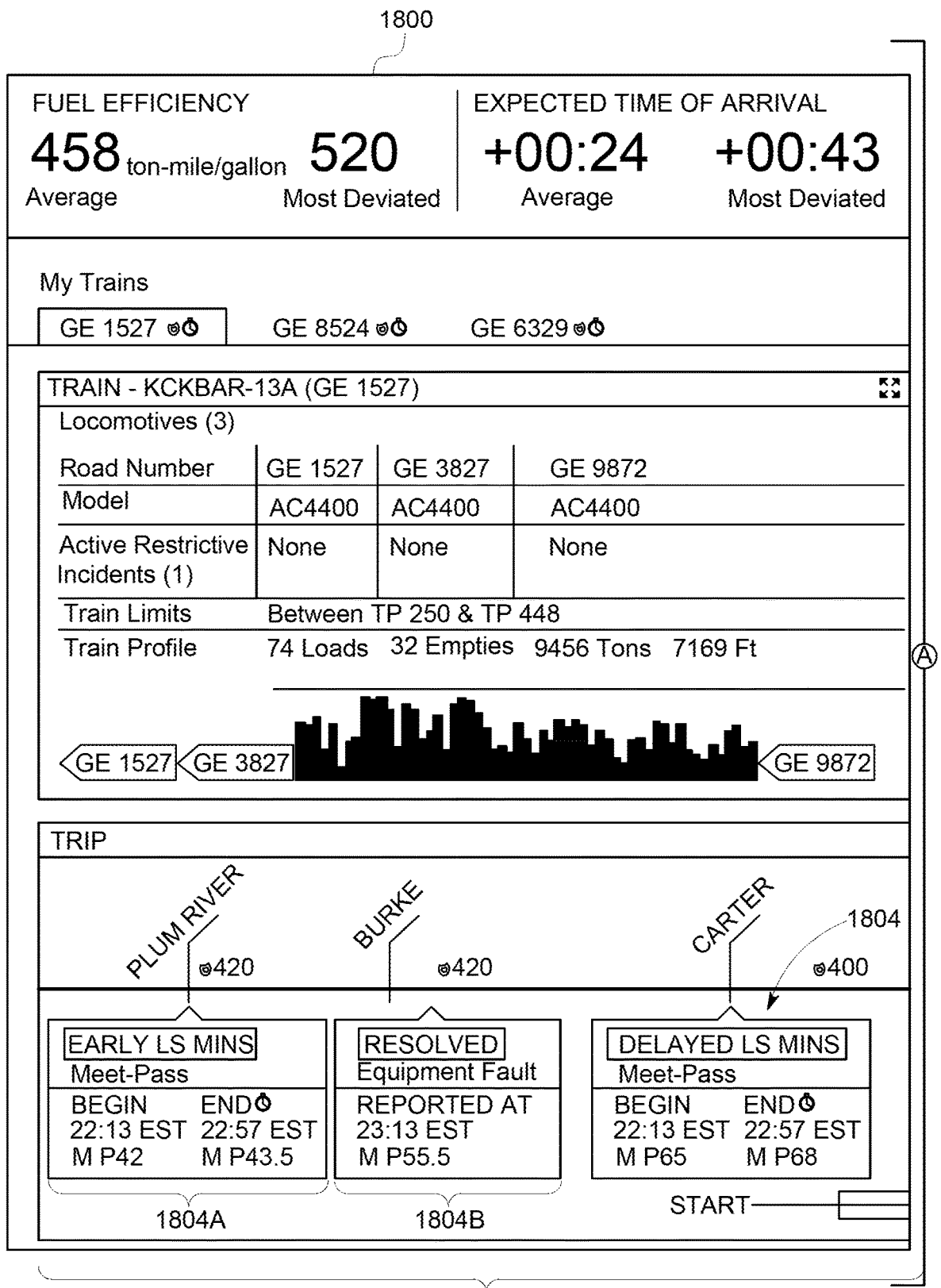
FIGS. 18A and 18B illustrate another example of a GUI shown to an operator of the remote and/or vehicle control system by the corresponding output device.
Figure 18B:
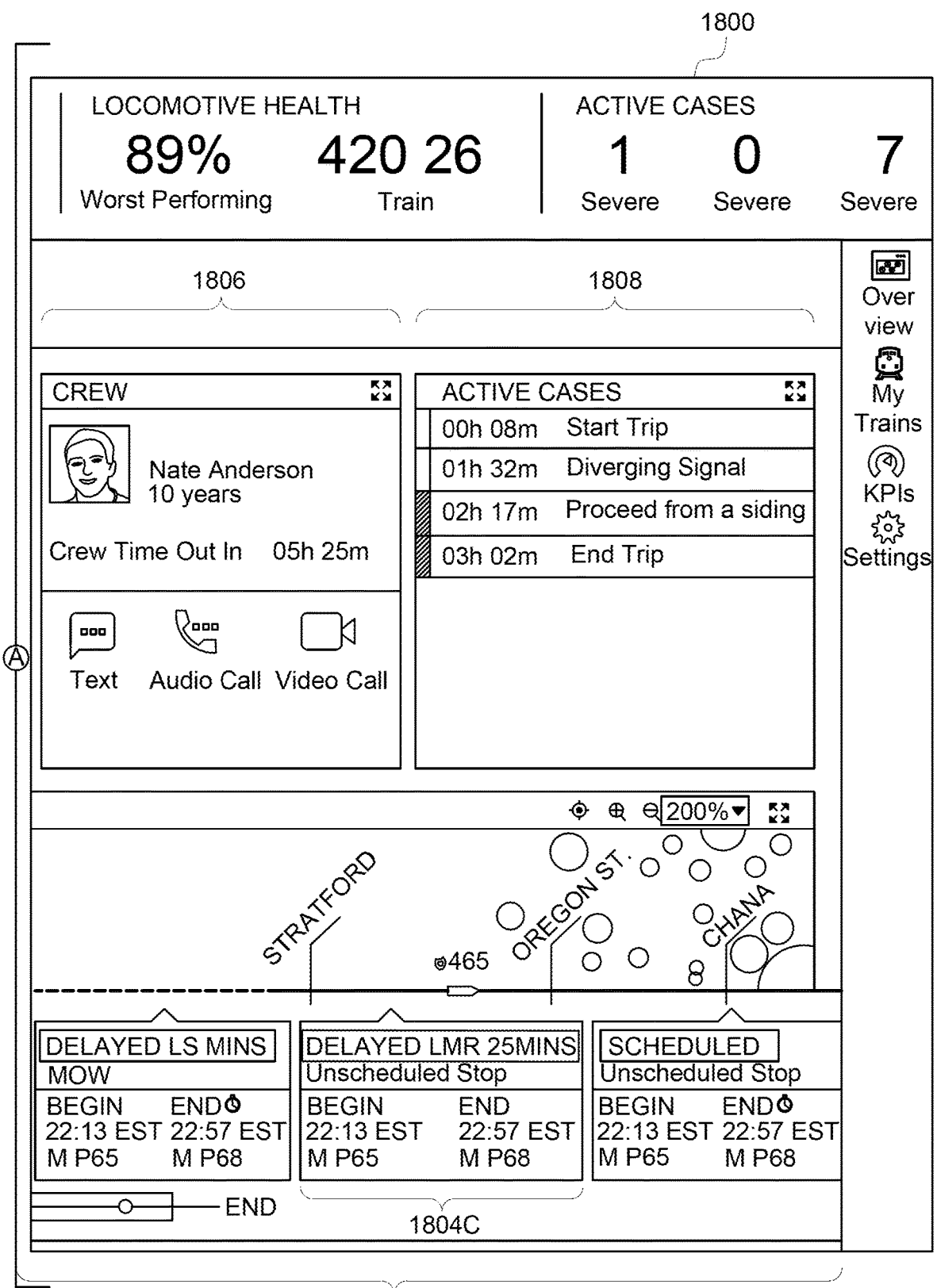

FIGS. 18A and 18B illustrate another example of a GUI 1800 shown to an operator of the remote and/or vehicle control system shown in FIG. 1 by the corresponding output device. The GUI 1800 may be presented to the operator concurrently or simultaneously with presentation of one or more other GUIs described herein (e.g., on different portions of the same output device, on different output devices, etc.). The GUI 1800 provides a visual representation of a case manager that allows the operator to select different vehicle systems to control based on other information presented on the GUIs described herein. The GUI 1800 presents a map 1802 that indicates a current location of a vehicle system. The map 1802 includes icons indicative of scheduled and/or unscheduled events 1804 that the vehicle system has encountered. For example, the icons shown in FIGS. 18A and 18B indicate that the vehicle system arrived early at a meet-and-pass event 1804A, that an equipment failure event 1804B was discovered, that the vehicle system performed an unscheduled stop event 1804C, and so on.

The GUI 1800 can serve as a case manager to allow a remote operator (represented by an operator display portion 1806) to select different vehicle systems to be remotely controlled by the remote operator. Icons indicative of scheduled events 1808 of the vehicle system that is selected by the operator are displayed to the remote operator. In the illustrated example, the operator can view these icons to determine which actions that the operator is to achieve by remotely controlling movement of the vehicle system (e.g., start a trip at a scheduled time, reach a signal at a diverging route, proceed from a siding section of route, and end the trip at a scheduled time). The operator can use these icons as a sort of checklist to ensure that the scheduled actions of the vehicle system are completed.

Figure 19:
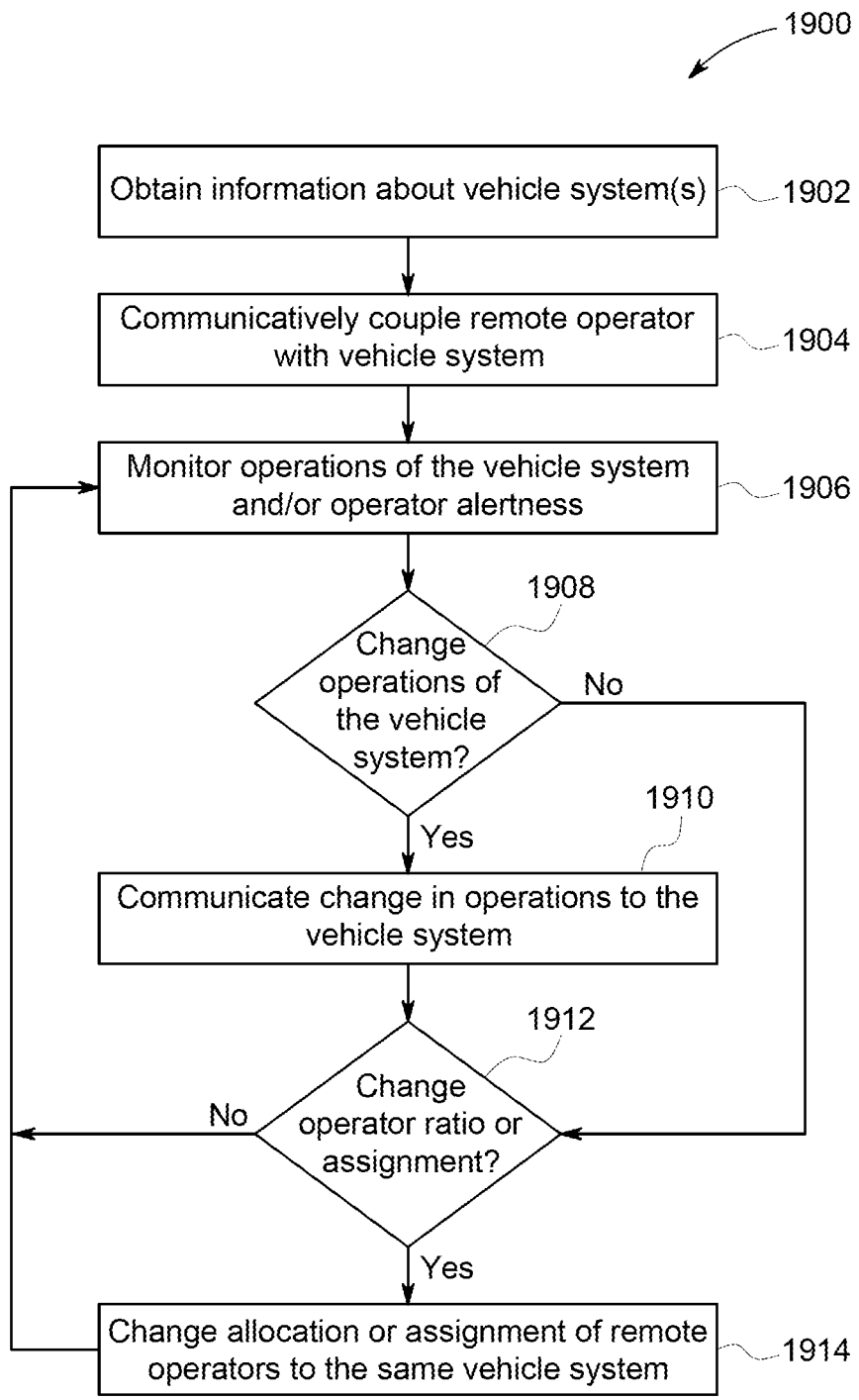
FIG. 19 illustrates a flowchart of one embodiment of a method for distributed vehicle system control.

FIG. 19 illustrates a flowchart of one embodiment of a method 1900 for distributed vehicle system control. The method 1900 may be performed by one or more embodiments of the control systems described herein. For example, the method 1900 can represent operations performed by one or more of the components of the vehicle control system and/or the remote-control system (such as the controllers, the alerter systems, the CRM units, etc.), as described above. In one embodiment, the method 1900 may represent or be used to create a software program for directing the operations of the vehicle control system and/or the remote-control system.

At 1902, information about one or more vehicle systems that are to be remotely controlled is obtained. This information can include make up information, which indicates or represents the vehicles in the vehicle systems (e.g., by model number, road number, horsepower capability, braking capability, etc.), the cargo carried by the vehicle systems, the scheduled routes to be taken by the vehicle systems, the schedules of the vehicle systems, etc. This information may be received from a variety of sources, such as a dispatch or scheduling facility, the vehicle systems themselves, or the like.

At 1904, a remote operator is communicatively coupled with at least one vehicle system. For example, the remote-control system can communicate one or more signals with the vehicle control system of the vehicle system via a communication network that includes and/or is formed from the communication devices. The assignment of which remote operator is to be communicatively coupled with the vehicle systems may be made based at least in part on the information received at 1902. Different off-board or remote operators may be associated with different geographic areas. For example, the vehicle systems traveling through a geographic area associated with a remote operator may be assigned to, communicatively coupled with, and remotely controlled by that remote operator during travel through that geographic area. But, the vehicle systems may be assigned to another, different remote operator responsive to exiting that geographic area or entering into another geographic area associated with the other, different remote operator. This can allow for different operators to become familiar with or have increased expertise with controlling movement of a vehicle system through different areas (relative to other operators), and assigning those operators to control the vehicle systems traveling in the areas associated with the operators.

At 1906, operations of the vehicle system and/or operator alertness are monitored. The operations of the vehicle system that are monitored can include throttle positions, brake settings, speeds, accelerations, etc. The operator alertness can be monitored by measuring physiological conditions of an onboard operator, such as respiration rate, heart rate, movements, glances, etc. In one aspect, 1906 can include receiving information from one or more operational systems and/or off-board systems. For example, the operations of the vehicle system may be monitored by receiving information about the vehicles and/or cargo included in the vehicle system.

At 1908, a determination is made as to whether operations of the vehicle system are to be changed. This determination may be made based on the vehicle system operations and/or the operator alertness that are monitored. For example, if the vehicle system is moving faster or slower than a designated speed, is operating with a different throttle and/or brake setting than designated by the remote-control system, or is otherwise deviating from a designated operation, the remote-control system may determine to change the operation of the vehicle system to return the vehicle system to moving according to the designated operation. As another example, if the onboard operator is no longer alert, then the remote-control system may decide to activate an alarm to contact the onboard operator, to change movement of the vehicle system, or otherwise modify how the vehicle system is operating. If operation of the vehicle system is to be changed, then flow of the method 1900 can proceed toward 1910. Otherwise, flow of the method 1900 can proceed toward 1912.

At 1910, the change in operation in the vehicle system is communicated from the remote-control system to the vehicle control system. This change in operation may be communicated as a designated set point or other instruction that is communicated via the communication devices to the vehicle control system. At 1912, a determination is made as to whether the operator ratio or assignment of the vehicle system is to be changed. The operator ratio represents the number of off-board operators controlling operations of the vehicle system. For example, an operator ratio may be calculated as the number of off-board or remote operators to the number of onboard operators controlling movement of the vehicle system, the number of off-board or remote operators to the total number of off-board and onboard operators controlling movement of the vehicle system, or another number. The operator ratio can be changed responsive to a change in operational circumstances or scenarios. For example, responsive to determining that the vehicle system is entering a more densely populated area than a previous area, the number of remote operators controlling and/or assisting in controlling the vehicle system may increase.

Responsive to determining that cargo carried by the vehicle system hazardous and/or has a higher priority than other vehicle systems, the number of remote operators controlling and/or assisting in controlling the vehicle system may increase. As another example, responsive to determining that the vehicle system is traveling in an area having increased traffic of other vehicle systems, that one or more components of the vehicle system have failed or are likely to fail, and/or that one or more onboard operators are no longer alert, the number of off-board operators controlling and/or assisting in controlling the vehicle system may increase. This may be done automatically by the remote and/or vehicle control system or manually by a supervisor or consensus of the remote operators.

In addition or as an alternate to changing the operator ratio, the operator assignment may be modified. The operator assignment is the indication of which vehicle system is being at least partially monitored and/or controlled by a remote operator. A remote operator can be assigned to several vehicle systems, as described above. The assignment of a remote operator to a vehicle system can be determined by the remote-control system, such as by determining which vehicle systems are traveling in (and/or are scheduled to travel into or through) a geographic area (e.g., geo-fence) associated with a remote operator (and then assigning those vehicle systems to the remote operator). As another example, the assignment of a remote operator can be determined based on which skills are needed to remotely control a vehicle system. Some vehicle systems may be carrying hazardous cargo, may be traveling through difficult terrain (e.g., a series of curves, urban areas, etc.), may be more difficult to control relative to other vehicle systems (e.g., due to the number of propulsion-generating vehicles, the weight of the cargo and/or vehicles, the age of the vehicles, etc.), may have systems or controls that require specialized training, or otherwise may require a set of skills that not all operators have.

As another example, the assignment of a remote operator can be determined based on a work history of the operator. An operator that has remotely monitored and/or controlled a particular vehicle system or a particular type of vehicle (e.g., based on model number, age, etc., of the propulsion-generating vehicles in the vehicle system) more than another operator may be assigned to remotely control that same vehicle system or type of vehicle system instead of the other operator. As another example, the assignment of a remote operator can be determined based on a current working shift of the operator. For example, if a remote operator is nearing the end of a contractually agreed upon or assigned work shift, another remote operator that has more available time during his or her work shift may be assigned to a vehicle system to avoid exceeding the work shift.

If the operator ratio or assignment is to change, then flow of the method 1900 may proceed toward 1914. Otherwise, flow of the method 1900 can return toward 1906. The method 1900 may proceed in a loop-wise manner until terminated, until completion of a trip of the vehicle system, and/or until a vehicle system being remotely controlled leaves the section of the route being controlled by the remote-control system.

At 1914, an allocation or assignment of remote operators controlling the same vehicle system is changed. For example, if the determination at 1912 reveals that more remote operators are needed to remotely control movement of a vehicle system, then one or more additional remote operators begin remotely controlling movement of the vehicle system. Conversely, if the determination at 1912 reveals that fewer remote operators are needed to remotely control movement of a vehicle system, then one or more remote operators currently controlling movement of the vehicle system are assigned to other tasks that do not include remotely controlling movement of the vehicle system.

In one embodiment, a distributed control system includes a remote-control system configured to be communicatively coupled with plural separate vehicle systems. The remote-control system is configured to remotely control operation of the vehicle systems and/or communicate with the local vehicle control system or operator. The remote-control system also is configured to one or more of change how many of the vehicle systems are concurrently controlled by the remote-control system or change how many remote operators of the remote-control system concurrently control the same vehicle system of the vehicle systems.

In one example, the remote-control system is configured to control the operation of the vehicle systems without any operator disposed onboard the vehicle systems during movement of the vehicle systems.

In one example, the remote-control system is configured to control the operation of the vehicle systems by designating operations of the vehicle systems and communicating instructions to onboard operators of the vehicle systems to implement the designated operations. The designated operations include one or more of designated throttle positions, designated brake settings, or designated speeds.

Optionally, the remote-control system is configured to remotely control the movements of the vehicle systems by providing operating parameters and limits on the movements of the vehicle systems. The operating parameters can include one or more of designated speeds, designated throttle settings, or designated brake settings. The limits can include one or more of designated upper limits on speeds, designated upper limits on throttle settings, designated lower limits on speeds, or designated lower limits on throttle settings.

In one example, the remote-control system is configured to change a number of vehicle systems the remote operator concurrently controls based on an operating state of the vehicle systems being concurrently controlled or based on operator input.

In one example, the operating state includes the vehicle system entering into or approaching a particular geographic region of interest.

In one example, the operating state includes the vehicle system transporting hazardous cargo or has another high-risk attribute.

In one example, the remote-control system is configured to remotely control the operation of the vehicle systems via one or more wireless networks.

In one example, the remote-control system is configured to remotely control the operation of the vehicle systems by designating operational set points that vehicle control systems disposed onboard the vehicle systems are to one or more of maintain or use as upper limits on operations of the vehicle systems.

In one example, the remote-control system includes an alerter system configured to obtain sensor data from one or more sensor arrays that monitor one or more of physiological conditions of one or more onboard operators or off-board operators of the vehicle systems or movements of the one or more onboard operators or off-board operators. The alerter system is configured to determine whether the one or more onboard operators or off-board operators are controlling the operation of the vehicle system based on the sensor data.

In one example, the sensor data includes one or more of images or video of the one or more onboard operators or off-board operators.

In one example, the sensor data includes one or more of pulse rates, respiration rates, blood pressures, or movements of the one or more onboard operators or off-board operators.

In one example, the sensor data includes one or more of electroencephalogram (EEG) data, electrocardiogram (ECG) data, or other contact/wearable measurements of the one or more onboard operators or off-board operators.

In one example, the alerter system is configured to obtain the sensor data from the one or more sensor arrays that monitor the one or more physiological conditions of one or more onboard operators. The alerter system can be configured to communicate the sensor data to one or more off-board operators at the remote-control system.

In one example, the alerter system is configured to obtain the sensor data from the one or more sensor arrays that monitor the one or more physiological conditions of one or more off-board operators. The alerter system can be configured to communicate the sensor data to one or more onboard operators at the remote-control system.

In one example, the alerter system is configured to examine the sensor data and expected operator behavior representative of operator awareness in a vehicle context.

In one example, the remote-control system is configured to receive make up information of at least one of the vehicle systems from a dispatch facility and to be assigned to remotely control the at least one of the vehicle systems based on the make up information. In one embodiment, a method includes communicatively coupling a remote-control system with plural separate vehicle systems, generating control inputs from the remote-control system to remotely control operation of the vehicle systems, and one or more of changing how many of the vehicle systems are concurrently controlled by the remote-control system or changing how many remote operators of the remote-control system concurrently control the same vehicle system of the vehicle systems.

In one example, the method also includes remotely controlling the operation of the vehicle systems by communicating the control inputs to the vehicle systems without any operator disposed onboard the vehicle systems during movement of the vehicle systems.

In one example, the control inputs designate operations of the vehicle systems. The method also can include communicating the control inputs to onboard operators of the vehicle systems to implement the designated operations. The designated operations can include one or more of designated throttle positions, designated brake settings, or designated speeds.

In one example, the method also includes changing a number of the remote operators that concurrently control the same vehicle system of the vehicle systems based on an operating state of the vehicle system being concurrently controlled.

In one example, the operating state includes the vehicle system entering into or approaching a densely populated area.

In one example, the operating state includes the vehicle system transporting hazardous cargo.

In one example, the method also includes communicating the control inputs from the remote-control system to the vehicle systems via one or more satellites.

In one example, the control inputs include designated operational set points that vehicle control systems disposed onboard the vehicle systems are to one or more of maintain or use as upper limits on operations of the vehicle systems.

In one example, the method also includes monitoring one or more of physiological conditions of onboard operators of the vehicle systems or movements of the onboard operators, and determining whether one or more of the onboard operators are controlling the operation of the vehicle system based on the sensor data.

In one example, the sensor data includes one or more of images or video of the onboard operators.

In one example, the sensor data includes one or more of pulse rates, respiration rates, blood pressures, or movements of the onboard operators.

In one embodiment, a distributed control system includes a vehicle control system configured to be disposed onboard a vehicle system formed from one or more vehicles. The vehicle control system is configured to control movement of the vehicle system. The distributed control system also includes a remote-control system configured to be communicatively coupled with the vehicle control system. The remote-control system is configured to communicate control inputs from one or more off-board operators of the remote-control system to the vehicle system in order to remotely control the movement of the vehicle system. The remote-control system is configured to change how many of the off-board operators concurrently generate the control inputs for communication from the remote-control system to the vehicle control system for remote-control of the vehicle system.

In one embodiment, a vehicle control system includes a controller configured to be disposed onboard a vehicle system and to be communicatively coupled with one or more of a propulsion system or a braking system of the vehicle system. The controller is configured to receive operational set points designated by an operator located onboard the vehicle system and to determine operational settings of the one or more of the propulsion system or the braking system that drives the vehicle system to move according to the operational set points designated by the operator.

In one example, the operational set points include designated speeds.

In one example, the operational settings include throttle positions.

One or more embodiments of the inventive subject matter described herein relate to systems and methods that enable control of movement of a vehicle system to transfer between one or more of an onboard vehicle control system and a remote-control system for one of the onboard vehicle control system or the remote-control system to control the movement of the vehicle system. The systems and methods communicatively link the remote-control system and the onboard vehicle control system and transfer control of the movement of the vehicle system based on one or more of a location, a condition of the vehicle system, or an operator request and/or condition. The location may be a geographic area or designated segment of a route which is either known a priori or calculated according to some track and/or region characteristics. For example, these areas may be based on population density, track work locations, grade crossing locations, vehicle work locations (e.g., pick-up or set-out of vehicles), a designated practice area for manual control of the vehicle system, or the like. The condition may be a fault state of the vehicle system, a communication loss between the vehicle system and the remote-control system, an increase in a rate of fuel consumption, or the like. The systems and methods lock out onboard operator control of the vehicle system, receive an instruction from the remote-control system to test an operation of the vehicle system, and communicate visual data representative of an area outside of the vehicle system when control of the movement of the vehicle system transfers to the remote-control system. The systems and methods automatically stop the vehicle system if needed, activate the onboard vehicle control system and disconnect communication with the remote-control system when control of the movement of the vehicle system transfers to the onboard vehicle control system.

This subject matter may be used in connection with rail vehicles and rail vehicle systems, or alternatively may be used with other types of vehicles. For example, the subject matter described herein may be used in connection with automobiles, trucks, mining vehicles, other off-highway vehicles (e.g., vehicles that are not designed or are not legally permitted for travel on public roadways), aerial vehicles (e.g., fixed wing aircraft, drones or other unmanned aircraft, etc.), or marine vessels.

The vehicle consist or vehicle system can include two or more vehicles mechanically coupled with each other to travel along a route together. Optionally, the vehicle system can include two or more vehicles that are not mechanically coupled with each other, but that travel along a route together. For example, two or more automobiles may wirelessly communicate with each other as the vehicles travel along the route together as a vehicle system to coordinate movements with each other. Optionally, a vehicle system or consist may be formed from a single vehicle.

Figure 20:
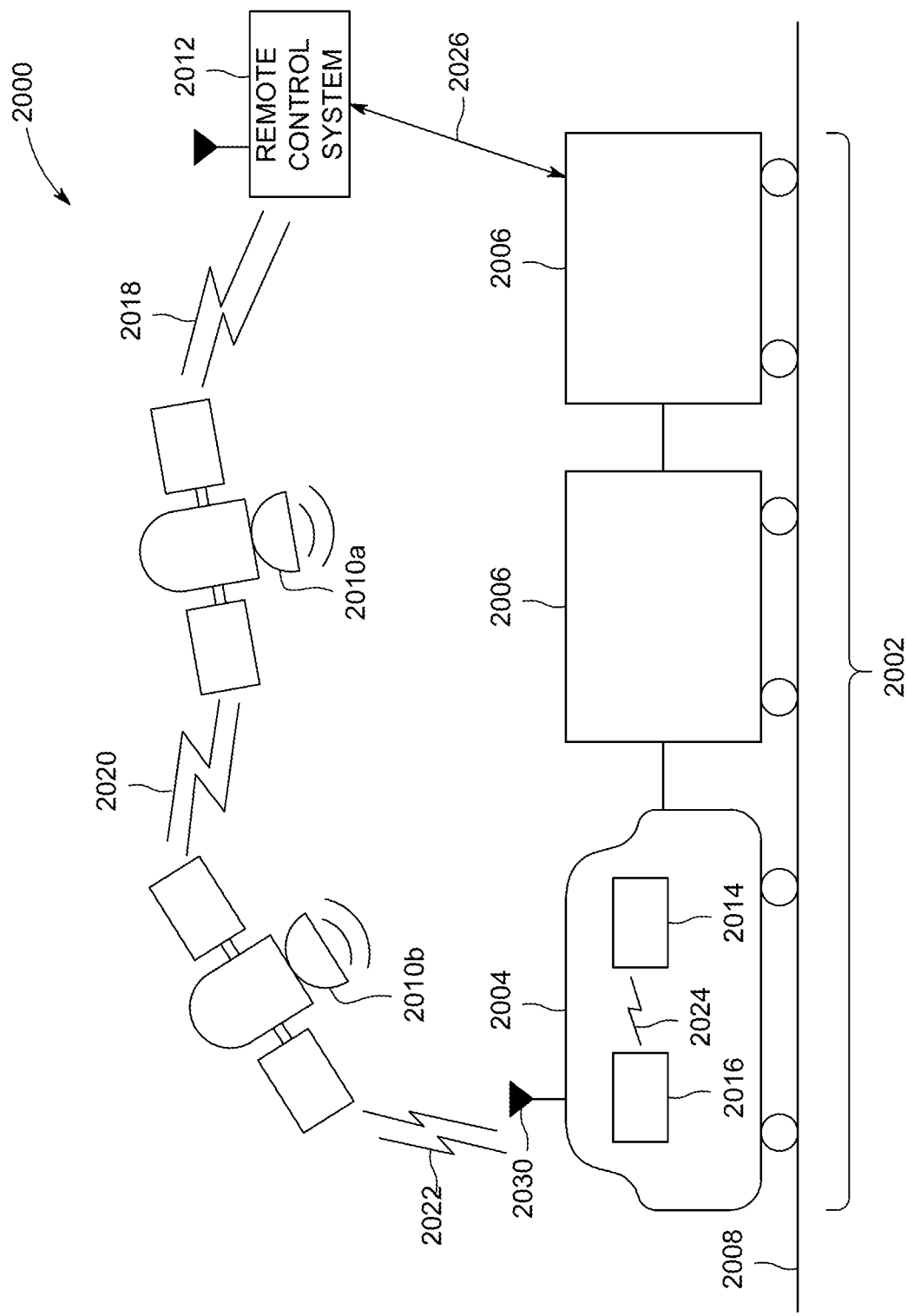
FIG. 20 illustrates a schematic illustration of a control system of a vehicle system in accordance with one embodiment.

FIG. 20 illustrates one embodiment of a vehicle control system 2000 used to control movement of a vehicle system 2004. The vehicle system 2004 can represent one or more of the other vehicle systems shown and/or described herein.

The illustrated vehicle system 2004 includes a propulsion-generating vehicle 2004 and non-propulsion-generating vehicles 2006 that travel together along a route 2008. Although the vehicles 2004, 2006 are shown as being mechanically coupled with each other, optionally the vehicles may not be mechanically coupled with each other.

The propulsion-generating vehicle 2004 is shown as a locomotive, the non-propulsion-generating vehicles 2006 are shown as rail cars, and the vehicle system 2004 is shown as a train in the illustrated embodiment. Alternatively, the vehicles 2004, 2006 may represent other vehicles such as automobiles, marine vessels, or the like, and the vehicle system 2004 can represent a grouping or coupling of these vehicles. The number and arrangement of the vehicles 2004, 2006 in the vehicle system 2004 are provided as one example and are not intended as limitations on all embodiments of the subject matter described herein.

The vehicle system includes an onboard vehicle control system (OVCS) 2014. The OVCS can include hardware circuits or circuitry that include and/or are connected with one or more processors (e.g., one or more microprocessors, field programmable gate arrays, and/or integrated circuits). The OVCS can control or limit movement of the propulsion-generating vehicle 2004 and/or the vehicle system 2004 that includes the vehicles 2004, 2006 based on one or more limitations. For example, the OVCS can prevent the vehicles and/or the vehicle system from entering a restricted area, can prevent the vehicle and/or vehicle system from exiting a designated area, can prevent the vehicle and/or vehicle system from traveling at a speed that exceeds an upper speed limit, can prevent the vehicle and/or vehicle system from traveling at a speed that is less than a lower speed limit, can prevent the vehicle and/or vehicle system from traveling according to a designated trip plan generated by an energy management system, or the like. The OVCS will be discussed in more detail with FIG. 19.

The propulsion-generating vehicle 2004 includes a control mediation system 2016 disposed onboard the vehicle 2004. The control mediation system represents hardware circuitry that includes and/or is connected with one or more processors (e.g., microprocessors, controllers, field programmable gate arrays, integrated circuits, or the like). The control mediation system is operably connected with the OVCS of the vehicle 2004 by a communication link 2024. The communication link 2024 may represent a wired or wireless connection. Optionally, the control mediation system may be disposed off-board the vehicle system 2004 and may wirelessly communicate with the OVCS. Additionally or alternatively, the vehicle system 2004 may include one or more additional propulsion-generating vehicles wherein the one or more additional propulsion-generating vehicles may include a control mediation system. For example, the vehicle system may include two or more propulsion-generating vehicles 2004 where one or more, or each, of the vehicles includes a control mediation system. Optionally, the vehicle system 2004 may include two or more propulsion-generating vehicles 2004 wherein only one vehicle 2004 includes a control mediation system.

The control mediation system is operably connected with a remote-control system that is disposed off-board the vehicle system 2004. The remote-control system can represent one or more of the remote-control systems described herein, and can remotely control movement of the vehicle system 2004 by communicating movement operational settings to the control mediation system 2116 onboard the vehicle 2004. Multiple operators at the remote-control system can remotely control the movement of the vehicle system 2004. For example, multiple operators may remotely control multiple, different moving heavy vehicles (e.g., trains, vessels, automobiles, or the like).

The remote-control system is separated from the vehicle system 2004 by a distance 2026. The distance may be 50 meters, 500 meters, 500 kilometers, 5000 kilometers, or the like. The distance between the vehicle system 2004 and the remote-control system can be beyond a line of site of an operator of the remote-control system to the vehicle system 2004, can extend between different time zones, can extend between different geographical locations (e.g., different town, county, state, country) or the like. For example, an operator of the remote-control system may control the movement of the vehicle system 2004 when the operator of the remote-control system is located in New York and the vehicle system 2004 is located in Utah. Alternatively, the distance may be within a line a site of an operator of the remote-control system to the vehicle system 2004. For example, the distance may be less than 50 meters.

The remote-control system is communicatively linked with the OVCS of the vehicle 2004 by communication links established between the remote-control system and the vehicle system 2004. For example, the remote-control system communicates control signals to a first communication device 2010 (e.g., a first satellite 2010a) by the communication link 2018. The first satellite 2010a communicates the control signals to a second communication device 2010 (e.g., a second satellite 2010b) by the communication link 2020. The second satellite 2010b communicates the control signals to the control mediation system 2016 onboard the vehicle system 2004 by the communication link 2022. Optionally, less than two or more than two satellites may be used to communicate signals between the remote-control system and the vehicle system 2004. Additionally or alternatively, the vehicle system 2004 may communicate with the remote-control system with terrestrial communications repeaters (e.g., radio towers). Optionally, the vehicle system 2004 and remote-control system may communicate by communication links established between one or more satellites and/or one or more radio towers, or the like. Additionally, the remote-control system is communicatively linked with the OVCS by the communication link 2024 established between the control mediation system and the OVCS. For example, the control mediation system communicates the control signals between the remote-control system (e.g., by communication links 2018, 2020, 2022) and the OVCS (e.g., by the communication link 2024).

The remote-control system communicates control signals to the vehicle system 2004 by the communication links in order to remotely control the movement of the vehicle system 2004 as the vehicle system 2004 travels along the route 2008. The control signals dictate the movement operational settings of the vehicle system 2004 that include one or more of a throttle notch setting, a brake setting, speed setting or the like. The remote-control system will be described in further detail below with FIG. 22.

The one or more processors of the control mediation system communicatively link the remote-control system disposed off-board the vehicle system with the OVCS disposed onboard the vehicle system 2004. The one or more processors of the control mediation system mediate a process of transferring control of the movement of the vehicle system 2004 from the remote-control system to the OVCS or from the OVCS to the remote-control system. For example, the control mediation system mediates (e.g., manages, arbitrates, or the like) which system controls the vehicle system 2004 to ensure the movement of the vehicle system 2004 is controlled by a single system at a given time. For example, when control of the movement of the vehicle system is managed by the remote-control system, the movement of the vehicle system 2004 cannot be controlled autonomously by the OVCS or manually by an operator onboard the vehicle system 2004. Additionally, when control of the movement of the vehicle system 2004 is managed by the OVCS (manually or autonomously), the movement of the vehicle system 2004 cannot be controlled by the remote-control system.

Control of the movement of the vehicle system 2004 may transfer from the remote-control system to the OVCS or from the OVCS to the remote-control system based on a location and/or region, if vehicle system 2004 experiences a certain condition, based on the request and/or condition of the operators of the vehicle system 2004, or the like. The location is a designated geographic area or a designated segment of the route 2008. The location may be a length of the route (e.g., 10 kilometers, 50 kilometers, or the like), may be a geographic area (e.g., a town, a county, a state, or the like), may be a predetermined or a non-predetermined length and/or geographic area (e.g., determined prior to or during transit of the vehicle system 2004) which is either known a priori or calculated according to some track and/or region characteristics, or the like. For example, these areas may be based on population density, track work locations, grade crossing locations, vehicle work locations (e.g., pick-up or set-out of vehicles), a designated practice area for manual control of the vehicle system 2004, or the like.

Additionally, control of the movement of the vehicle system 2004 may transfer from the remote-control system to the OVCS or from the OVCS to the remote-control system based on a condition of the vehicle system 2004. For example, the condition may be a fault state of the vehicle system 2004, may be a communication loss between the vehicle system 2004 and the remote-control system, may be by request of the local or remote operator, may be a lack of alertness or other physical condition of the local and/or remote operator, or the like. Methods determining if control of the vehicle system 2004 is to transfer from one system to another, and transferring control of the vehicle system will be discussed below in more detail pertaining to FIGS. 23 and 24.

Figure 21:
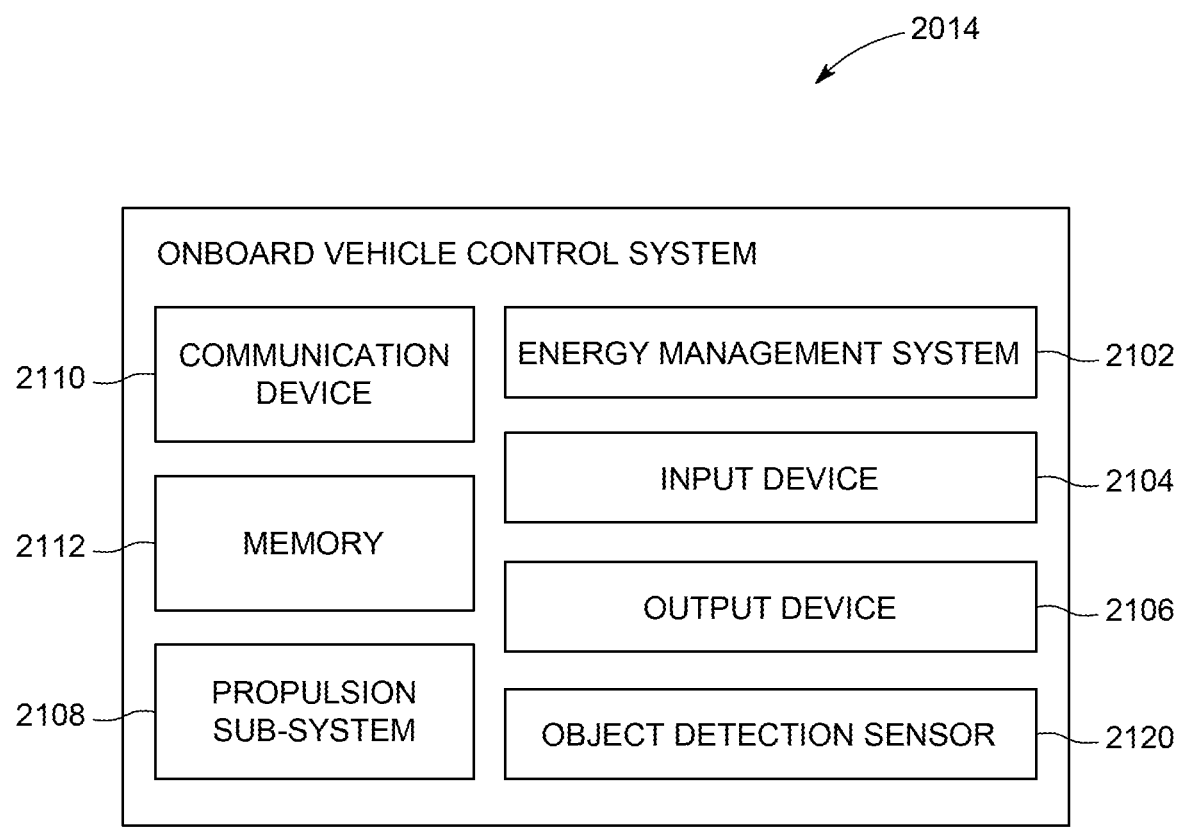
FIG. 21 illustrates a schematic illustration of an onboard vehicle control system for a propulsion-generating vehicle in accordance with one embodiment.

FIG. 21 is a schematic illustration of the onboard vehicle control system (OVCS) 2014 disposed onboard the vehicle 2004 in accordance with one embodiment. The OVCS controls the movement of the vehicle system 2004. The OVCS may be one or more of controlled manually (e.g., by of an operator onboard the vehicle 2004) and/or autonomously with an energy management system (EMS) 2102. The OVCS can include or represent one or more hardware circuits or circuitry that include, are connected with, or that both include and are connected with one or more processors, controllers or other hardware logic-based devices. For example, an operator onboard the vehicle 2004 may manually control movement of the vehicle system 2004 by manually controlling the hardware, controllers, devices, or the like of the OVCS. Additionally or alternatively, the EMS may autonomously control movement of the vehicle system 2004 (e.g., without input by an operator onboard the vehicle system 2004) by electrically communicating directions and/or commands to the systems and devices associated with the OVCS 2114.

The EMS can include hardware circuits or circuitry that include and/or are connected with one or more processors. The EMS can create a trip plan for trips of the vehicles 2004, 2006 and/or the vehicle system 2004 that includes the vehicles 2004, 2006. A trip plan may designate operational settings of the propulsion-generating vehicle and/or the vehicle system as a function of one or more of time, location, or distance along a route for a trip. Traveling according to the operational settings designated by the trip plan may reduce fuel consumed and/or emissions generated by the vehicles and/or the vehicle system 2004 relative to the vehicles and/or vehicle system traveling according to other operational settings that are not designated by the trip plan. The identities of the vehicles in the vehicle system 2004 may be known to the EMS so that the EMS can autonomously control operations of the vehicle system 2004. Additionally, the EMS can determine what operational settings to designate for a trip plan to achieve a goal of reducing fuel consumed and/or emissions generated by the vehicle system during the trip.

The OVCS is connected with an input device 2104 and an output device 2106. The OVCS can receive manual input from an operator of the propulsion-generating vehicle 2004 through the input device, such as a touchscreen, keyboard, electronic mouse, microphone, or the like. For example, the OVCS can receive manually input changes to the tractive effort, braking effort, speed, power output, and the like, from the input device. The OVCS 2514 may receive a single instance of an actuation of the input device to initiate the establishment of a communication link between the OVCS and the control mediation system.

The OVCS can present information to the operator of the vehicle using the output device, which can represent a display screen (e.g., touchscreen or other screen), speakers, printer, or the like. For example, the OVCS can present the identities and statuses of other vehicles in the vehicle system, identities of missing vehicles (e.g., those vehicles from which the vehicle has not received the status), contents of one or more command messages, or the like. The output device provides a notification signal to the operator of the vehicle that automatically informs (e.g., notifies) the operator of the vehicle that control of the movement of the vehicle system has changed. For example, the output device may change colors, change a display format, ring a bell, communicate a vocal command, communicate a sound, or the like that the control of the movement of the vehicle system is and/or has transferred one or more of to the remote-control system or to the OVCS. Optionally, the output device can present instructions to the operator onboard the vehicle system from the OVCS that instruct the operator how to manually control the movement of the vehicle system. For example, the output device may instruct a throttle notch setting, speed setting, brake setting, or the like, to the operator of the vehicle system for the operator onboard the vehicle system to manually control the movement of the vehicle system.

The OVCS is connected with a propulsion subsystem 2108 of the propulsion-generating vehicle. The propulsion subsystem can represent one or more of the propulsion systems described and/or shown herein. The propulsion subsystem provides tractive effort and/or braking effort of the propulsion-generating vehicle. The propulsion subsystem may include or represent one or more engines, motors, alternators, generators, brakes, batteries, turbines, and the like, that operate to propel the propulsion-generating vehicle and/or the vehicle system under the manual or autonomous control that is implemented by the OVCS. For example, the OVCS can direct operations of the propulsion subsystem by the OVCS generating control signals autonomously or based on manual input by an operator.

The OVCS is connected with a memory 2112 and a communication device 2110. The memory can represent an onboard device that electrically and/or magnetically stores data. For example, the memory may represent a computer hard drive, random access memory, read-only memory, dynamic random access memory, an optical drive, or the like. The communication device includes or represents hardware and/or software that is used to communicate with other vehicles in the vehicle system. For example, the communication device may include a transceiver and associated circuitry (e.g., antenna 2030 of FIG. 20) for wirelessly communicating (e.g., communicating and/or receiving) linking messages, command messages, reply messages, repeat messages, or the like. Optionally, the communication device includes circuitry for communicating messages over a wired connection, such as an electric multiple unit (eMU) line of the vehicle system (not shown), catenary or third rail of electrically powered vehicles, or another conductive pathway between or among the vehicles of the vehicle system 2004 and/or between or among vehicles of a different vehicle system.

The OVCS may control the communication device by activating the communication device. The OVCS can examine the messages that are received by the communication device from one or more of the control mediation system or other vehicles in the vehicle system.

The OVCS is connected with an object detection sensor 2120. The object detection sensor can include hardware circuits or circuitry and/or software that include and/or are connected with one or more processors. The detection sensor can obtain sensor data that is indicative of an area outside of the vehicle system. For example, the detection sensor may obtain sensor data in an area in front of the vehicle system in a direction of travel of the vehicle system, in an area behind the vehicle system in a direction of travel of the vehicle system, or the like. The detection sensor may include a camera that obtains still and/or motion visual data of an area of the route in the direction of travel of the vehicle system and/or in a direction opposite the direction of travel of the vehicle system. For example, the detection sensor may be one or more cameras that capture still images in the front (e.g., in the direction of travel) and the rear (e.g., opposite the direction of travel) of the vehicle system. Optionally, the detection sensor may be a radar system that sends and receives pulses reflected off of an object in order to detect a presence of an object in an area outside of the vehicle system. Optionally, the detection sensor may be an alternative sensing system that obtains data of an area outside of the vehicle system. The detection sensor may obtain data (e.g., visual, statistical, radar, or the like) a distance of 2 meters, 25 meters, 100 meters, 500 meters, 1000 meters, or the like outside of and in a direction away from the vehicle system.

The object detection sensor may include one or more sensing devices positioned around the vehicle on one or more of the interior and/or exterior of the vehicle (not shown). For example, a sensing device may be positioned on a front and/or rear end of the vehicle to obtain data for the vehicle and/or the vehicle system that travels in a first direction and an opposite second direction (e.g., back and forth). Optionally, one or more sensing devices may be used, and the placement of the one or more sensing devices may vary.

Figure 22:
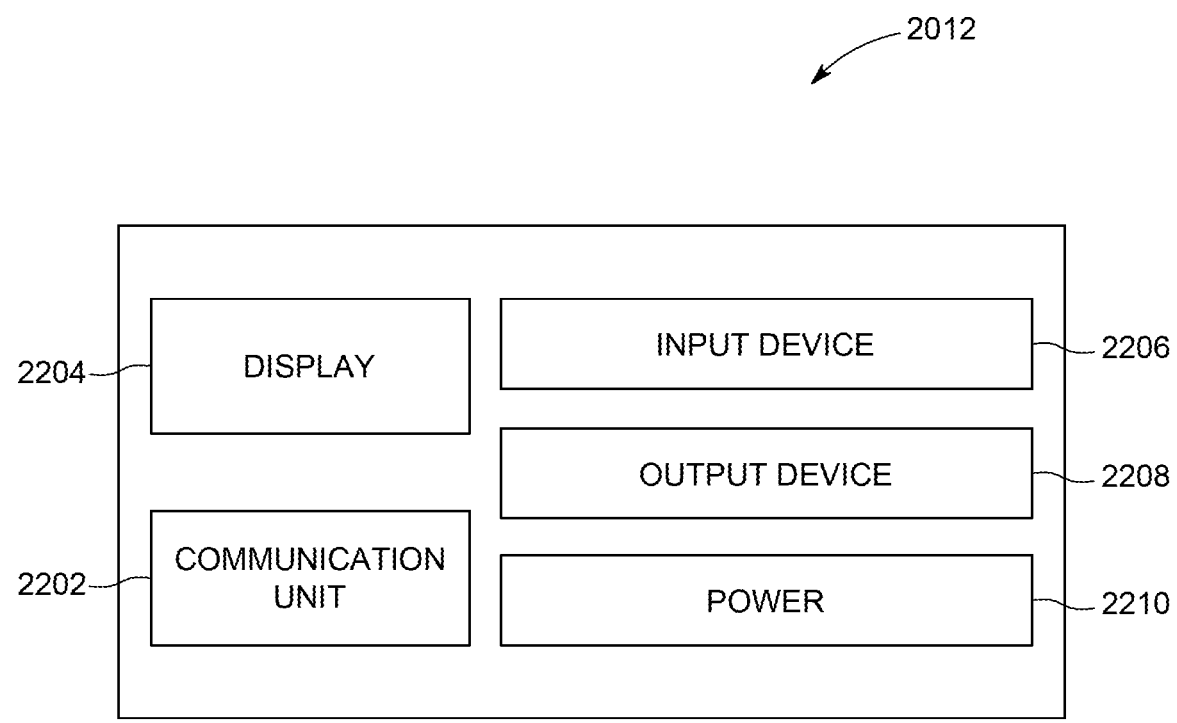
FIG. 22 illustrates a schematic illustration of a remote-control system in accordance with one embodiment.

FIG. 22 is a schematic illustration of the remote-control system 2012 of FIG. 20. The remote-control system remotely controls movement of the vehicle system 2004. For example, the remote-control system remotely controls movement of the vehicle system by communicating with the control mediation system by the communication links. The remote-control system represents hardware circuitry that includes and/or is connected with one or more processors (e.g., microprocessors, controllers, field programmable gate arrays, integrated circuits, or the like).

The remote-control system generates control signals that are communicated by a communication unit 2202. The control signals remotely control movement of the vehicle system 2004. The communication unit 2202 can one or more of send or receive communication signals with the vehicle system by the communication links between the control mediation system and the remote-control system. The remote-control system receives one or more of image data and/or sensor data detected by the object detection sensor onboard the propulsion-generating vehicle. For example, the remote-control system may receive visual data obtained by the detection sensor and communicated by the control mediation system that is representative of an area outside of the vehicle system. Optionally, the remote-control system may receive status notifications such as vehicle system equipment statuses, current vehicle and/or vehicle system operational settings, vehicle system location, or the like, of the vehicles and/or of the vehicle system.

The remote-control system can include one or more input devices 2206 and/or output devices 2208 such as a keyboard, an electronic mouse, stylus, microphone, touch pad, or the like. Additionally or alternatively, the input and/or output devices may be used to communicate with one or more of an operator of the vehicle system or the OVCS. The remote-control system can include one or more displays 2204 such as a touchscreen, display screen, electronic display, or the like. The displays may visually, graphically, statistically, or the like, display information to the operator of the remote-control system. The remote-control system is operably connected with components of the vehicle system. Additionally or alternatively, the remote-control system may be operably connected with components or alternative systems onboard and/or off-board the vehicle system.

The remote-control system can include a power unit 2210. The power unit powers the remote-control unit. For example, the power unit may be a battery and/or circuitry that supplies electrical current to power other components of the remote-control system. Additionally or alternatively, the power unit may provide electrical power to one or more other systems.

Returning to FIG. 20, the remote-control system is configured to remotely control movement of the vehicle system by sending control signals to the OVCS onboard the vehicle via the control mediation system. Additionally, the OVCS is configured to control movement of the vehicle system one or more of autonomously or manually by an operator onboard the vehicle system. The one or more processors of the control mediation system control which of the remote-control system or the OVCS controls the movement of the vehicle system at a given time. Additionally, the control mediation system mediates the transfer of control of the movement of the vehicle system from the remote-control system to the OVCS or from the OVCS to the remote-control system.

Figure 23:
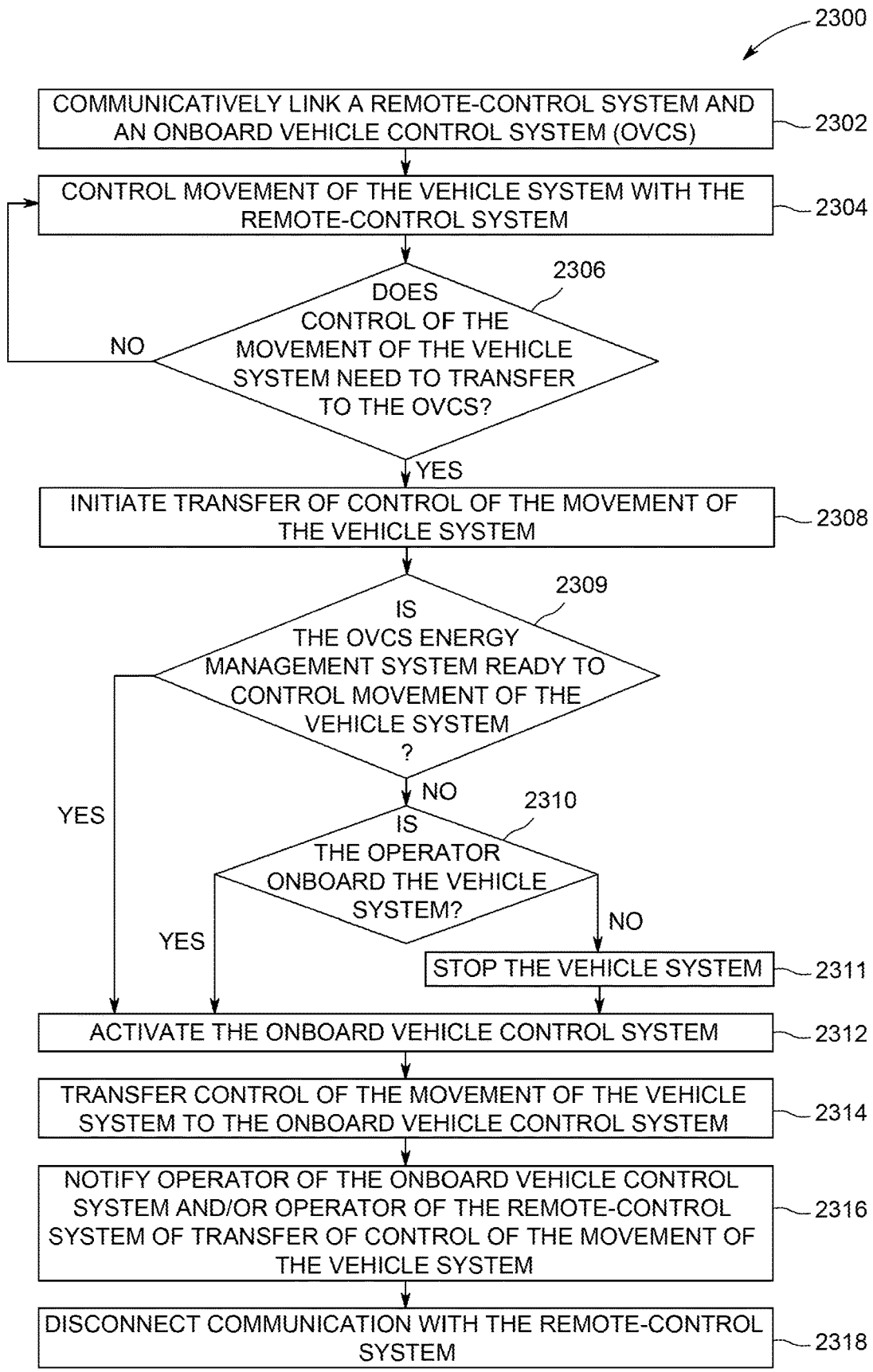
FIG. 23 illustrates a flowchart of a method for transferring control of movement of a vehicle system from a remote-control system to an onboard vehicle control system in accordance with one embodiment.

FIG. 23 illustrates a flowchart of a method 2300 for transferring control of the movement of the vehicle system from the remote-control system to the OVCS. The steps of the method 2300 may be completed one or more of prior to or during the transfer of control of the movement of the vehicle system from the remote-control system to the OVCS.

At 2302, the remote-control system is communicatively linked to the OVCS via the control mediation system. For example, the remote-control system is communicatively linked to the control mediation system by the communication links and the OVCS is communicatively linked to the control mediation system by the communication link.

At 2304, control of the movement of the vehicle system is controlled by the remote-control system. For example, when control of the movement of the vehicle system is controlled by the remote-control system, an operator or autonomous controller (e.g., the EMS) onboard the vehicle system is unable to control the movement of the vehicle system. The remote-control system remotely controls the movement of the vehicle system by communicating control signals to the OVCS. The control signals dictate the movement operational settings of the vehicle system that include one or more of a throttle notch setting, a brake setting, speed setting or the like. For example, one or more operators of the remote-control system may send a control signal to the OVCS via the control mediation system directing the OVCS to increase the speed of the vehicle system to 75 kilometers per hour. Responsive to receiving the control signal, the OVCS directs the propulsion subsystem to increase the throttle notch setting to adhere to the 75 kph speed direction.

At 2306, a decision is made to determine if control of the movement of the vehicle system needs to transfer from the remote-control system to the OVCS. The decision is based on one or more of a location, a condition of the vehicle system, or an operator (e.g., onboard or off-board) request and/or condition. For example, the control of the movement of the vehicle system may need to transfer to the OVCS if the vehicle system is traveling in a congested region (e.g., a town, a city). Optionally, the location of the vehicle system may be any alternative location that may benefit by the OVCS controlling the movement of the vehicle system.

Alternatively, the control of the movement of the vehicle system may transfer to the OVCS if the vehicle system has experienced a fault state. For example, one or more of the onboard vehicle control systems of the propulsion-generating vehicles may have identified an airbrake failure of the propulsion subsystem. Optionally, the vehicle system may have experienced a communication loss with the remote-control system. For example, one or more of the communication links may have been compromised. Optionally, the condition of the vehicle system may be any alternative condition that would benefit by the OVCS controlling the movement of the vehicle system.

Alternatively, the control of the movement of the vehicle system may transfer to the OVCS if the operator of the remote-control system or the operator of the OVCS has initiated a request to transfer control of the movement of the vehicle system to the OVCS. For example, the off-board operator of the remote-control system may reach a work end time and need to transfer control of the movement of the vehicle system to the OVCS for manual and/or autonomous control. Optionally, the off-board operator of the remote-control system may have a decrease in alertness prohibiting the off-board operator from safely controlling the movement of the vehicle system. Optionally, the request and/or condition of the operator onboard the vehicle system and/or the operator of the remote-control system may be any alternative request or condition that would benefit by the OVCS controlling the movement of the vehicle system.

If control of the movement of the vehicle system does not need to transfer to the OVCS, then flow of the method returns to 2304 and the remote-control system continues to remotely control the movement of the vehicle system. If control of the movement of the vehicle system does need to transfer to the OVCS, then flow of the method proceeds to 2308.

At 2308, transfer of control of the movement of the vehicle system from the remote-control system to the OVCS is initiated. The transfer of control may be initiated by one or more of an operator of the remote-control system, an operator onboard the vehicle system, or autonomously by the OVCS. At 2309, a determination is made if the OVCS energy management system (EMS) is ready to autonomously control the movement of the vehicle system. For example, the EMS can automatically control the movement of the vehicle system without operator intervention. The EMS may not be ready to autonomously control the movement of the vehicle system if the vehicle system is in a particular location/region, the vehicle system has experienced a certain condition, or based on the request and/or condition of the local or remote operators. For example, the EMS may not be ready to autonomously control the movement of the vehicle system if the vehicle system is traveling through a congested area. Optionally, if the EMS is not ready to control the movement of the vehicle system, the EMS may automatically present instructions to the operator onboard the vehicle system instructing the operator how to control the movement of the vehicle system. If the EMS is ready to control the movement of the vehicle system, then flow of the method proceeds toward. If the EMS is not ready to autonomously control the vehicle system, then flow of the method proceeds toward 2310.

At 2310, a determination is made if an operator is onboard the vehicle system. If an operator is not onboard the vehicle system, then flow of the method proceeds to 2311 wherein the vehicle system stops in order to allow an operator to board the vehicle system and flow of the method proceeds to 2312. If an operator is onboard the vehicle system, flow of the method proceeds toward 2312.

At 2312, the OVCS is activated to allow for one or more of manual or autonomous control of the movement of the vehicle system. For example, the OVCS may be in a setting for control by only the remote-control system prior to transferring control of the movement of the vehicle system. The OVCS may be activated to a second, different setting to allow for control of the vehicle system by the OVCS (e.g., autonomous and/or manual control). The OVCS may be activated to allow the operator onboard the vehicle system to manually control the movement of the vehicle system. Optionally, the OVCS may be activated to allow the EMS to automatically control the movement of the vehicle system without intervention by the operator.

At 2314, the one or more processors of the control mediation system completes the transfer of control of the movement of the vehicle system from the remote-control system. For example, the control mediation system may lock out or prevent control signals communicated by the remote-control vehicle from being received by the OVCS.

At 2316, one or more of the operator onboard the vehicle system, the one or more operators of the remote-control system, or an operator of an alternative system are notified that the transfer of control of the movement of the vehicle system is complete. For example, the operator onboard the vehicle system 2004 may be notified by the output device changing to a different color, changing to a different display format, sounding a bell, communicating a vocal command, communicating a sound, by the OVCS changing and/or dimming the interior lights of the vehicle, or the like. Optionally, the operator onboard the vehicle system may be notified by any alternative method. The one or more operators of the remote-control system may be notified that the transfer of control of the movement of the vehicle system is complete by one or more of the display or the output device changing to a different color, changing to a different display format, sounding a bell, communicating a vocal command, communicating a sound, or the like. Optionally, the one or more operators of the remote-control system may be notified by any alternative method.

At 2318, the OVCS disconnects communication with the remote-control system. For example, the control mediation system breaks the communication links between the remote-control system and the vehicle system. Optionally, the communication links may remain intact and the one or more processors of the control mediation system may prohibit control signals communicated by the remote-control system from being delivered to the OVCS.

Figure 24:
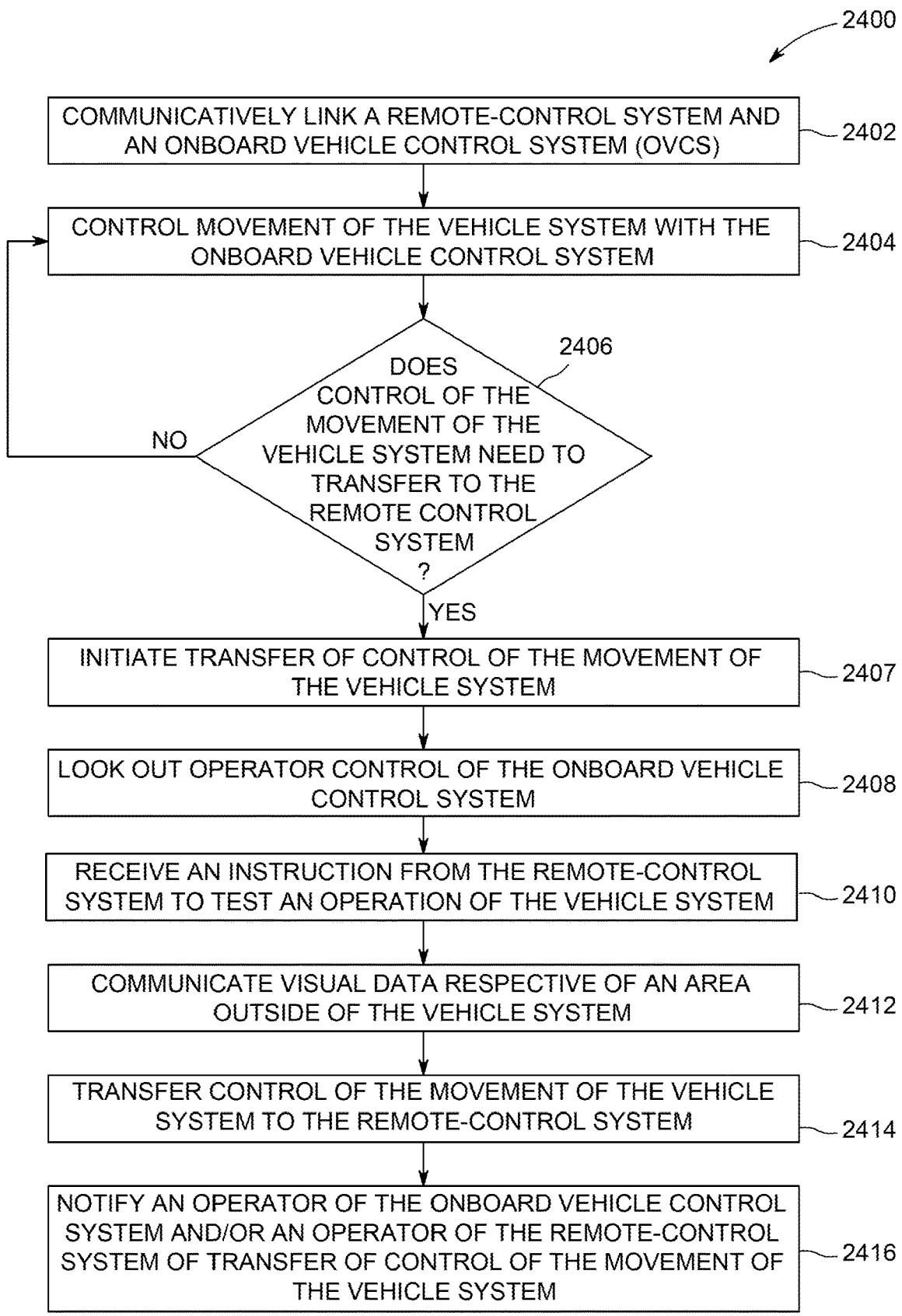
FIG. 24 illustrates a flowchart of a method for transferring control of movement of a vehicle system from an onboard vehicle control system to a remote-control system in accordance with one embodiment.

FIG. 24 illustrates a flowchart of a method 2400 for transferring control of the movement of the vehicle system from the OVCS to the remote-control system. The operations of the method 2400 may be completed one or more of prior to or during the transfer of control of the movement of the vehicle system from the OVCS to the remote-control system.

At 2402, the OVCS is communicatively linked to the remote-control system via the control mediation system. For example, the OVCS is communicatively linked to the control mediation system by the communication link, and the remote-control system is communicatively linked to the control mediation system by the communication links.

At 2404, control of the movement of the vehicle system is controlled by the OVCS. For example, when control of the movement of the vehicle system is controlled by the OVCS, one or more operators of the remote-control system are unable to control the movement of the vehicle system. The OVCS controls the movement of the vehicle system by directing the propulsion subsystem to change the movement of the vehicle system by one or more of changing a throttle notch setting, a brake setting, speed setting, or the like. For example, the OVCS may autonomously or manually by an operator onboard the vehicle direct propulsion subsystem to decrease the speed of the vehicle system to 45 kilometers per hour. In response, the propulsion subsystem may decrease the throttle notch setting and/or apply the brakes to adhere to the 45 kph speed direction.

At 2406, a decision is made to determine if control of the movement of the vehicle system needs to transfer from the OVCS to the remote-control system. The decision is based on one or more of a location, a condition of the vehicle system, or an operator (e.g., onboard or off-board) request and/or condition. For example, the control of the movement of the vehicle system may need to transfer to the remote-control system if the vehicle system is traveling in a non-congested area (e.g., an open plane with minimal or no natural or manmade obstructions). Optionally, the location of the vehicle system may be any alternative location that would benefit by the remote-control system remotely controlling the movement of the vehicle system.

Alternatively, the control of the movement of the vehicle system may transfer to the remote-control system if the vehicle system has not experienced a fault state for a designated threshold amount of time and/or length of travel along the route. For example, the OVCS may communicate to one or more of the remote-control system or an alternative system that the status of each vehicle and/or the vehicle system is functioning appropriately for a given amount of time and/or distance of travel. Optionally, the condition of the vehicle system may be any alternative condition that would benefit by the remote-control system remotely controlling of the movement of the vehicle system.

Alternatively, the control of the movement of the vehicle system may transfer to the remote-control system if the operator of the OVCS or the operator of the remote-control system has initiated a request to transfer control of the movement. For example, the onboard operator of the OVCS may reach a designated break time and need to transfer control of the movement of the vehicle system to the remote-control system to take a designated work break. Optionally, the onboard operator of the OVCS may have a decrease in alertness prohibiting the onboard operator of the OVCS from safely controlling the movement of the vehicle system. Optionally, the request and/or condition of the operator onboard the vehicle system and/or the operator of the remote-control system may be any alternative request or condition that would benefit by the remote-control system controlling the movement of the vehicle system.

If control of the movement of the vehicle system does not need to transfer to the remote-control system, then flow of the method returns to 2404 and the OVCS continues to control the movement of the vehicle system (autonomously or manually). If control of the movement of the vehicle system does need to transfer to the remote-control system, then flow of the method proceeds to 2407.

At 2407, transfer of control of the movement of the vehicle system from the OVCS to the remote-control system is initiated. The transfer of control may be initiated by one or more of an operator of the remote-control system, an operator onboard the vehicle system, or autonomously by the OVCS.

At 2408, the control mediation system locks out an operator and autonomous control of the EMS onboard the vehicle system. For example, the control mediation system may prevent control signals one or more of input by the operator onboard the vehicle control system or autonomously by the OVCS from controlling the movement of the vehicle system.

At 2410, the OVCS receives an instruction from the remote-control system via the control mediation system to test an operation of the vehicle system. For example, the instruction may be to perform an airbrake test, switch headlights on and/or off, or the like.

At 2412, the OVCS communicates visual data representative of an area outside of the vehicle system to the remote-control system. For example, the object detection sensor may obtain still or motion image data of the area outside of the vehicle system (e.g., in front of, behind, to the side, above, or the like). The OVCS may communicate the obtained visual data to the remote-control system in which the visual data is displayed by the display of the remote-control system. The visual data informs the operator of the remote-control system of one or more of the condition, location, region, or the like of the vehicle system. For example, the visual data may inform the operator of the remote-control system that the route is clear of any obstructions. Additionally, the visual data informs the operator of the remote-control system if the instruction of 2410 was received by the OVCS and if the instruction was successfully completed by the OVCS. For example, the visual data may inform the operator of the remote-control system that the instruction the turn the headlights on and/or off was received and/or accurately completed.

At 2414, the one or more processors of the control mediation system completes the transfer of control of the movement of the vehicle system from the OVCS to the remote-control system. For example, the control mediation system may lock out or prevent control signals by the OVCS (manually or autonomously) from controlling the movement of the vehicle system.

At 2416, one or more of the operator onboard or near the vehicle system, the one or more operators of the remote-control system, or an operator of an alternative system are notified that the transfer of control of the movement of the vehicle system is complete. For example, the operator onboard the vehicle system may be notified by the output device changing to a different color, changing to a different display format, sounding a bell, communicating a vocal command, communicating a sound, by the OVCS changing and/or dimming the interior lights of the vehicle, or the like. Optionally, the operator onboard the vehicle system may be notified by any alternative method. The one or more operators of the remote-control system may be notified that the transfer of control of the movement of the vehicle system is complete by one or more of the display or the output device changing to a different color, changing to a different display format, sounding a bell, communicating a vocal command, communicating a sound, or the like. Optionally, the one or more operators of the remote-control system may be notified by any alternative method.

Figure 25:
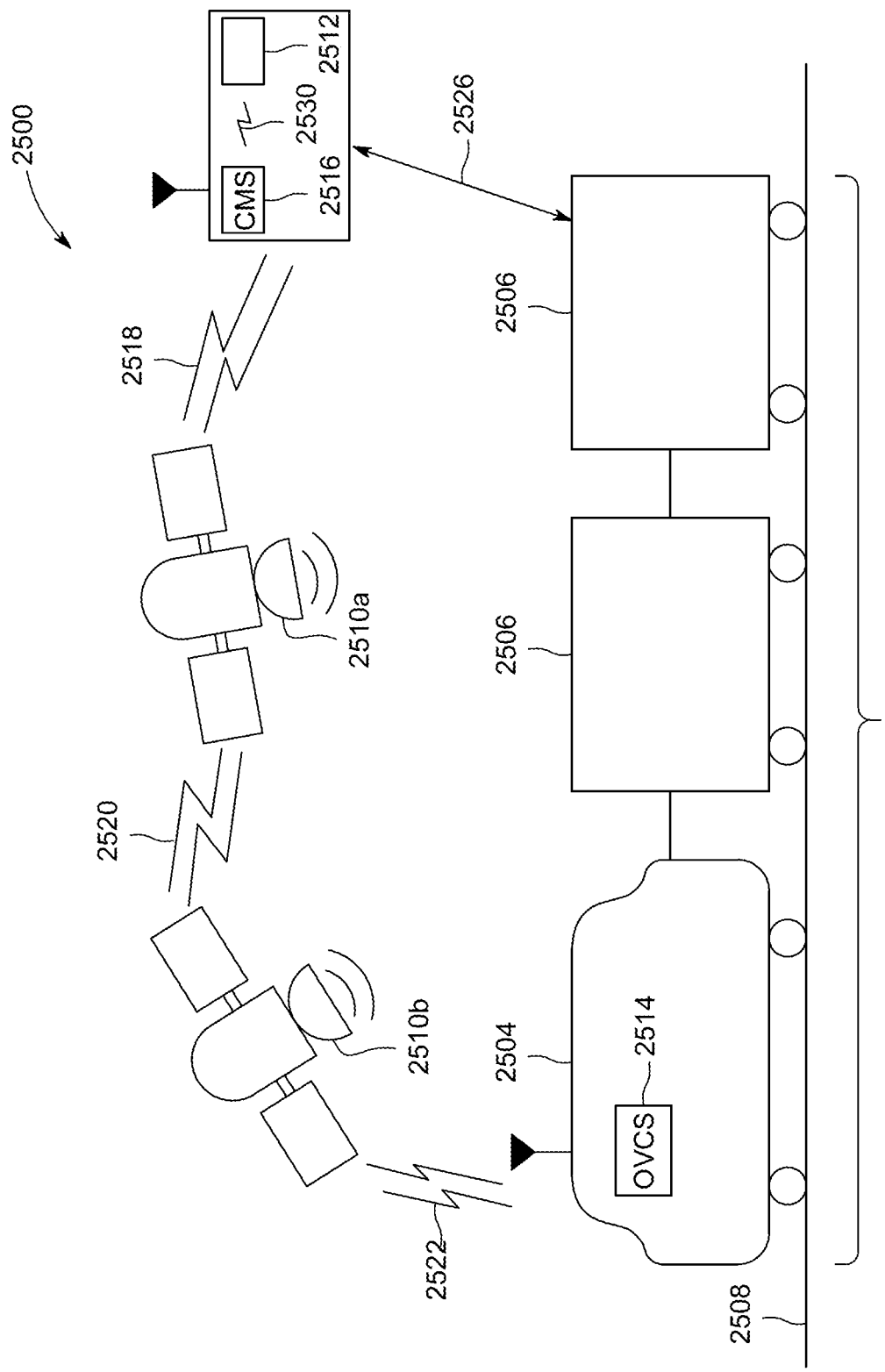
FIG. 25 illustrates a schematic illustration of a system of a vehicle system in accordance with one embodiment.

FIG. 25 illustrates one embodiment of a system 2500 that includes a vehicle system 2502. The illustrated vehicle system 2502 includes a propulsion-generating vehicle 2504 and non-propulsion generating vehicles. Although the vehicles are shown as being mechanically coupled with each other, optionally the vehicles may not be mechanically coupled with each other.

The propulsion-generating vehicle 2504 includes an onboard vehicle control system (OVCS) 2514 (corresponding to the OVCS 2014) disposed onboard the vehicle 2504. The OVCS 2514 can include hardware circuits or circuitry that include and/or are connected with one or more processors. The OVCS 2514 can control or limit movement of the propulsion-generating vehicle 2504 and/or the vehicle system 2502 that includes the vehicles based on one or more limitations.

The system 2500 includes a remote-control system 2512 (corresponding to the remote-control system 2012 of FIG. 20) disposed off-board the vehicle system 2502. The remote-control system 2512 remotely controls movement of the vehicle system 2502 by communicating movement operational settings to the vehicle system 2502. Multiple operators at the remote-control system 2512 can remotely control the movement of the vehicle system 2502. For example, multiple operators may remotely control multiple, different moving heavy vehicles (e.g., trains, vessels, automobiles, or the like).

The remote-control system 2512 includes a control mediation system 2516 (corresponding to the control mediation system 2016 of FIG. 20). The control mediation system 2516 represents hardware circuitry that includes and/or is connected with one or more processors (e.g., microprocessors, controllers, field programmable gate arrays, integrated circuits, or the like). The remote-control system 2512 is operably connected with the control mediation system 2516 by a communication link 2530. The communication link 2530 may represent a wired or wireless connection. Additionally, the control mediation system 2516 is wirelessly connected with the OVCS 2514 onboard the vehicle system 2502.

The remote-control system 2512 is separated from the vehicle system 2502 by a distance 2526. The distance 2526 may be 50 meters, 500 meters, 500 kilometers, 5000 kilometers, or the like. The distance 2526 between the vehicle system 2502 and the remote-control system 2512 can be beyond a line of site of an operator of the remote-control system 2512 to the vehicle system 2502, can extend between different time zones, can extend between different geographical locations (e.g., different town, county, state, country) or the like. For example, an operator of the remote-control system 2512 may control the movement of the vehicle system 2502 when the operator of the remote-control system 2512 is located in New York and the vehicle system 2502 located in Utah. Alternatively, the distance 2526 may be within a line a site of an operator of the remote-control system 2512 to the vehicle system 2502. For example, the distance 2526 may be less than 50 meters.

The remote-control system 2512 is communicatively linked with the OVCS 2514 of the vehicle 2504 by communication links 2518, 2520, 2522, 2530 established between the remote-control system 2512 and the vehicle system 2502. For example, the remote-control system 2512 communicates control signals to the control mediation system 2516 by the communication link 2530. The control mediation system 2516 communicates the control signals to a first satellite 2510a by the communication link 2518. The first satellite 2510a communicates the control signals to a second satellite 2510b by the communication link 2520. The second satellite 2510b communicates the control signals to the OVCS 2514 by the communication link 2522. Optionally, less than two or more than two satellites may be used to communicate signals between the remote-control system 2512 and the vehicle system 2502. Additionally or alternatively, the vehicle system 2502 may communicate with the remote-control system 2512 with terrestrial communications repeaters (e.g., radio towers). Optionally, the vehicle system 2502 and remote-control system 2512 may communicate by communication links established between one or more satellites and/or one or more radio towers, or the like. Additionally, the remote-control system 2512 is communicatively linked with the OVCS 2514 by the communication link 2530 established between the remote-control system 2512 and the vehicle system 2502. For example, the control mediation system 2516 communicates control signals between the remote-control system (e.g., by communication link 2530) and the OVCS 2514 (e.g., by the communication links 2518, 2520, 2522).

The remote-control system 2512 communicates control signals to the vehicle system 2502 by the communication links 2518, 2520, 2522, 2530 in order to remotely control the movement of the vehicle system 2502 as the vehicle system 2502 travels along the route 2508. The control signals dictate the movement operational settings of the vehicle system 2502 that include one or more of a throttle notch setting, a brake setting, speed setting or the like.

The one or more processers of the control mediation system 2516 communicatively link the remote-control system 2512 disposed off-board the vehicle system with the OVCS 2514 disposed onboard the vehicle system 2502. The one or more processors of the control mediation system 2516 mediate a process of transferring control of the movement of the vehicle system 2502 from the remote-control system 2512 to the OVCS 2514 or from the OVCS 2514 to the remote-control system 2512. For example, the control mediation system 2516 mediates (e.g., manages, arbitrates, or the like) which system controls the vehicle system 2502 to ensure the control of the movement of the vehicle system is controlled by a single system at a given time. For example, when control of the movement of the vehicle system is managed by the remote-control system 2512, the movement of the vehicle system 2502 cannot be controlled autonomously by the OVCS 2114 or manually by an operator onboard the vehicle system 2502. Additionally, when control of the movement of the vehicle system 2502 is managed by the OVCS 2514 (manually or autonomously), the vehicle system 2502 cannot be controlled by the remote-control system 2512.

Control of the movement of the vehicle system 2502 may transfer from the remote-control system 2512 to the OVCS 2514 or from the OVCS 2514 to the remote-control system 2512 based on a location, a condition of the vehicle system 2502, or an operator request and/or condition. The location is a designated geographic area or a designated segment of the route 2508 which is either known a priori or calculated according to some track and/or region characteristics. For example, these areas may be based on population density, track work locations, grade crossing locations, vehicle work locations (e.g., pick-up or set-out of vehicles), a designated practice area for manual control of the vehicle system 2502, or the like. The condition may be a fault state of the vehicle system 2502, may be a communication loss between the vehicle system 2502 and the remote-control system 2512, may be an increase or decrease of a rate of fuel consumption above a designated non-zero threshold, or the like. The operator request and/or condition may be based on a level of alertness of the operator onboard the vehicle system 2502 or the operator of the remote-control system 2512, a designated work break and/or stoppage for one or more operators, or the like.

The remote-control system 2512 is configured to remotely control movement of the vehicle system 2502 by sending control signals to the OVCS 2514 onboard the vehicle 2504 via the control mediation system 2516. Additionally, the OVCS 2514 is configured to control movement of the vehicle system 2502 one or more of autonomously or manually by an operator onboard the vehicle system 2502. The one or more processors of the control mediation system 2516 control which of the remote-control system 2512 or the OVCS 2514 controls the movement of the vehicle system at a given time. Additionally, the control mediation system 2516 mediates the transfer of control of the movement of the vehicle system from the remote-control system 2512 to the OVCS 2514 or from the OVCS 2514 to the remote-control system 2512.

In one embodiment of the subject matter described herein, a system is provided that includes one or more processors configured to communicatively link a remote-control system disposed off-board a vehicle system with an onboard vehicle control system on the vehicle system. The remote-control system and the onboard vehicle control system are configured to control movement of the vehicle system, wherein the one or more processors are configured to transfer control of the movement of the vehicle system from the remote-control system to the onboard vehicle control system based on one or more of a location, a condition of the vehicle system, or by one or more of a request or condition of an operator or from the onboard vehicle control system to the remote-control system based on the one or more of the location, the condition of the vehicle system, or by the one or more of the request or condition of the operator.

Optionally, the one or more processors are configured to generate and provide a notification signal to an output device onboard the vehicle system that automatically informs the operator onboard or near the vehicle system of transfer of control of the movement of the vehicle system from the remote-control system to the onboard vehicle control system or from the onboard vehicle control system to the remote-control system.

Optionally, the one or more processors are configured to transfer control of the movement of the vehicle system from the remote-control system to the onboard vehicle control system or transfer control of the movement of the vehicle system to the remote-control system from the onboard vehicle control system responsive to the vehicle system entering the location being a designated geographic area or a designated segment of a route. Optionally, the location is a designated practice area for manual control of the vehicle system by the operator. Optionally the condition is a fault state of the vehicle system. Optionally, the condition is a communication loss between the vehicle system and the remote-control system. Optionally, the condition is a decreased alertness of the operator.

Optionally, the onboard vehicle control system is configured to one or more of automatically control the movement of the vehicle system without operator intervention or automatically present instructions to the operator that instruct the operator how to control the movement of the vehicle system.

Optionally, the one or more processors are configured to lock out operator control of the movement of the vehicle system, receive instructions from the remote-control system to test an operation of the vehicle system, and communicate visual data representative of an area outside of the vehicle system to the remote-control system prior to or during transfer of control of the movement of the vehicle system from the onboard vehicle control system to the remote-control system.

Optionally, the one or more processors are configured to automatically stop the vehicle system, activate the onboard vehicle control system, and disconnect communication with the remote-control system prior to or during transfer of control of the movement of the vehicle system from the remote-control system to the onboard vehicle control system.

In one embodiment of the subject matter described herein, a method is provided that includes communicatively linking a remote-control system disposed off-board a vehicle system and an onboard vehicle control system on the vehicle system with one or more processors. The remote-control system and the onboard vehicle control system are configured to control movement of the vehicle system. The method includes transferring control of the movement of the vehicle system from the remote-control system to the onboard vehicle control system based on one or more of a location, a condition of the vehicle system, or one or more of a request or condition of an operator or from the onboard vehicle control system to the remote-control system based on the one or more of the location, the condition of the vehicle system, or the one or more of the request or condition of the operator with the one or more processors.

Optionally, the one or more processors transfer control of the movement of the vehicle system from the remote-control system to the onboard vehicle control system or transfer control of the movement of the vehicle system to the remote-control system from the onboard vehicle control system responsive to the vehicle system entering the location being a designated geographic area or a designated segment of a route. Optionally, the location is a designated practice area for manual control of the vehicle system by the operator. Optionally, the condition is a fault state of the vehicle system. Optionally, the condition is a communication loss between the vehicle system and the remote-control system. Optionally, the condition is a decreased alertness of the operator.

Optionally, the method includes the onboard vehicle control system one or more of automatically controlling the movement of the vehicle system without operator intervention or automatically presenting instructions to the operator that instruct the operator how to control the movement of the vehicle system.

Optionally, the method includes locking out operator control of the movement of the vehicle system, receiving an instruction from the remote-control system to test an operation of the vehicle system, and communicating visual data representative of an area outside of the vehicle system to the remote-control system prior to or during transferring of control of the movement of the vehicle system from the onboard vehicle control system to the remote-control system.

Optionally, the method includes automatically stopping the vehicle system, activating the onboard vehicle control system, and disconnecting with the remote-control system prior to or during transferring of control of the movement of the vehicle system from the remote-control system to the onboard vehicle control system.

In one embodiment of the subject matter described herein, a system is provided that includes one or more processors configured to communicatively link with a vehicle system for remotely controlling movement of the vehicle system. The vehicle system also includes an onboard vehicle control system for locally controlling movement of the vehicle system, wherein the one or more processors are configured to transfer control of the movement of the vehicle system from the remote-control system to the onboard vehicle control system based on one or more of a location, a condition of the vehicle system, or one or more of a request or condition of an operator or from the onboard vehicle control system to the remote-control system based on the one or more of the location, the condition of the vehicle system, or the one or more of the request or condition of the operator.

Optionally, the one or more processors are configured to transfer control of the movement of the vehicle system from the remote-control system to the onboard vehicle control system or to transfer control of the movement of the vehicle system to the remote-control system from the onboard vehicle control system responsive to the vehicle system entering the location being a designated geographic area or a designated segment of a route. Optionally, the location is a designated practice area for manual control of the vehicle system by the operator. Optionally, the condition is a fault state of the vehicle system. Optionally, the condition is a communication loss between the vehicle system and the remote-control system. Optionally, the condition is a decreased alertness of the operator.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose several embodiments of the inventive subject matter, including the best mode, and also to enable one of ordinary skill in the art to practice the embodiments of inventive subject matter, including making and using any devices or systems and performing any incorporated methods. The patentable scope of the inventive subject matter is defined by the claims, and may include other examples that occur to one of ordinary skill in the art. Such other examples are intended to be within the scope of the claims if they have structural elements that do not differ from the literal language of the claims, or if they include equivalent structural elements with insubstantial differences from the literal languages of the claims.

The foregoing description of certain embodiments of the present inventive subject matter will be better understood when read in conjunction with the appended drawings. The various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "comprises," "including," "includes," "having," or "has" an element or a plurality of elements having a particular property may include additional such elements not having that property.

What is claimed is:

1. A system comprising:
one or more processors configured to communicatively link a remote-control system disposed off-board a vehicle system with an onboard vehicle control system on the vehicle system, the remote-control system and the onboard vehicle control system configured to control movement of the vehicle system;
wherein the one or more processors are configured to transfer control of the movement of the vehicle system between the remote-control system and the onboard vehicle control system based on one or more of a location, a condition of the vehicle system, or a request or condition of an operator, wherein control of the movement of the vehicle system includes controlling one or more of a throttle setting or a brake setting of the vehicle system, and
wherein the one or more processors are configured to automatically stop the vehicle system, activate the onboard vehicle control system, and disconnect communication with the remote-control system prior to or during transfer of control of the movement of the vehicle system from the remote-control system to the onboard vehicle control system.

2. The system of claim 1, wherein the one or more processors are configured to generate and provide a notification signal to an output device onboard the vehicle system that automatically informs the operator onboard or near the vehicle system of transfer of control of the movement of the vehicle system from the remote-control system to the onboard vehicle control system or from the onboard vehicle control system to the remote-control system.

3. The system of claim 1, wherein the one or more processors are configured to transfer control of the movement of the vehicle system from the remote-control system to the onboard vehicle control system or to transfer control of the movement of the vehicle system to the remote-control system from the onboard vehicle control system responsive to the vehicle system entering the location being a designated geographic area or a designated segment of a route.

4. The system of claim 1, wherein the location is a designated practice area for manual control of the vehicle system by the operator.

5. The system of claim 1, wherein the condition is a fault state of the vehicle system.

6. The system of claim 1, wherein the condition is a communication loss between the vehicle system and the remote-control system.

7. The system of claim 1, wherein the condition is a decreased alertness of the operator.

8. The system of claim 1, wherein the onboard vehicle control system is configured to one or more of automatically control the movement of the vehicle system without operator intervention or automatically present instructions to the operator that instruct the operator how to control the movement of the vehicle system.

9. The system of claim 1, wherein the one or more processors are configured to lock out operator control of the movement of the vehicle system, receive an instruction from the remote-control system to test an operation of the vehicle system, and communicate visual data representative of an area outside of the vehicle system to the remote-control system prior to or during transfer of control of the movement of the vehicle system from the onboard vehicle control system to the remote-control system.

10. A method comprising:
communicatively linking a remote-control system disposed off-board a vehicle system and an onboard vehicle control system on the vehicle system with one or more processors, the remote-control system and the onboard vehicle control system configured to control movement of the vehicle system, wherein control of the movement of the vehicle system includes controlling one or more of a throttle setting or a brake setting of the vehicle system,
transferring control of the movement of the vehicle system between the remote-control system and the onboard vehicle control system based on one or more of a location, a condition of the vehicle system, or a request or condition of an operator, and
automatically stopping the vehicle system, activating the onboard vehicle control system, and disconnecting communication with the remote-control system prior to or during transferring of control of the movement of the vehicle system from the remote-control system to the onboard vehicle control system.

11. The method of claim 10, wherein the one or more processors transfer control of the movement of the vehicle system from the remote-control system to the onboard vehicle control system or transfer control of the movement of the vehicle system to the remote-control system from the onboard vehicle control system responsive to the vehicle system entering the location being a designated geographic area of a designated segment of a route.

12. The method of claim 10, wherein the location is a designated practice area for manual control of the vehicle system by the operator.

13. The method of claim 10, wherein the condition is a fault state of the vehicle system.

14. The method of claim 10, wherein the condition is a communication loss between the vehicle system and the remote-control system.

15. The method of claim 10, wherein the condition is a decreased alertness of the operator.

16. The method of claim 10, further comprising one or more of automatically controlling the movement of the vehicle system without operator intervention or automatically presenting instructions to the operator that instruct the operator how to control the movement of the vehicle system.

17. The method of claim 10, further comprising locking out operator control of the movement of the vehicle system, receiving an instruction from the remote-control system to test an operation of the vehicle system, and communicating visual data representative of an area outside of the vehicle system to the remote-control system prior to or during transferring of control of the movement of the vehicle system from the onboard vehicle control system to the remote-control system.

18. A system comprising:
one or more processors configured to communicatively link with a vehicle system for remotely controlling movement of the vehicle system, the vehicle system also including an onboard vehicle control system for locally controlling movement of the vehicle system,
wherein the one or more processors are configured to transfer control of the movement of the vehicle system between a remote-control system and the onboard vehicle control system based on one or more of a location, a condition of the vehicle system, or a request or condition of an operator, wherein control of the movement of the vehicle system includes controlling one or more of a throttle setting or brake setting of the vehicle system, and
wherein the one or more processors are configured to automatically stop the vehicle system, activate the onboard vehicle control system, and disconnect communication with the remote-control system prior to or during transfer of control of the movement of the vehicle system from the remote-control system to the onboard vehicle control system.

19. The system of claim 18, wherein the one or more processors are configured to transfer control of the movement of the vehicle system from the remote-control system to the onboard vehicle control system or to transfer control of the movement of the vehicle system to the remote-control system from the onboard vehicle control system responsive to the vehicle system entering the location being a designated geographic area or a designated segment of a route.

20. The system of claim 18, wherein the location a designated practice area for manual control of the vehicle system by the operator.

21. The system of claim 18, wherein the condition as a fault state of the vehicle system.

22. The system of claim 18, wherein the condition as a communication loss between the vehicle system and the remote-control system.

23. The system of claim 18, wherein the condition is a decreased alertness of the operator.

* * * * *